US008592414B2

(12) United States Patent
Palmer et al.

(10) Patent No.: US 8,592,414 B2
(45) Date of Patent: Nov. 26, 2013

(54) JNK INHIBITORS FOR THE TREATMENT OF ENDOMETRIOSIS

(75) Inventors: Stephen S. Palmer, Plympton, MA (US); Selvaraj Nataraja, Randolph, MA (US)

(73) Assignee: Merck Serono, S.A., Geneva (CH)

( * ) Notice: Subject to any disclaimer, the term of this patent is extended or adjusted under 35 U.S.C. 154(b) by 285 days.

(21) Appl. No.: 11/988,572

(22) PCT Filed: Jul. 12, 2006

(86) PCT No.: PCT/US2006/027455
§ 371 (c)(1),
(2), (4) Date: Apr. 23, 2008

(87) PCT Pub. No.: WO2007/011762
PCT Pub. Date: Jan. 25, 2007

(65) Prior Publication Data
US 2009/0176761 A1 Jul. 9, 2009

Related U.S. Application Data

(60) Provisional application No. 60/699,658, filed on Jul. 15, 2005.

(30) Foreign Application Priority Data
Oct. 11, 2005 (EP) .................................. 05109447

(51) Int. Cl.
*A61K 31/535* (2006.01)
(52) U.S. Cl.
USPC ..................................................... 514/232.5

(58) Field of Classification Search
USPC ...................................................... 514/232.5
See application file for complete search history.

(56) References Cited

U.S. PATENT DOCUMENTS

| 4,988,679 A | 1/1991 | Chavkin et al. |
| 5,433,951 A | 7/1995 | Serajuddin et al. |
| 5,540,938 A | 7/1996 | Masterson et al. |
| 7,838,522 B2 | 11/2010 | Esposito et al. |
| 2002/0127555 A1 | 9/2002 | Baban et al. |
| 2003/0175920 A1 | 9/2003 | Bonny |
| 2004/0067953 A1 | 4/2004 | Stein et al. |
| 2006/0177509 A1 | 8/2006 | Nagahara et al. |
| 2008/0051397 A1* | 2/2008 | Esposito et al. ........... 514/233.8 |

FOREIGN PATENT DOCUMENTS

| EP | 0727406 B1 | 8/1996 |
| WO | WO 85/01959 | 5/1985 |
| WO | WO 86/04589 | 8/1986 |
| WO | WO 88/10270 | 12/1988 |
| WO | WO 92/13095 | 8/1992 |

(Continued)

OTHER PUBLICATIONS

Rice, VM, Ann. N.Y. Acad. Sci., (Mar. 2002) 955, pp. 343-352.*

(Continued)

*Primary Examiner* — San-Ming Hui
(74) *Attorney, Agent, or Firm* — Hamilton, Brook, Smith & Reynolds, P.C.

(57) ABSTRACT

This invention relates to a method of treating and/or preventing endometriosis comprising administering a JNK inhibitor. The JNK inhibitor can also be administered combined with a hormonal suppressor. The invention further relates to the treatment of endometriosis-related infertility.

15 Claims, 5 Drawing Sheets

(56) References Cited

FOREIGN PATENT DOCUMENTS

| | | |
|---|---|---|
| WO | WO 98/48802 | 11/1998 |
| WO | WO 99/55678 | 11/1999 |
| WO | WO 99/67230 | 12/1999 |
| WO | WO 00/35906 | 6/2000 |
| WO | WO 00/35909 | 6/2000 |
| WO | WO 00/35920 | 6/2000 |
| WO | WO 00/64872 | 11/2000 |
| WO | WO 00/75118 A1 | 12/2000 |
| WO | WO 01/12609 A1 | 2/2001 |
| WO | WO 01/12621 A1 | 2/2001 |
| WO | WO 01/23378 A1 | 4/2001 |
| WO | WO 01/23379 A1 | 4/2001 |
| WO | WO 01/23382 A1 | 4/2001 |
| WO | WO 01/45698 A1 | 6/2001 |
| WO | WO 01/47920 A | 7/2001 |
| WO | WO 01/47920 A1 | 7/2001 |
| WO | WO 02/26733 A2 | 4/2002 |
| WO | WO 02/28856 A1 | 4/2002 |
| WO | WO 02/28866 A2 | 4/2002 |
| WO | WO 03/018022 A1 | 3/2003 |
| WO | WO 03/047570 A1 | 6/2003 |
| WO | WO 03/070711 A1 | 8/2003 |
| WO | WO 03/091249 A | 11/2003 |
| WO | WO 03/091249 A1 | 11/2003 |
| WO | WO 2004/007457 A | 1/2004 |
| WO | WO 2004/028251 A1 | 4/2004 |
| WO | WO 2004/043965 A1 | 5/2004 |
| WO | WO 2005/025567 A1 | 3/2005 |
| WO | WO 2005/049192 A1 | 6/2005 |

OTHER PUBLICATIONS

Lessey et al., Fertility Sterility (Mar. 1989) 51(3), pp. 409-415 (abstract).*
Metzger et al., Hum Pathol. (Dec. 1988) 19(12), pp. 1417-1424 (abstract).*
International Preliminary Report on Patentability from counterpart International Application No. PCT/US2006/027455, dated Jan. 24, 2008.
Aungst, B., et al., "Improved Oral Bioavailability of an HIV Protease Inhibitor Using Gelucire 44/14 and Labrasol Vehicles," *Bull. Tech. Gattefossé*, 87: 49-54 (1994).
Bruner-Tran, K., et al., "Experimental Endometriosis: The Nude Mouse as a Xenographic Host," *Annals New York Academy of Sciences*, 955: 328-339 (2002).
Chabaka, L., et al., "Facile Synthesis of 2-Furyl-, 2-Pyrrolyl-, 2-Imidazolyl- and Pyrrolo-Azoles from 2-Substituted Methylazoles," *Polish Journal of Chemistry*, 68: 1317-1325 (1994).
D'Antonio, M., et al., "Ability of Recombinant Human TNF Binding Protein-1 (r-hTBP-1) to Inhibit the Development of Experimentally-Induced Endometriosis in Rats," *Journal of Reproductive Immunology*, 48: 81-98 (2000).
International Search Report for International Application No. PCT/EP2005/056020 dated Jun. 7, 2006.
Written Opinion of the International Searching Authority, International Application No. PCT/EP2005/056020 dated Jun. 7, 2006.
Jadhav, N., et al. [Gelucires: Pharmaceutical Applications, Pharmainfo.net 6(4) (2008) 1-11].
Golub, T.R., et al., "Molecular Classification of Cancer: Class Discovery and Class Predication by Gene Expression Monitoring," *Science*, 286:531-536 (Oct. 1999).
Lala, P.K., et al., "Role of Nitric Oxide in Tumor Progression: Lessons From Experimental Tumors," *Cancer and Metastasis Reviews*, 17(1):91-106 (1998).
Barcz, Ewa, et al., "Role of cytokines in pathogenesis of endometriosis", *Med Sci Monit*, vol. 6, No. 5, pp. 1042-1046, 2000.
Bruner-Tran, Kaylon L., et al. "Experimental Endometriosis: The Nude Mouse as a Xenographic Host", Annals of the New York Academy of Sciences, pp. 328-339, 2002.
Bulun, Serdar E., et al., "Progesterone resistance in endometriosis: Link to failure to metabolize estradiol", *Molecular and Cellular Endocrinology*, vol. 248, pp. 94-103, Elsevier Ireland Ltd., 2006.
D'Antonio, M., et al., "Ability of recombinant human TNF binding protein-1 (r-hTBP-1) to inhibit the development of experimentally-induced endometriosis in rats", *Journal of Reproductive Immunology*, Elsevier Science Ireland Ltd., vol. 48, pp. 81-98, 2000.
D'Hooghe, T.M., et al., "Recombinant human TNF binding protein-1 (r-hTBP-1) inhibits the development of endometriosis in baboons: a prospective, randomized, placebo- and drug-controlled study", p. S1 Fertility & Sterility, 2001.
Dawood, M.Y., "Considerations in selecting appropriate medical therapy for endometriosis", *Int J. Gynecol Obstet*, vol. 40, pp. S29-S42, International Federation of Gynecology and Obstetrics, 1993.
Dent, Paul, et al., "MAPK pathways in radiation responses", *Oncogene*, vol. 22, pp. 5885-5896, 2003.
Frixen, Uwe H., et al., "E-Cadherin-mediated Cell-Cell Adhesion Prevents Invasiveness of Human Carcinoma Cells", *The Journal of Cell Biology*, vol. 113, No. 1, The Rockefeller University Press, pp. 173-185, Apr. 1991.
Giudice, Linda C., et al., "Endometriosis", Lancet, vol. 364, pp. 1789-1799, Nov. 2004.
Gupta, Shashi, et al., "Selective interaction of JNK protein kinase isofoinis with transcription factors", *The EMBO Journal*, vol. 15, No. 11, pp. 2760-2770, Oxford University Press, 1996.
Kyama, Cleophas M., et al., "Potential involvement of the immune system in the development of endometriosis", Reproductive Biology and Endocrinology, vol. 1, 123, Dec. 2003.
Shazand, K., et al., "FOXO1 and c-jun transcription factors mRNA are modulated in endometriosis", *Molecular Human Reproduction*, vol. 10, No. 12, European Society of Human Reproduction and Embryology, vol. 10, pp. 871-877, Oct. 2004.
Waller, Kathleen G., et al., "Gonadotropin-releasing hormone analogues for the treatment of endometriosis: long-term follow-up", *Fertility & Sterility*, vol. 59, No. 3, pp. 511-515, The American Fertility Society, Mar. 1993.
Yoshino, O., et al., "Possible Pathophysiological Roles of Mitogen-Activated Protein Kinases (MAPKs) in Endometriosis", *American Journal of Reproductive Immunology*, vol. 52, pp. 306-311, Blackwell Munksgaard, 2004.
Zeitvogel, Andreas, et al., "Identification of an Invasive, N-Cadherin-Expressing Epithelial Cell Type in Endometriosis Using a New Cell Culture Model", *American Journal of Pathology*, vol. 159, No. 5, American Society for Investigative Pathology, pp. 1839-1852, Nov. 2001.

* cited by examiner

JNK INHIBITORS FOR THE TREATMENT OF ENDOMETRIOSIS

This application is the U.S. National Stage of International Application No. PCT/US2006/027455, filed Jul. 12, 2006, published in English, and claims priority under 35 U.S.C. §119 or 365 to European Application No. 05109447.2, filed Oct. 11, 2005 and U.S. Provisional Application No. 60/699,658, filed Jul. 15, 2005.

BACKGROUND OF THE INVENTION

Endometriosis is one of the most frequent diseases of women in their reproductive lifespan. It is characterized by the presence of endometrial tissue outside the uterine cavity, consisting histological of glands and stroma. The anatomical sites most often affected are the ovaries, uterosacral ligaments, pelvic peritoneum, rectovaginal septum, cervix, vagina, the fallopian tubes and vulva.

Endometriosis is considered to be a benign disease, but endometriotic lesions occasionally become malignant. As in other kind of malignancies, the development of endometriosis-derived neoplasms is due to concurrent events, involving alterations in growth factors and/or oncogenes regulation (Kyama e al. 2003). Further, endometriosis is considered as a major cause of infertility (Giudice et al. 2004).

The current treatment of endometriosis consists of hormonal therapy and/or surgery. Hormonal therapies include high dose of progestogens, progestins, oral contraceptives (combinations of estrogen and progesterone), Danazol (an androgenic derivative of ethisterone) and more recently GnRH agonists. These hormonal therapies are effective on pelvic pain and may induce an objective regression of lesions, but have several caveats. Estrogen may stimulate and cause proliferation of endometriotic tissue since it may be unable to respond to progesterone (Dawood et al, 1993). Progestational agents can provoke irregular bleeding along with depression, weight gain, and fluid retention. Danazol can improve symptoms in approximately 66-100% of the patients suffering from pain, but recurrence rates after up to 4 years are approximately 40%-50%. Other drawbacks of Danazol therapy are weight gain and androgenic side effects. GnRH analogs are more potent and long acting than native GnRH, which act by removing the estrogenic stimulus for the growth of all estrogen sensitive tissues. Side effects of GnRH analogs are mainly secondary to the profound hypoestrogenemia, like decreased bone density, and recurrence rate are up to 50% after 5 years (Waller et al., 1993). Further complicating treatment is the observation that endometriotic lesions in many patients either are or become resistant to the effects of progesterone and/or progestins. (Bulun et al. 2006).

Surgical intervention can be conservative, if fertility is desired, or can lead to the removal of the uterus, tubes and ovaries in case of severe disease. In any case, even limited surgical treatment leads to a significant decrease in fertility.

Although endometriosis stands as one of the most investigated disorders of gynecology, the current understanding of pathophysiology of the disease remains elusive. According to a favored theory, endometriotic lesions develop by eutopic endometrial cells leaving their primary site, possibly by retrograde menstruation, and implant at distant sites, followed by invasion of host tissue and proliferation. Furthermore, it appears that endometriosis is an invasive and metastasizing disease. Though endometriotic cells proliferate to a certain extent, they are not neoplastic as typically found in carcinomas. Apparently, endometriotic cells become senescent, apoptotic and necrotic. Inflammatory responses that are induced or accompanied by lesion formation finally lead to fibrosis and the formation of scars.

It has been speculated whether tumor or metastasis suppressor genes (e.g. E-cadherin) are associated with endometriosis. E-cadherin is a metastasis suppressor molecule, its down-regulation or functional inactivation is a prerequisite for invasion and metastasis (Frixen et al, 1991). Zeitvogel et al. (2001) showed that E-cadherin is absent and N-cadherin is present in endometriotic cells. N-cadherin is suggested to be the path-finding molecule that allows cells to be invasive and migratory in normal development and pathological processes.

Recently, it has been demonstrated that recombinant human TNFα binding protein (rh-TBP-1) is effective in reducing the size and severity of endometriotic lesions in an experimental model of endometriosis (D'Hooghe et al. 2001). These results were the first to demonstrate that an anti-inflammatory molecule (r-hTBP-1) that targeted the TNFα-pathway provided effective medical treatment for patients with endometriosis that did not inhibit ovulation.

Yoshino et al. (2004) showed that mitogen-activated protein kinases (MAPKs), which are intracellular signal transducers, mediate some of the effects exerted by proinflammatory cytokines. Yoshino et al. further showed the presence of MAPks (e.g. ERK, JNK and p38) in endometriotic cells and their phosphorylation under inflammatory stimulation by IL-1β, TNFα and $H_2O_2$. MAPKs are serine/threonine kinases that are activated by dual phosphorylation on threonine and tyrosine residues. In mammalian cells, there are at least three separate but parallel pathways that convey information generated by extra-cellular stimuli to the MAPKs. Said pathways consist of kinase cascades leading to activation of the ERKs (extracellular regulated kinases), the JNKs (c-Jun N-terminal kinases), and the p38/CSBP kinases (Dent et al 2003).

c-Jun is a protein that forms homodimers and heterodimers (with e.g. c-Fos) to produce the transactivating complex AP-1, which is required for the activation of many genes (e.g. matrix metalloproteinases) involved in the inflammatory response.

The invention described herein clearly shows the unexpected result that inhibiting JNK, by means of a JNK inhibitor, reduces endometriotic-like foci in a rat and in nude mouse experimental models. A rat model also demonstrates that such effect is obtained by inhibiting the Natural Killer cells activity associated with the disease as well as reducing several cytokines found elevated in endometriosis. These cytokines are among others, IL-6 and IL-8 that are suggested to play a key role (Barcz et al., 2000). The JNK inhibitors described herein restore the sensitivity of endometrial cells and lesions to progesterone. Furthermore, the JNK inhibitors described herein used in combination with a SPRM or progestin can prevent re-establishment of endometriosis. The reduction of endometriotic lesions using JNK inhibitors can also improve fertility rates, since the normalization of genital structure has a positive effect on the implantation rate.

Several small molecules have been proposed as modulators of the JNK pathway.

Aryl-oxindole derivatives of respectively the generic formula (A) (WO 00/35909; WO 00/35906; WO 00/35920) and formula (B) (WO 00/64872) have been developed for the treatment of neurodegenerative diseases, inflammation and solid tumors for formula (A) and for the treatment of a broad range of disorders including, neurodegenerative diseases, inflammatory and autoimmune diseases, cardiovascular and bone disorders for formula (B).

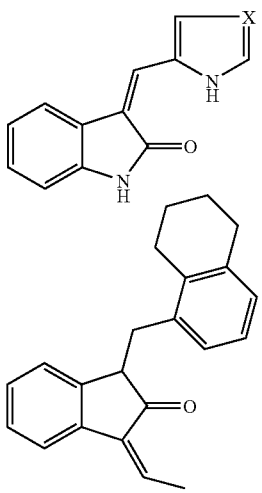

(A)

(B)

Pyrazoloanthrones derivatives of formula (C) have been reported to inhibit JNK for the treatment of neurological degenerative diseases, inflammatory and autoimmune disorders as well as cardiovascular pathologies (WO 01/12609).

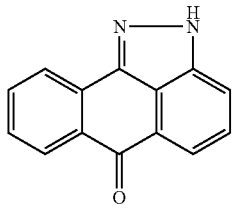

(C)

Tetrahydro-pyrimidine derivatives of formula (D) were reported to be JNK inhibitors useful in the treatment of a wide range of diseases including neurodegenerative diseases, inflammatory and autoimmune disorders, cardiac and destructive bone pathologies (WO 00/75118).

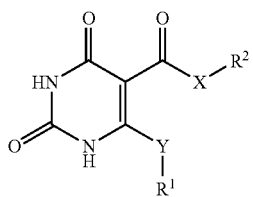

(D)

Other heterocyclic compounds of formula (E) have been proposed to inhibit protein kinases and especially c-un-N-Terminal kinases (WO 01/12621) for treating "JNK-mediated conditions" including proliferative diseases, neurodegenerative disorders, inflammatory and autoimmune disorders.

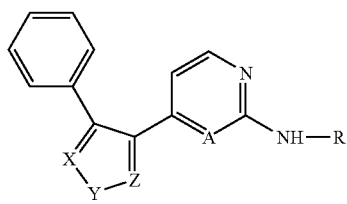

(E)

Benzazoles derivatives such as represented by formula (F) (WO 01/47920) have been described as modulators of the JNK pathway for the treatment of neuronal disorders, autoimmune diseases, cancers and cardiovascular diseases.

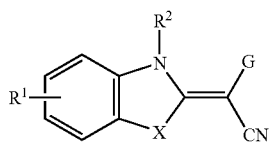

(F)

Several sulfonamide derivatives of formula (G) (WO 01/23378), sulfonyl amino acid derivatives of formula (H) (WO 01/23379) and sulfonyl hydrazide derivatives of formula (J) (WO 01/23382), were also developed to inhibit JNKs for treating neurodegenerative diseases, auto-immune disorders, cancers and cardiovascular diseases.

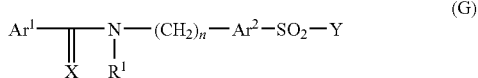

(G)

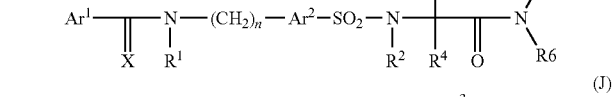

(H)

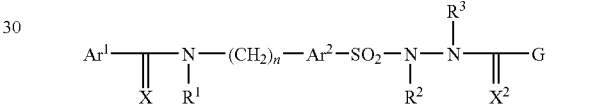

(J)

SUMMARY OF THE INVENTION

The present invention relates to a method of treating and/or preventing endometriosis in an individual comprising administering a therapeutically effective amount of a JNK inhibitor.

The invention further relates to a method of treating and/or preventing endometriosis by combined treatment of hormonal suppressor (e.g. GnRH antagonists, GnRH agonists, aromatase inhibitors, progesterone receptor modulators, estrogen receptor modulators) along with a JNK inhibitor.

The invention also relates to a method of treating endometriosis-related infertility in a female comprising the administration of a therapeutically effective amount of a JNK inhibitor, alone or in combination with other fertility drugs.

The invention finally relates to a pharmaceutical composition comprising a JNK inhibitor, a hormonal suppressor and a pharmaceutically acceptable excipient.

Figure 3:
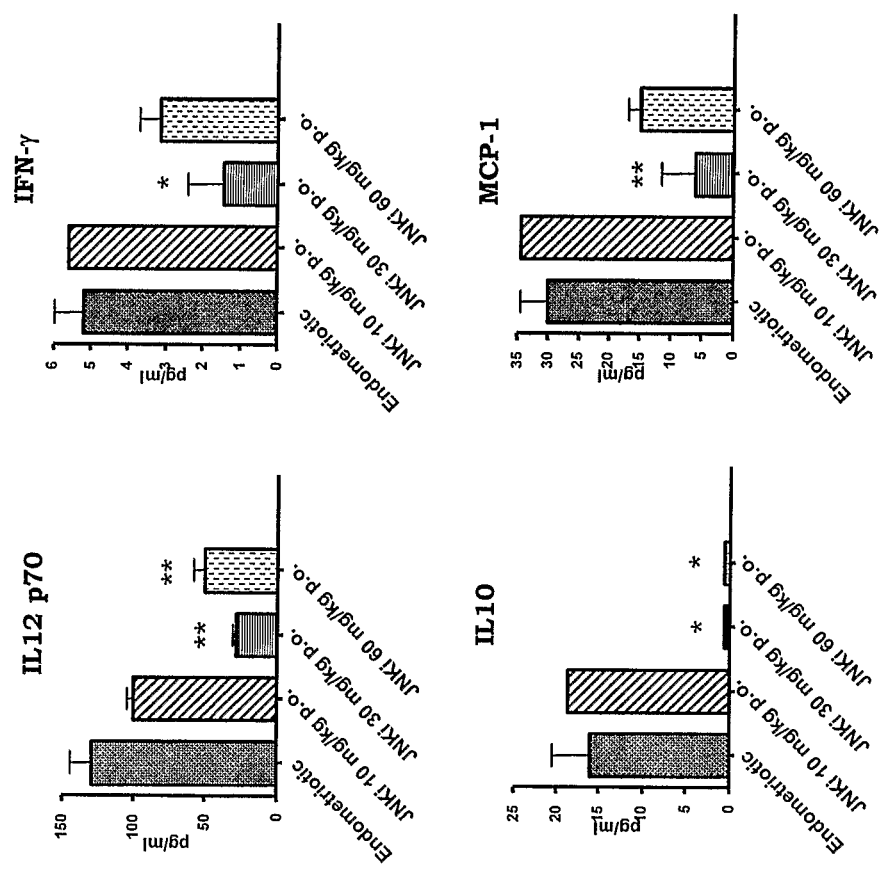

FIG. 3: Effect of JNK inhibitor on cytokines in endometriotic-like foci in the rat endometriosis model. The JNK inhibitor reduced the levels of inflammatory cytokines, IL-12, INF-γ, IL-10 and MCP-1 in the endometriotic foci.

Figure 4:
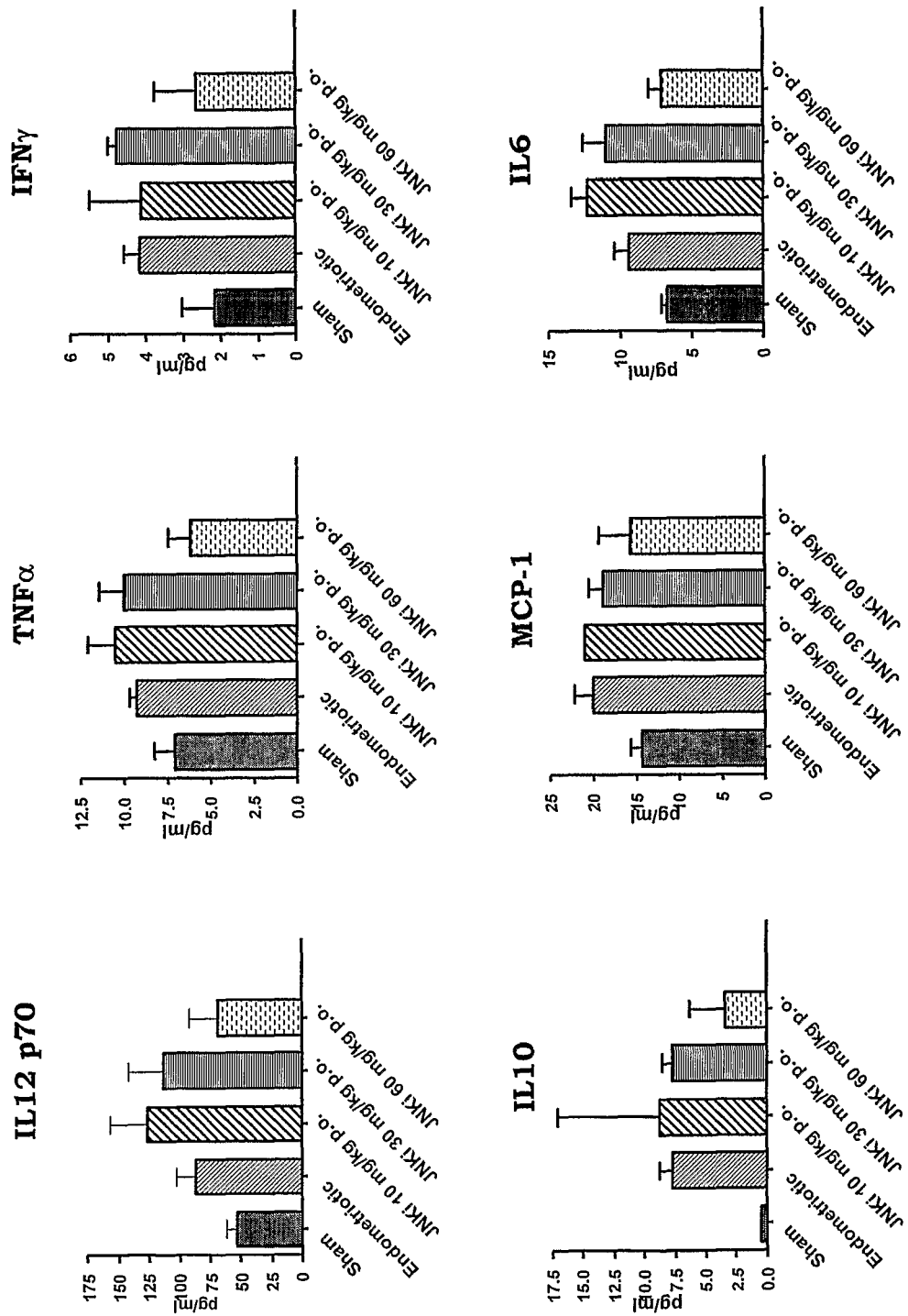

FIG. 4: Effect of JNK inhibitor on cytokines in the contralateral horn in experimentally induced endometriosis in rats. No effect of the JNK inhibitor on cytokine expression was observed.

Figure 5:
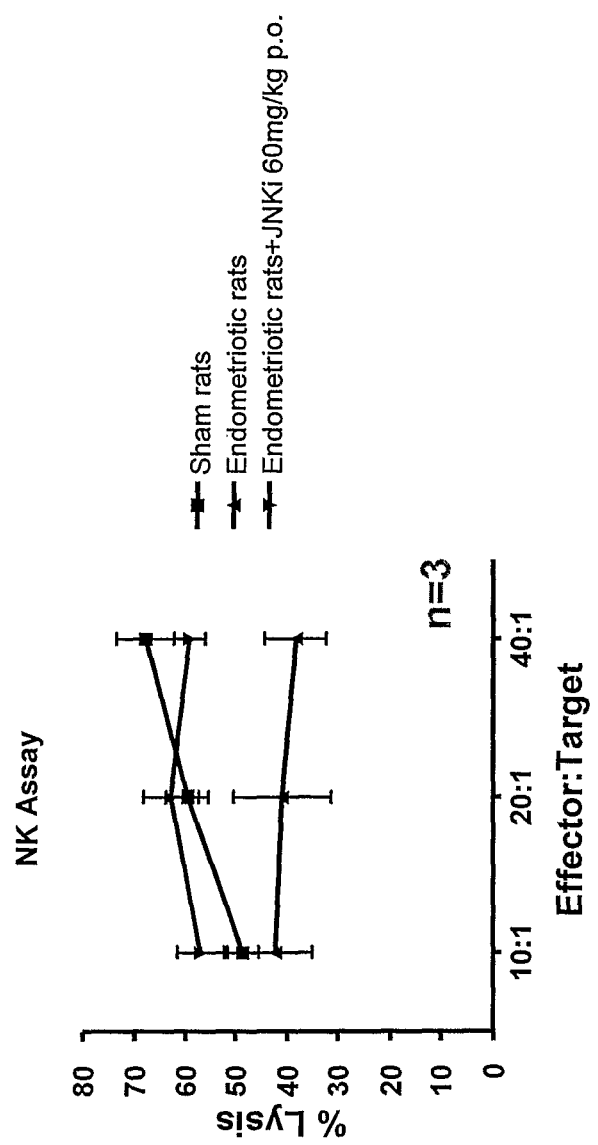

FIG. 5: Effect of JNK inhibitor on NK-cell activity in the rat endometriosis model. Treatment with a JNK inhibitor increased NK cell activity compared to the vehicle treated group.

DESCRIPTION OF THE INVENTION

The following paragraphs provide definitions of the various chemical moieties that make up the compounds according to the invention and are intended to apply uniformly throughout the specification and claims unless an otherwise expressly set out definition provides a broader definition.

"$C_1$-$C_6$-alkyl" refers to alkyl groups having 1 to 6 carbon atoms. This term is exemplified by groups such as methyl, ethyl, n-propyl, isopropyl, n-butyl, isobutyl, tert-butyl, n-butyl, n-pentyl, n-hexyl and the like.

"Aryl" refers to an unsaturated aromatic carbocyclic group of from 6 to 14 carbon atoms having a single ring (e.g., phenyl) or multiple condensed rings (e.g., naphthyl). Preferred aryl include phenyl, naphthyl, phenantrenyl and the like.

"$C_1$-$C_6$-alkyl aryl" refers to $C_1$-$C_6$-alkyl groups having an aryl substituent, including benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"$C_1$-$C_6$-alkyl heteroaryl" refers to $C_1$-$C_6$-alkyl groups having a heteroaryl substituent, including 2-furylmethyl, 2-thienylmethyl, 2-(1H-indol-3-yl)ethyl and the like.

"$C_2$-$C_6$-alkenyl" refers to alkenyl groups preferably having from 2 to 6 carbon atoms and having at least 1 or 2 sites of alkenyl unsaturation. Preferable alkenyl groups include ethenyl (—CH=CH$_2$), n-2-propenyl (allyl, —CH$_2$CH=CH$_2$) and the like.

"$C_2$-$C_6$-alkenyl aryl" refers to $C_2$-$C_6$-alkenyl groups having an aryl substituent, including 2-phenylvinyl and the like.

"$C_2$-$C_6$-alkenyl heteroaryl" refers to $C_2$-$C_6$-alkenyl groups having a heteroaryl substituent, including 2-(3-pyridinyl)vinyl and the like.

"$C_2$-$C_6$-alkynyl" refers to alkynyl groups preferably having from 2 to 6 carbon atoms and having at least 1-2 sites of alkynyl unsaturation, preferred alkynyl groups include ethynyl (—C≡CH), propargyl (—CH$_2$C≡CH), and the like.

"$C_2$-$C_6$-alkynyl aryl" refers to $C_2$-$C_6$-alkynyl groups having an aryl substituent, including phenylethynyl and the like.

"$C_2$-$C_6$-alkynyl heteroaryl" refers to $C_2$-$C_6$-alkynyl groups having a heteroaryl substituent, including 2-thienylethynyl and the like.

"$C_3$-$C_8$-cycloalkyl" refers to a saturated carbocyclic group of from 3 to 8 carbon atoms having a single ring (e.g., cyclohexyl) or multiple condensed rings (e.g., norbornyl). Preferred cycloalkyl include cyclopentyl, cyclohexyl, norbornyl and the like.

"$C_1$-$C_6$-alkyl cycloalkyl" refers to $C_1$-$C_6$-alkyl groups having a cycloalkyl substituent, including cyclohexylmethyl, cyclopentylpropyl, and the like.

"Heterocycloalkyl" refers to a $C_3$-$C_8$-cycloalkyl group according to the definition above, in which 1 to 3 carbon atoms are replaced by hetero atoms chosen from the group consisting of O, S, NR, R being defined as hydrogen or $C_1$-$C_6$ alkyl. Preferred heterocycloalkyl include pyrrolidine, piperidine, piperazine, 1-methylpiperazine, morpholine, and the like.

"$C_1$-$C_6$-alkyl heterocycloalkyl" refers to $C_1$-$C_6$-alkyl groups having a heterocycloalkyl substituent, including 2-(1-pyrrolidinyl)ethyl, 4-morpholinylmethyl, (1-methyl-4-piperidinyl)methyl and the like.

"Carboxy" refers to the group —C(O)OH.

"$C_1$-$C_6$-alkyl carboxy" refers to $C_1$-$C_6$-alkyl groups having a carboxy substituent, including 2-carboxyethyl and the like.

"Acyl" refers to the group —C(O)R where R includes H, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl acyl" refers to $C_1$-$C_6$-alkyl groups having an acyl substituent, including 2-acetylethyl and the like.

"Acyloxy" refers to the group —OC(O)R where R includes H, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl acyloxy" refers to $C_1$-$C_6$-alkyl groups having an acyloxy substituent, including 2-(acetyloxy)ethyl and the like.

"Alkoxy" refers to the group —O—R where R includes "$C_1$-$C_6$-alkyl", "$C_2$-$C_6$-alkenyl", "$C_2$-$C_6$-alkynyl", "$C_3$-$C_8$-cycloalkyl", "Heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-allyl alkoxy" refers to $C_1$-$C_6$-alkyl groups having an alkoxy substituent, including 2-ethoxyethyl and the like.

"Alkoxycarbonyl" refers to the group —C(O)OR where R includes "$C_1$-$C_6$-alkyl", "$C_2$-$C_6$-alkenyl", "$C_2$-$C_6$-alkynyl", "$C_3$-$C_8$-cycloalkyl", "Heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl alkoxycarbonyl" refers to $C_1$-$C_6$-alkyl groups having an alkoxycarbonyl substituent, including 2-(benzyloxycarbonyl)ethyl and the like.

"Aminocarbonyl" refers to the group —C(O)NRR' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "Heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl aminocarbonyl" refers to $C_1$-$C_6$-alkyl groups having an aminocarbonyl substituent, including 2-(dimethylaminocarbonyl)ethyl and the like.

"Acylamino" refers to the group —NRC(O)R' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "Heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl acylamino" refers to $C_1$-$C_6$-alkyl groups having an acylamino substituent, including 2-(propionylamino)ethyl and the like.

"Ureido" refers to the group —NRC(O)NR'R" where each R, R', R" is independently hydrogen, "$C_1$-$C_6$-alkyl", "$C_2$-$C_6$-alkenyl", "$C_2$-$C_6$-alkynyl", "$C_3$-$C_8$-cycloalkyl", "Heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl", and where R' and R", together with the nitrogen atom to which they are attached, can optionally form a 3-8-membered heterocycloalkyl ring.

"$C_1$-$C_6$-alkyl ureido" refers to $C_1$-$C_6$-alkyl groups having an ureido substituent, including 2-(N'-methylureido)ethyl and the like.

"Amino" refers to the group —NRR' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "Heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl", and where R and R', together with the nitrogen atom to which they are attached, can optionally form a 3-8-membered hetero-cycloalkyl ring.

"$C_1$-$C_6$-alkyl amino" refers to $C_1$-$C_6$-alkyl groups having an amino substituent, including 2-(1-pyrrolidinyl)ethyl and the like.

"Cyclic amino" refers to piperazinyl, piperidinyL, imidazolidinyl, imidazolinyl, imidazolyl, indolinyl, isoindolinyl, pyrazolidinyl, pyrrolidinyl "Acyclic amino" refers to the group —NRR' where each R, R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl", or "cycloalkyl", or "heterocycloalkyl" and also refers to the ammonium group —N+RR'R" such as defined hereinafter "Ammonium" refers to a positively charged group —N+RR'R", where each R, R', R" is independently, "$C_1$-$C_6$-alkyl", "$C_2$-$C_6$-alkenyl", "$C_2$-$C_6$-alkynyl", "$C_3$-$C_8$-cycloalkyl", "Heterocycloalkyl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl", and where R and R', together with the nitrogen atom to which they are attached, can optionally form a 3-8-membered heterocycloalkyl ring.

"$C_1$-$C_6$-alkyl ammonium" refers to $C_1$-$C_6$-alkyl groups having an ammonium substituent, including 2-(1-pyrrolidinyl)ethyl and the like.

"Halogen" refers to fluoro, chloro, bromo and iodo atoms.

"Sulfonyloxy" refers to a group —OSO$_2$—R wherein R is selected from H, "$C_1$-$C_6$-alkyl", "$C_1$-$C_6$-alkyl" substituted with halogens, e.g., an —OSO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfonyloxy" refers to $C_1$-$C_6$-alkyl groups having a sulfonyloxy substituent, including 2-(methylsulfonyloxy)ethyl and the like.

"Sulfonyl" refers to group "—SO$_2$—R" wherein R is selected from H, "aryl", "heteroaryl", "$C_1$-$C_6$-alkyl", "$C_1$-$C_6$-alkyl" substituted with halogens, e.g., an —SO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-allyl sulfonyl" refers to $C_1$-$C_6$-alkyl groups having a sulfonyl substituent, including 2-(methylsulfonyl)ethyl and the like.

"Sulfinyl" refers to a group "—S(O)—R" wherein R is selected from H, "$C_1$-$C_6$-alkyl", "$C_1$-$C_6$-alkyl" substituted with halogens, e.g., an —SO—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfinyl" refers to $C_1$-$C_6$-alkyl groups having a sulfinyl substituent, including 2-(methylsulfinyl)ethyl and the like.

"Sulfanyl" refers to groups —S—R where R includes H, "$C_1$-$C_6$-alkyl", "$C_1$-$C_6$-alkyl" substituted with halogens, e.g., an —SO—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl". Preferred sulfanyl groups include methylsulfanyl, ethylsulfanyl, and the like.

"$C_1$-$C_6$-alkyl sulfanyl" refers to $C_1$-$C_6$-alkyl groups having a sulfanyl substituent, including 2-(ethylsulfanyl)ethyl and the like.

"Sulfonylamino" refers to a group —NRSO$_2$—R' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfonylamino" refers to $C_1$-$C_6$-alkyl groups having a sulfonylamino substituent, including 2-(ethylsulfonylamino)ethyl and the like.

"Aminosulfonyl" refers to a group —SO$_2$—NRR' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl"

or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynyl-heteroaryl", "$C_1$-$C_6$-alkyl cycloalkyl", "$C_1$-$C_6$-alkyl heterocycloalkyl".

"$C_1$-$C_6$-alkyl aminosulfonyl" refers to $C_1$-$C_6$-alkyl groups having an aminosulfonyl substituent, including 2-(cyclohexylaminosulfonyl)ethyl and the like.

"Substituted or unsubstituted": Unless otherwise constrained by the definition of the individual substituent, the above set out groups, like "alkyl", "alkenyl", "alkynyl", "aryl" and "heteroaryl" etc. groups can optionally be substituted with from 1 to 5 substituents selected from the group consisting of "$C_1$-$C_6$-alkyl", "$C_2$-$C_6$-alkenyl", "$C_2$-$C_6$-alkynyl", "cycloalkyl", "heterocycloalkyl", "$C_1$-$C_6$-alkyl aryl", "$C_1$-$C_6$-alkyl heteroaryl", "$C_1$-$C_6$-alkyl cycloalkyl", "$C_1$-$C_6$-alkyl heterocycloalkyl", "amino", "ammonium", "acyl", "acyloxy", "acylamino", "aminocarbonyl", "alkoxycarbonyl", "ureido", "aryl", "heteroaryl", "sulfinyl", "sulfonyl", "alkoxy", "sulfanyl", "halogen", "carboxy", trihalomethyl, cyano, hydroxy, mercapto, nitro, and the like. Alternatively said substitution could also comprise situations where neighbouring substituents have undergone ring closure, notably when vicinal functional substituents are involved, thus forming, e.g., lactams, lactons, cyclic anhydrides, but also acetals, thioacetals, aminals formed by ring closure for instance in an effort to obtain a protective group.

"Pharmaceutically acceptable salts or complexes" refers to salts or complexes that retain the desired biological activity of the below-identified compounds of formula I and exhibit minor or no undesired toxicological effects. Examples of such salts include, but are not restricted to acid addition salts formed with inorganic acids (e.g. hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and polygalacturonic acid. Said compounds can also be administered as pharmaceutically acceptable quaternary salts known by a person skilled in the art, which specifically include the quarternary ammonium salt of the formula —NR,R',R"$^+$Z$^-$, wherein R, R', R" is independently hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Pharmaceutically active derivative" refers to any compound that upon administration to the recipient, is capable of providing directly or indirectly, the activity disclosed herein.

The "tautomers" of the compounds according to formula I are only those wherein $R^2$ and/or $R^0$ are hydrogen and which display the formulae (Ia) and (Ib).

"Enantiomeric excess" (ee) refers to the products that are obtained by an asymmetric synthesis, i.e. a synthesis involving non-racemic starting materials and/or reagents or a synthesis comprising at least one enantioselective step, whereby a surplus of one enantiomer in the order of at least about 52% ee is yielded.

"Aromatase Inhibitors" refers to drugs that inhibit the enzyme aromatase and by that lowers the level of the estradiol. Preferred aromatase inhibitors include by way of example anastrozole, letrozole, vorozole and exemestane.

"Estrogen receptor modulators (SERM)" refers to drugs that block the actions of estrogen by occupying the estrogen receptors on cells. SERMS also include estrogen receptor beta antagonists and estrogen receptor beta agonists. Preferred SERMs include by way of example Tamoxifen, Raloxifen.

"GnRH antagonists" refers to synthetic GnRH analogues, which are drugs that competitively block the pituitary GnRH receptor, which is located on the plasma membrane of gonadotrophs, inducing a rapid, reversible suppression of gonadotrophin secretion. Preferred GnRH antagonists include by way of example Cetrorelix, Ganirelix.

"GnRH agonists" refers to decapeptide modifications of the natural hormone GnRH, which are drugs that desensitize GnRH receptors of the pituitary gland at continued exposure, which causes an initial stimulation of the pituitary-ovarian axis, followed by a reduction in circulating serum gonadotrophin concentration and inhibition of ovarian function. Preferred GnRH agonists include by way of example Buserelin acetate, Nafarelin, Leuprolide, Triptorelin, Goserelin.

"JNK" means a protein or an isoform thereof expressed by a JNK 1, JNK 2, or JNK 3 gene (Gupta et al. 1996).

"JNK-inhibitor" refers to a compound, a peptide or a protein that inhibits c-jun amino terminal kinase (JNK) phosphorylation of a JNK targeted transcription factor. The JNK-inhibitor is an agent capable of inhibiting the activity of JNK in vitro or in vivo. Such inhibitory activity can be determined by an assay or animal model well-known in the art.

"Progesterone receptor modulators (SPRMs)": The progesterone receptor, a member of the superfamily of nuclear receptors, is the receptor for progesterone that plays a pivotal role in female reproduction. Selective progesterone receptor modulators are drugs that can have agonist, antagonist or partial (mixed) agonist/antagonist activities depending upon the site of action. A preferred SPRM includes by way of example asoprisnil.

One embodiment of the present invention is to provide a method of treating and/or preventing endometriosis in an individual comprising administering a therapeutically effective amount of a JNK inhibitor.

Another embodiment of the present invention relates to a method of treating and/or preventing endometriosis by sequential or combined treatment of a hormonal suppressor (e.g. GnRH antagonists, GnRH agonists, aromatase inhibitors, progesterone receptor modulators, estrogen receptor modulators) along with a JNK inhibitor.

Second or subsequent administrations of therapeutically effective amounts can be performed at a dosage which is the same, less than or greater than the initial or previous dose administered to the individual. Second or subsequent administrations can be administered during or prior to relapse of the endometriosis or the related symptoms. The terms "relapse" or "reoccurrence" are defined to encompass the appearance of one or more of symptoms of endometriosis.

In another embodiment, the invention relates to a method of treating endometriosis-related infertility in a female comprising the administration of a therapeutically effective amount of a JNK inhibitor, alone or in combination with other fertility drugs.

In a further embodiment, the sequential or combined treatment regimen minimizes the disease by suppressing endocrine-dependent cells.

Another embodiment of the present invention consists of a pharmaceutical composition comprising a JNK inhibitor, a hormonal suppressor (e.g. GnRH antagonists, GnRH agonists, aromatase inhibitors, progesterone receptor modulators, estrogen receptor modulators) and a pharmaceutically acceptable excipient.

Another embodiment of the present invention consists of the use of a JNK inhibitor in the manufacture of a medicament for the treatment and/or prevention of endometriosis.

The term "preventing", as used herein, should be understood as partially or totally preventing, inhibiting, alleviating, or reversing one or more symptoms or cause(s) of endometriosis.

A proposed model for progression of endometriotic disease predicts that lesions progress from benign inflammatory lesions responsive to endocrine intervention to partially or completely hormonally unresponsive lesions that involve upregulated survival pathways in addition to inflammatory pathways.

Therefore, in one embodiment, the JNK inhibitor may interfere with survival pathways in endometriosis.

Another embodiment of the invention relates to the use of a JNK inhibitor together with a hormonal suppressor (e.g. GnRH antagonists, GnRH agonists, aromatase inhibitors, progesterone receptor modulators, estrogen receptor modulators) and a pharmaceutically acceptable carrier in the manufacture of a medicament for the treatment and/or prevention of endometriosis.

The use of a JNK inhibitor together with a hormonal suppressor (e.g. GnRH antagonists, GnRH agonists, aromatase inhibitors, progesterone receptor modulators, estrogen receptor modulators) can be a sequential or a combined use of the JNK inhibitor and the hormonal suppressor.

Another embodiment of the invention, relates to the use of a JNK inhibitor, alone or in combination with other drugs, in the manufacture of a medicament for the treatment of endometriosis-related infertility.

In particular, when endometriosis-related infertility is intended to be treated or cured, biologically active human chorionic gonadotrophin (hCG), luteinizing hormone (LH) or follicle stimulating hormone (FSH), either in a natural highly purified or in a recombinant form, can be administered. Such molecules and methods of their production have been described in the European Patent Applications EP 160,699, EP 211,894 and EP 322,438.

The pharmaceutical compositions of the present invention can be administered by a variety of routes including oral, rectal, transdermal, subcutaneous, intravenous, intramuscular and intranasal. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the JNK inhibitor is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like.

Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as pepper-mint, methyl salicylate, or orange flavoring.

Injectable compositions are typically based upon injectable sterile saline or phosphate-buffered saline or other injectable carriers known in the art. As above-mentioned, the JNK inhibitor in such compositions is typically a minor component, frequently ranging between 0.05 to 10% by weight with the remainder being the injectable carrier and the like.

The above-described components for orally administered or injectable compositions are merely representative. Further materials as well as processing techniques and the like are set out in Part 5 of *Remington's Pharmaceutical Sciences*, 20$^{th}$ Edition, 2000, Marck Publishing Company, Easton, Pa., which is incorporated herein by reference.

The compounds of this invention can also be administered in sustained release forms or from sustained release drug delivery systems. A description of representative sustained release materials can also be found in the incorporated materials in *Remington's Pharmaceutical Sciences*.

The definition of "pharmaceutically acceptable" is meant to encompass any carrier, which does not interfere with effectiveness of the biological activity of the active ingredient and that is not toxic to the host to which it is administered. For example, for parenteral administration, JNK inhibitor may be formulated in a unit dosage form for injection in vehicles such as saline, dextrose solution, serum albumin and Ringer's solution.

For parenteral (e.g. intravenous, subcutaneous, intramuscular) administration, JNK inhibitors can be formulated as a solution, suspension, emulsion or lyophilized powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

The therapeutically effective amounts of a JNK inhibitor will be a function of many variables, including the type of inhibitor, the affinity of the inhibitor for JNK, any residual cytotoxic activity exhibited by the JNK inhibitor, the route of administration or the clinical condition of the patient.

A "therapeutically effective amount" is such that when administered, the JNK inhibitor results in inhibition of the biological activity of JNK. The dosage administered, as single or multiple doses, to an individual will vary depending upon a variety of factor, including JNK inhibitor pharmacokinetic properties, the route of administration, patient conditions and characteristics (sex, age, body weight, health, size), extent of symptoms, concurrent treatments, frequency of treatment and the effect desired. Adjustment and manipulation of established dosage ranges are well within the ability of those skilled, as well as in vitro and in vivo methods of determining the inhibition of JNK in an individual.

The JNK inhibitors may be of formula (I)

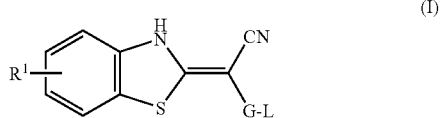

(I)

Said compounds are disclosed in WO 01/47920 (Applied Research Systems ARS Holding Nev.) in which benzazoles derivatives of formula (A) are described in particular for the treatment of neuronal disorders, autoimmune diseases, cancer and cardiovascular diseases:

In the compounds according to formula (I):

G is an unsubstituted or substituted pyrimidinyl group.

L is an unsubstituted or substituted $C_1$-$C_6$-alkoxy, or an amino group, or an unsubstituted or a substituted 3-8 membered heterocycloalkyl, containing at least one heteroatom selected from N, O, S (e.g. a piperazine, a piperidine, a morpholine, a pyrrolidine).

$R^1$ is selected from the group comprising or consisting of hydrogen, sulfonyl, amino, unsubstituted or substituted $C_1$-$C_6$-alkyl, unsubstituted or substituted $C_2$-$C_6$-alkenyl, unsubstituted or substituted $C_2$-$C_6$-alkynyl or $C_1$-$C_6$-alkoxy, unsubstituted or substituted aryl (e.g. phenyl), halogen, cyano or hydroxy.

Preferably $R^1$ is H or $C_1$-$C_3$ alkyl (e.g. a methyl or ethyl group).

Formula (I) also comprises its tautomers, its geometrical isomers, its optically active forms as enantiomers, diastereomers and its racemate forms, as well as pharmaceutically acceptable salts thereof. Preferred pharmaceutically acceptable salts of the formula (I) are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

More specifically, the benzothiazole acetonitriles of formula (I) comprise the tautomeric forms, e.g. the below ones:

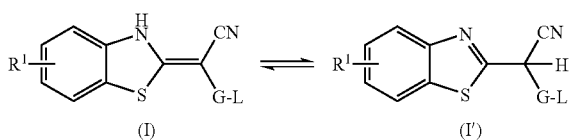

A specific embodiment of the present invention consists in benzothiazole acetonitriles of formula (Ia) in its tautomeric forms, e.g. the below ones:

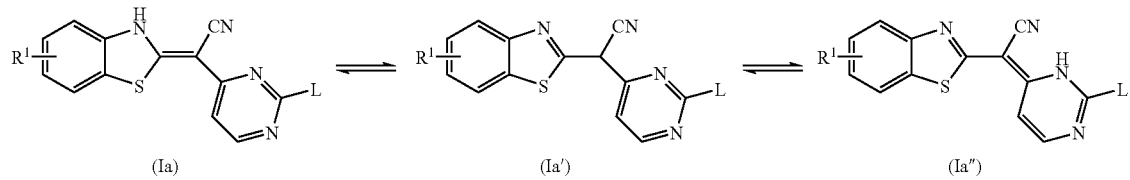

$R^1$ and L are as defined for formula (I).

According to a specific embodiment, the moiety L is an amino group of the formula —$NR^3R^4$ wherein $R^3$ and $R^4$ are each independently from each other H, unsubstituted or substituted $C_1$-$C_6$-alkyl, unsubstituted or substituted $C_2$-$C_6$-alkenyl, unsubstituted or substituted $C_2$-$C_6$-alkynyl, unsubstituted or substituted $C_1$-$C_6$-alkoxy, unsubstituted or substituted aryl, unsubstituted or substituted heteroaryl, unsubstituted or substituted saturated or unsaturated 3-8-membered cycloalkyl, unsubstituted or substituted 3-8-membered heterocycloalkyl, (wherein said cycloalkyl, heterocycloalkyl, aryl or heteroaryl groups may be fused with 1-2 further cycloalkyl, heterocycloalkyl, aryl or heteroaryl group), unsubstituted or substituted $C_1$-$C_6$-alkyl aryl, unsubstituted or substituted $C_1$-$C_6$-alkyl heteroaryl, unsubstituted or substituted $C_2$-$C_6$-alkenyl aryl, unsubstituted or substituted $C_2$-$C_6$-alkenyl heteroaryl, unsubstituted or substituted $C_2$-$C_6$-alkynyl aryl, unsubstituted or substituted $C_2$-$C_6$-alkynyl heteroaryl, unsubstituted or substituted $C_1$-$C_6$-alkyl cycloalkyl, unsubstituted or substituted $C_1$-$C_6$-alkyl heterocycloalkyl, unsubstituted or substituted $C_2$-$C_6$-alkenyl cycloalkyl, unsubstituted or substituted $C_2$-$C_6$-alkenyl heterocycloalkyl, unsubstituted or substituted $C_2$-$C_6$-alkynyl cycloalkyl, unsubstituted or substituted $C_2$-$C_6$-alkynyl heterocycloalkyl.

Alternatively, $R^3$ and $R^4$ may form a ring together with the nitrogen to which they are attached.

In a specific embodiment, $R^3$ is hydrogen or a methyl or ethyl or propyl group and $R^4$ is selected from the group consisting of unsubstituted or substituted ($C_1$-$C_6$)-alkyl, unsubstituted or substituted $C_1$-$C_6$ alkyl-aryl, unsubstituted or substituted $C_1$-$C_6$-alkyl-heteroaryl, unsubstituted or substituted cycloalkyl, unsubstituted or substituted heterocycloalkyl, unsubstituted or substituted aryl or heteroaryl and unsubstituted or substituted 4-8 membered saturated or unsaturated cycloalkyl.

In a further specific embodiment, $R^3$ and $R^4$ form a substituted or unsubstituted piperazine or a piperidine or a morpholine or a pyrrolidine ring together with the nitrogen to which they are bound, whereby said optional substituent is selected from the group consisting of unsubstituted or substituted $C_1$-$C_6$-alkyl, unsubstituted or substituted $C_2$-$C_6$-alkenyl, unsubstituted or substituted $C_2$-$C_6$-alkynyl, unsubstituted or substituted $C_1$-$C_6$-alkoxy, unsubstituted or substituted aryl, unsubstituted or substituted heteroaryl, unsubstituted or substituted saturated or unsaturated 3-8-membered cycloalkyl, unsubstituted or substituted 3-8-membered heterocycloalkyl, (wherein said cycloalkyl, heterocycloalkyl, aryl or heteroaryl groups may be fused with 1-2 further cycloalkyl, heterocycloalkyl, aryl or heteroaryl group), unsubstituted or substituted $C_1$-$C_6$-alkyl aryl, unsubstituted or substituted $C_1$-$C_6$-alkyl heteroaryl, unsubstituted or substituted $C_2$-$C_6$-alkenyl aryl, unsubstituted or substituted $C_2$-$C_6$-alkenyl heteroaryl, unsubstituted or substituted $C_2$-$C_6$-alkynyl aryl, unsubstituted or substituted $C_2$-$C_6$-alkynyl heteroaryl, unsubstituted or substituted $C_1$-$C_6$-alkyl cycloalkyl, unsubstituted or substituted $C_1$-$C_6$-alkyl heterocycloalkyl, unsubstituted or substituted $C_2$-$C_6$-alkenyl cycloalkyl, unsubstituted or substituted $C_2$-$C_6$-alkenyl heterocycloalkyl, unsubstituted or substituted $C_2$-$C_6$-alkynyl cycloalkyl, unsubstituted or substituted $C_2$-$C_6$-alkynyl heterocycloalkyl.

In a specific embodiment L is selected from:

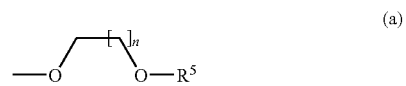

(a)

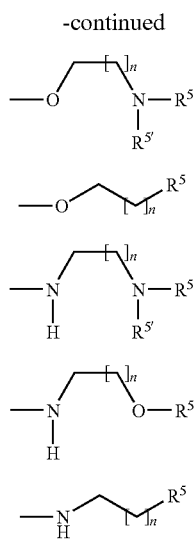

wherein n is 1 to 3, preferably 1 or 2.

$R^5$ and $R^{5'}$ are independently selected from each other from the group consisting of H, substituted or unsubstituted $C_1$-$C_6$ alkyl, substituted or unsubstituted aryl or substituted or unsubstituted heteroaryl, substituted or unsubstituted $C_1$-$C_6$ alkyl-aryl and substituted or unsubstituted $C_1$-$C_6$-alkyl-heteroaryl.

Compounds wherein L is moiety (d) are particularly preferred.

Specific examples of compounds of formula (I) include the following:

1,3-benzothiazol-2-yl(2,6-dimethoxy-4-pyrimidinyl)acetonitrile
1,3-benzothiazol-2-yl(2-{[2-(1H-imidazol-5-yl)ethyl]amino}-4-pyrimidinyl)acetonitrile
1,3-benzothiazol-2-yl[2-(1-piperazinyl)-4-pyrimidinyl]acetonitrile
1,3-benzothiazol-2-yl[2-(4-benzyl-1-piperidinyl)-4-pyrimidinyl]acetonitrile
1,3-benzothiazol-2-yl[2-(4-methyl-1-piperazinyl)-4-pyrimidinyl]acetonitrile
1,3-benzothiazol-2-yl[2-(4-morpholinyl)-4-pyrimidinyl]acetonitrile
1,3-benzothiazol-2-yl[2-(methylamino)-4-pyrimidinyl]acetonitrile
1,3-benzothiazol-2-yl(2-{4-[2-(4-morpholinyl)ethyl]-1-piperazinyl}-4-pyrimidinyl)-acetonitrile
1,3-benzothiazol-2-yl{2-[4-(benzyloxy)-1-piperidinyl]-4-pyrimidinyl}acetonitrile
1,3-benzothiazol-2-yl[2-(4-hydroxy-1-piperidinyl)-4-pyrimidinyl]acetonitrile
1,3-benzothiazol-2-yl(2-{[2-(dimethylamino)ethyl]amino}-4-pyrimidinyl)acetonitrile
1,3-benzothiazol-2-yl[2-(dimethylamino)-4-pyrimidinyl]acetonitrile
1,3-benzothiazol-2-yl{2-[(2-methoxyethyl)amino]-4-pyrimidinyl}acetonitrile
1,3-benzothiazol-2-yl{2-[(2-hydroxyethyl)amino]-4-pyrimidinyl}acetonitrile
1,3-benzothiazol-2-yl[2-(propylamino)-4-pyrimidinyl]acetonitrile
1,3-benzothiazol-2-yl(2-{[3-(1H-imidazol-1-yl)propyl]amino}-4-pyrimidinyl)acetonitrile
1,3-benzothiazol-2-yl[2-(1-pyrrolidinyl)-4-pyrimidinyl]acetonitrile
1,3-benzothiazol-2-yl{2-[(2-phenylethyl)amino]-4-pyrimidinyl}acetonitrile
1,3-benzothiazol-2-yl(2-{[2-(2-pyridinyl)ethyl]amino}-4-pyrimidinyl)acetonitrile
1,3-benzothiazol-2-yl {2-[(2-pyridinylmethyl)amino]-4-pyrimidinyl}acetonitrile
1,3-benzothiazol-2-yl {2-[4-(1H-1,2,3-benzotriazol-1-yl)-1-piperidinyl]-4-pyrimidinyl}acetonitrile
1,3-benzothiazol-2-yl {2-[4-(2-pyrazinyl)-1-piperazinyl]-4-pyrimidinyl}acetonitrile
1,3-benzothiazol-2-yl {2-[4-(2-pyrimidinyl)-1-piperazinyl]-4-pyrimidinyl}acetonitrile
1,3-benzothiazol-2-yl(2-{[2-(3-pyridinyl)ethyl]amino}-4-pyrimidinyl)acetonitrile
1,3-benzothiazol-2-yl(5-bromo-2-{[2-(dimethylamino)ethyl]amino}-4-pyrimidinyl)-acetonitrile
1,3-benzothiazol-2-yl {2-[(2-morpholin-4-ylethyl)amino]pyrimidin-4-yl}acetonitrile
1,3-benzothiazol-2-yl[2-(4-{3-[(trifluoromethyl)sulfonyl]anilino}piperidin-1-yl)pyrimidin-4-yl]acetonitrile
1,3-benzothiazol-2-yl(2-{[3-(2-oxopyrrolidin-1-yl)propyl]amino}pyrimidin-4-yl)-acetonitrile
1,3-benzothiazol-2-yl(2-{methyl[3-(methylamino)propyl]amino}pyrimidin-4-yl)acetonitrile
1,3-benzothiazol-2-yl(2-{[3-(4-methylpiperazin-1-yl)propyl]amino}pyrimidin-4-yl)-acetonitrile
1,3-benzothiazol-2-yl{2-[(3-morpholin-4-ylpropyl)amino]pyrimidin-4-yl}acetonitrile
1,3-benzothiazol-2-yl(2-{[2-(1-methyl-1H-imidazol-4-yl)ethyl]amino}pyrimidin-4-yl)acetonitrile
1,3-benzothiazol-2-yl(2-{[2-(1H-indol-3-yl)ethyl]amino}pyrimidin-4-yl)acetonitrile
1,3-benzothiazol-2-yl(2-{[2-(4-hydroxyphenyl)ethyl]amino}pyrimidin-4-yl)acetonitrile tert-butyl({4-[1,3-benzothiazol-2-yl(cyano)methyl]pyrimidin-2-yl}amino)acetate
{2-[(3-aminopropyl)amino]pyrimidin-4-yl}(1,3-benzothiazol-2-yl)acetonitrile
{2-[(2-aminoethyl)amino]pyrimidin-4-yl}(1,3-benzothiazol-2-yl)acetonitrile
1,3-benzothiazol-2-yl(2-{[3-(dimethylamino)propyl]amino}pyrimidin-4-yl)acetonitrile
1,3-benzothiazol-2-yl {2-[(2-piperidin-1-ylethyl)amino]pyrimidin-4-yl}acetonitrile
1,3-benzothiazol-2-yl(2-{[2-(1-methyl-1H-imidazol-5-yl)ethyl]amino}pyrimidin-4-yl)acetonitrile
1,3-benzothiazol-2-yl[2-(benzylamino)pyrimidin-4-yl]acetonitrile isopropyl 3-({4-[1,3-benzothiazol-2-yl(cyano)methyl]pyrimidin-2-yl}amino)propanoate
1,3-benzothiazol-2-yl {2-[(3-hydroxypropyl)amino]pyrimidin-4-yl}acetonitrile
1,3-benzothiazol-2-yl{2-[(pyridin-3-ylmethyl)amino]pyrimidin-4-yl}acetonitrile
1,3-benzothiazol-2-yl{2-[(pyridin-4-ylmethyl)amino]pyrimidin-4-yl}acetonitrile tert-butyl 4-[2-({4-[1,3-benzothiazol-2-yl(cyano)methyl]pyrimidin-2-yl}amino)-ethyl]phenylcarbamate
(2-{[2-(4-aminophenyl)ethyl]amino}pyrimidin-4-yl)(1,3-benzothiazol-2-yl)acetonitrile
1,3-benzothiazol-2-yl(2-{[2-(3,4-dimethoxyphenyl)ethyl]amino}pyrimidin-4-yl)acetonitrile
1,3-benzothiazol-2-yl(2-{[2-(3-methoxyphenyl)ethyl]amino}pyrimidin-4-yl)acetonitrile
1,3-benzothiazol-2-yl(2-{[2-(2-fluorophenyl)ethyl]amino}pyrimidin-4-yl)acetonitrile
1,3-benzothiazol-2-yl[2-({2-[3-(trifluoromethyl)phenyl]ethyl}amino)pyrimidin-4-yl]acetonitrile 1,3-benzothiazol-2-yl {2-[(2-hydroxy-2-phenylethyl)amino]pyrimidin-4-yl}acetonitrile
1,3-benzothiazol-2-yl {2-[(2-{[3-(trifluoromethyl)pyridin-2-yl]amino}ethyl)amino]-pyrimidin-4-yl}acetonitrile
1,3-benzothiazol-2-yl(2-{[2-(3-chlorophenyl)ethyl]amino}pyrimidin-4-yl)acetonitrile
1,3-benzothiazol-2-yl(2-{[2-(3,4-dichlorophenyl)ethyl]amino}pyrimidin-4-yl)acetonitrile
1,3-benzothiazol-2-yl(2-{[2-(4-methoxyphenyl)ethyl]amino}pyrimidin-4-yl)acetonitrile
1,3-benzothiazol-2-yl(2-{[2-(4-methylphenyl)ethyl]amino}pyrimidin-4-yl)acetonitrile
1,3-benzothiazol-2-yl(2-{[2-(3-fluorophenyl)ethyl]amino}pyrimidin-4-yl)acetonitrile
1,3-benzothiazol-2-yl(2-{[2-(4-phenoxyphenyl)ethyl]amino}pyrimidin-4-yl)acetonitrile
1,3-benzothiazol-2-yl(2-{[2-(2-phenoxyphenyl)ethyl]amino}pyrimidin-4-yl)acetonitrile
1,3-benzothiazol-2-yl(2-{[2-(4-bromophenyl)ethyl]amino}pyrimidin-4-yl)acetonitrile
1,3-benzothiazol-2-yl(2-{[2-(4-fluorophenyl)ethyl]amino}pyrimidin-4-yl)acetonitrile
1,3-benzothiazol-2-yl{2-[(2-[1,1'-biphenyl]-4-ylethyl)amino]pyrimidin-4-yl}acetonitrile
1,3-benzothiazol-2-yl {2-[(2-{4-[hydroxy(oxido)amino]phenyl}ethyl)amino]pyrimidin-4-yl}acetonitrile
1,3-benzothiazol-2-yl(2-{[2-(1H-1,2,4-triazol-1-yl)ethyl]amino}pyrimidin-4-yl)acetonitrile
1,3-benzothiazol-2-yl(2-{[3-(1H-pyrazol-1-yl)propyl]amino}pyrimidin-4-yl)acetonitrile
4-[2-({4-[1,3-benzothiazol-2-yl(cyano)methyl]pyrimidin-2-yl}amino)ethyl]benzene-sulfonamide
{2-[(2-pyridin-3-ylethyl)amino]pyrimidin-4-yl}[5-(trifluoromethyl)-1,3-benzothiazol-2-yl]acetonitrile
1,3-benzothiazol-2-yl{2-[(1H-tetrazol-5-ylmethyl)amino]pyrimidin-4-yl}acetonitrile
1,3-benzothiazol-2-yl[2-(benzyloxy)pyrimidin-4-yl]acetonitrile
1,3-benzothiazol-2-yl {2-[(4-pyridin-3-ylbenzyl)oxy]pyrimidin-4-yl}acetonitrile
1,3-benzothiazol-2-yl[2-(pyridin-4-ylmethoxy)pyrimidin-4-yl]acetonitrile
1,3-benzothiazol-2-yl[2-(pyridin-2-ylmethoxy)pyrimidin-4-yl]acetonitrile
1,3-benzothiazol-2-yl[2-(3-pyridin-2-ylpropoxy)pyrimidin-4-yl]acetonitrile
1,3-benzothiazol-2-yl{2-[(4-methoxybenzyl)oxy]pyrimidin-4-yl}acetonitrile
1,3-benzothiazol-2-yl[2-(pyridin-3-ylmethoxy)pyrimidin-4-yl]acetonitrile
1,3-benzothiazol-2-yl {2-[2-(4-methoxyphenyl)ethoxy]pyrimidin-4-yl}acetonitrile
1,3-benzothiazol-2-yl[2-([1,1'-biphenyl]-3-ylmethoxy)pyrimidin-4-yl]acetonitrile
1,3-benzothiazol-2-yl {2-[(3,4,5-trimethoxybenzyl)oxy]pyrimidin-4-yl}acetonitrile
1,3-benzothiazol-2-yl{2-[(3,4-dichlorobenzyl)oxy]pyrimidin-4-yl}acetonitrile
1,3-benzothiazol-2-yl[2-({3-[(dimethylamino)methyl]benzyl}oxy)pyrimidin-4-yl]acetonitrile
1,3-benzothiazol-2-yl{2-[(1-oxidopyridin-3-yl)methoxy]pyrimidin-4-yl}acetonitrile
1,3-benzothiazol-2-yl(2-{[4-(morpholin-4-ylmethyl)benzyl]oxy}pyrimidin-4-yl)acetonitrile
1,3-benzothiazol-2-yl {2-[(4-pyridin-2-ylbenzyl)oxy]pyrimidin-4-yl}acetonitrile
1,3-benzothiazol-2-yl(2-{[4-(piperidin-1-ylmethyl)benzyl]oxy}pyrimidin-4-yl)acetonitrile
1,3-benzothiazol-2-yl[2-(4-methoxyphenoxy)pyrimidin-4-yl]acetonitrile
1,3-benzothiazol-2-yl[2-(4-butoxyphenoxy)pyrimidin-4-yl]acetonitrile
{2-[4-(4-acetylpiperazin-1-yl)phenoxy]pyrimidin-4-yl}(1,3-benzothiazol-2-yl)acetonitrile
[2-(4-methoxyphenoxy)pyrimidin-4-yl][5-(trifluoromethyl)-1,3-benzothiazol-2-yl]acetonitrile
N-[2-({4-[1,3-benzothiazol-2-yl(cyano)methyl]pyrimidin-2-yl}amino)ethyl]-4-chlorobenzamide
1,3-benzothiazol-2-yl(2-methoxy-4-pyrimidinyl)acetonitrile
1,3-benzothiazol-2-yl[2-({4-[(4-methylpiperazin-1-yl)methyl]benzyl}oxy)pyrimidin-4-yl]acetonitrile
1,3-benzothiazol-2-yl[2-({4-[(4-benzyl-piperazin-1-yl)methyl]-benzyl}oxy)pyrimidin-4-yl]acetonitrile
1,3-benzothiazol-2-yl(2-{[4-(piperazin-1-ylmethyl)benzyl]oxy}pyrimidin-4-yl)acetonitrile
1,3-benzothiazol-2-yl[2-({4-[(4-formylpiperazin-1-yl)methyl]benzyl}oxy)pyrimidin-4-yl]acetonitrile
[2-({4-[(4-acetylpiperazin-1-yl)methyl]benzyl}oxy)pyrimidin-4-yl](1,3-benzothiazol-2-yl)acetonitrile
(3H-Benzothiazol-2-ylidene)-{2-[4-(4-[1,2,4]oxadiazol-3-ylmethyl-piperazin-1-ylmethyl)-benzyloxy]-pyrimidin-4-yl}-acetonitrile
4-(4-{4-[(3H-Benzothiazol-2-ylidene)-cyano-methyl]-pyrimidin-2-yloxymethyl}-benzyl)-piperazine-1-carboxylic acid methyl ester
2-[4-(4-{4-[(3H-Benzothiazol-2-ylidene)-cyano-methyl]-pyrimidin-2-yloxymethyl}-benzyl)-piperazin-1-yl]-acetamide
(2-{4-[4-(2-Amino-acetyl)-piperazin-1-ylmethyl]-benzyloxy}-pyrimidin-4-yl)-(3H-benzothiazol-2-ylidene)-acetonitrile
[4-(4-{4-[(3H-Benzothiazol-2-ylidene)-cyano-methyl]-pyrimidin-2-yloxymethyl}-benzyl)-piperazin-1-yl]-acetic acid methyl ester
(3H-Benzothiazol-2-ylidene)-(2-{4-[4-(2-methoxy-ethyl)-piperazin-1-ylmethyl]-benzyloxy}-pyrimidin-4-yl)-acetonitrile
4-(4-{4-[(3H-Benzothiazol-2-ylidene)-cyano-methyl]-pyrimidin-2-yloxymethyl}-benzyl)-piperazine-1-carboxylic acid dimethylamide
(3H-Benzothiazol-2-ylidene)-{2-[4-(4-ethyl-piperazin-1-ylmethyl)-benzyloxy]-pyrimidin-4-yl}-acetonitrile
(3H-Benzothiazol-2-ylidene)-(2-{4-[4-(2-hydroxy-ethyl)-piperazin-1-ylmethyl]-benzyloxy}-pyrimidin-4-yl)-acetonitrile The compounds of formula (I) may be obtained according to methods described in WO 01/47920.

In a further embodiment, the compounds of formula (I), are of sub-structure (II) and corresponding tautomers thereof.

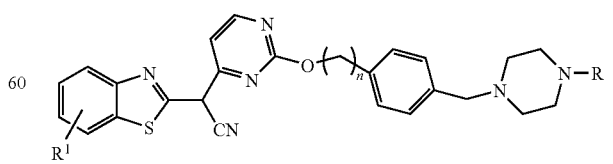

(II)

wherein R in formula (II) is selected from the group comprising or consisting of hydrogen, substituted or unsubstituted $C_1$-$C_6$-alkyl, substituted or unsubstituted $C_1$-$C_6$-alkyl aryl, substituted or unsubstituted heteroaryl, substituted or unsubstituted C₁-C₆-alkyl heteroaryl, substituted or unsubstituted C₂-C₆-alkenyl, substituted or unsubstituted C₂-C₆-alkenyl aryl, substituted or unsubstituted C₂-C₆-alkenyl heteroaryl, substituted or unsubstituted C₂-C₆-alkynyl, substituted or unsubstituted C₂-C₆-alkynyl aryl, substituted or unsubstituted C₂-C₆-alkynyl heteroaryl, substituted or unsubstituted C₃-C₈-cycloalkyl, substituted or unsubstituted heterocycloalkyl, substituted or unsubstituted C₁-C₆-alkyl cycloalkyl, substituted or unsubstituted C₁-C₆-alkyl heterocycloalkyl, substituted or unsubstituted C₁-C₆-alkyl carboxy, acyl, substituted or unsubstituted C₁-C₆-alkyl acyl, acyloxy, substituted or unsubstituted C₁-C₆-alkyl acyloxy, substituted or unsubstituted C₁-C₆-alkyl alkoxy, alkoxycarbonyl, substituted or unsubstituted C₁-C₆-alkyl alkoxycarbonyl, aminocarbonyl, substituted or unsubstituted C₁-C₆-alkyl aminocarbonyl, acylamino, substituted or unsubstituted C₁-C₆-alkyl acylamino, ureido, substituted or unsubstituted C₁-C₆-alkyl ureido, amino, substituted or unsubstituted C₁-C₆-alkyl amino, sulfonyloxy, substituted or unsubstituted C₁-C₆-alkyl sulfonyloxy, sulfonyl, substituted or unsubstituted C₁-C₆-alkyl sulfonyl, sulfinyl, substituted or unsubstituted C₁-C₆-alkyl sulfinyl, sulfanyl, substituted or unsubstituted C₁-C₆-alkyl sulfanyl, sulfonylamino, substituted or unsubstituted C₁-C₆-alkyl sulfonylamino.

$R^1$ is selected from the group comprising or consisting of H, halogen, cyano, nitro, amino, substituted or unsubstituted C₁-C₆-alkyl, in particular C₁-C₃ alkyl, like methyl or ethyl or —CF₃, substituted or unsubstituted C₂-C₆-alkenyl, substituted or unsubstituted C₂-C₆-alkynyl, substituted or unsubstituted C₁-C₆-alkyl-aryl, substituted or unsubstituted aryl or substituted or unsubstituted heteroaryl, substituted or unsubstituted C₁-C₆-alkyl-heteroaryl, —C(O)—OR², —C(O)—R², —C(O)—NR²R²', —(SO₂)R², with $R^2$ and $R^{2'}$ being independently selected from the group comprising or consisting of hydrogen, unsubstituted or substituted C₁-C₆ alkyl, unsubstituted or substituted C₂-C₆ alkenyl, unsubstituted or substituted C₂-C₆ alkynyl, unsubstituted or substituted aryl, unsubstituted or substituted heteroaryl, unsubstituted or substituted C₁-C₆-alkyl aryl, unsubstituted or substituted C₁-C₆-alkyl heteroaryl. Preferably $R^1$ is H n is an integer from 0 to 3, more preferred is 1.

Specific piperazine benzothiazole derivatives according to the present invention are selected from the following group:

1,3-benzothiazol-2-yl[2-({4-[(4-methylpiperazin-1-yl)methyl]benzyl}oxy)pyrimidin-4-yl]acetonitrile
1,3-benzothiazol-2-yl[2-({4-[(4-benzyl-piperazin-1-yl)methyl]-benzyl}oxy)pyrimidin-4-yl]acetonitrile
1,3-benzothiazol-2-yl(2-{[4-(piperazin-1-ylmethyl)benzyl]oxy}pyrimidin-4-yl)acetonitrile
1,3-benzothiazol-2-yl[2-({4-[(4-formylpiperazin-1-yl)methyl]benzyl}oxy)pyrimidin-4-yl]acetonitrile
[2-({4-[(4-acetylpiperazin-1-yl)methyl]benzyl}oxy)pyrimidin-4-yl](1,3-benzothiazol-2-yl)acetonitrile
(3H-Benzothiazol-2-ylidene)-{2-[4-(4-[1,2,4]oxadiazol-3-ylmethyl-piperazin-1-ylmethyl)-benzyloxy]-pyrimidin-4-yl}-acetonitrile
4-(4-{4-[(3H-Benzothiazol-2-ylidene)-cyano-methyl]-pyrimidin-2-yloxymethyl}-benzyl)-piperazine-1-carboxylic acid methyl ester
2-[4-(4-{4-[(3H-Benzothiazol-2-ylidene)-cyano-methyl]-pyrimidin-2-yloxymethyl}-benzyl)-piperazin-1-yl]-acetamide
(2-{4-[4-(2-Amino-acetyl)-piperazin-1-ylmethyl]-benzyloxy}-pyrimidin-4-yl)-(3H-benzothiazol-2-ylidene)-acetonitrile
[4-(4-{4-[(3H-Benzothiazol-2-ylidene)-cyano-methyl]-pyrimidin-2-yloxymethyl}-benzyl)-piperazin-1-yl]-acetic acid methyl ester
(3H-Benzothiazol-2-ylidene)-(2-{4-[4-(2-methoxy-ethyl)-piperazin-1-ylmethyl]-benzyloxy}-pyrimidin-4-yl)-acetonitrile
4-(4-{4-[(3H-Benzothiazol-2-ylidene)-cyano-methyl]-pyrimidin-2-yloxymethyl}-benzyl)-piperazine-1-carboxylic acid dimethylamide
(3H-Benzothiazol-2-ylidene)-{2-[4-(4-ethyl-piperazin-1-ylmethyl)-benzyloxy]-pyrimidin-4-yl}-acetonitrile
(3H-Benzothiazol-2-ylidene)-(2-{4-[4-(2-hydroxy-ethyl)-piperazin-1-ylmethyl]-benzyloxy}-pyrimidin-4-yl)-acetonitrile.

The compounds of formula (II) may be obtained according to the methods described in WO 03/091249.

In a further embodiment the JNK inhibitors may have the formula (III):

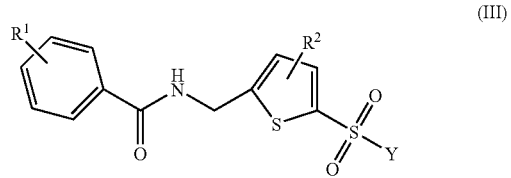

(III)

Y is an unsubstituted or a substituted 4-12-membered saturated cyclic or bicyclic alkyl ring containing at least one nitrogen atom (heterocycle), whereby one nitrogen atom within said ring is forming a bond with the sulfonyl group of formula III, thus providing a sulfonamide.

$R^1$ is selected from the group comprising or consisting of hydrogen, unsubstituted or a substituted C₁-C₆-alkoxy, unsubstituted or a substituted C₁-C₆-alkyl, unsubstituted or a substituted C₂-C₆-alkenyl, unsubstituted or a substituted C₂-C₆-alkynyl, amino, sulfanyl, sulfinyl, sulfonyl, sulfonyloxy, sulfonamide, acylamino, aminocarbonyl, unsubstituted or a substituted C₁-C₆ alkoxycarbonyl, unsubstituted or a substituted aryl, unsubstituted or a substituted heteroaryl, carboxy, cyano, halogen, hydroxy, nitro, hydrazide.

More specifically, $R^1$ is selected from the group consisting of hydrogen, halogen (e.g. chlorine), C₁-C₆ alkyl (e.g. methyl or ethyl) or C₁-C₆ alkoxy (e.g. methoxy or ethoxy). Most preferred is halogen, in particular chlorine.

$R^2$ is selected from the group comprising or consisting of hydrogen, COOR³, —CONR³R³', OH, a C₁-C₄ alkyl substituted with an OH or amino group, a hydrazido carbonyl group, a sulfate, a sulfonate, an amine or an ammonium salt. Thereby, $R^3$, $R^{3'}$ are independently selected from the group consisting of H, C₁-C₆-alkyl, C₂-C₆-alkenyl, aryl, heteroaryl, aryl-C₁-C₆-alkyl, heteroaryl-C₁-C₆-alkyl.

According to one embodiment the cyclic amines Y have either of the general formulae (a) to (d):

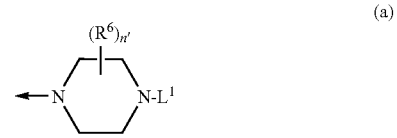

(a)

-continued

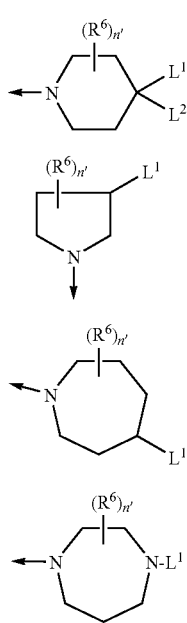

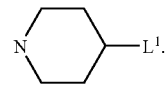

$L^1$ is —$NHR^3$; where $R^3$ is a straight or branched $C_4$-$C_{12}$-alkyl, preferably a $C_8$-$C_{12}$-alkyl, or a benzyl group.

Specific examples of compounds of formula (III) include the following:

4-chloro-N-[5-(piperazine-1-sulfonyl)-thiophen-2-yl-methyl]-benzamide

4-Chloro-N-{5-[4-(3-trifluoromethanesulfonyl-phenylamino)-piperidine-1-sulfonyl]-thiophen-2-ylmethyl}-benzamide 4-chloro-N-({5-[(4-pyridin-2-ylpiperazin-1-yl)sulfonyl]thien-2-yl}methyl)benzamide 4-chloro-N-[(5-{[4-(4-fluorobenzoyl)piperidin-1-yl]sulfonyl}thien-2-yl)methyl]benzamide 4-chloro-N-{[5-({4-[4-(trifluoromethyl)phenyl]piperazin-1-yl}sulfonyl)thien-2-yl]methyl}benzamide 4-chloro-N-({5-[(4-{2-nitrophenyl}piperazin-1-yl)sulfonyl]thien-2-yl}methyl)benzamide 4-chloro-N-({5-[(4-{4-nitrophenyl}piperazin-1-yl)sulfonyl]thien-2-yl}methyl)benzamide 4-chloro-N-[(5-{[4-(2-furoyl)piperazin-1-yl]sulfonyl}thien-2-yl)methyl]benzamide 4-chloro-N-[(5-{[4-(4-hydroxyphenyl)piperazin-1-yl]sulfonyl}thien-2-yl)methyl]benzamide 4-chloro-N-[(5-{[4-(2-oxo-2-pyrrolidin-1-ylethyl)piperazin-1-yl]sulfonyl}thien-2-yl)methyl]benzamide 4-chloro-N-[(5-{[4-(2-morpholin-4-yl-2-oxoethyl)piperazin-1-yl]sulfonyl}thien-2-yl)methyl]benzamide 4-chloro-N-[(5-{[4-(pyridin-4-ylmethyl)piperazin-1-yl]sulfonyl}thien-2-yl)methyl]benzamide 4-chloro-N-[(5-{[4-(2-thien-2-ylethyl)piperazin-1-yl]sulfonyl}thien-2-yl)methyl]benzamide 4-chloro-N-[(5-{[4-(3,5-dimethoxyphenyl)piperazin-1-yl]sulfonyl}thien-2-yl)methyl]benzamide 4-chloro-N-[(5-{[4-(cyclohexylmethyl)piperazin-1-yl]sulfonyl}thien-2-yl)methyl]benzamide 4-chloro-N-[(5-{[4-(2-methoxyphenyl)piperazin-1-yl]sulfonyl}thien-2-yl)methyl]benzamide N-({5-[(4-benzylpiperazin-1-yl)sulfonyl]thien-2-yl}methyl)-4-chlorobenzamide 4-chloro-N-[(5-{[4-(2-phenylethyl)piperazin-1-yl]sulfonyl}thien-2-yl)methyl]benzamide 4-chloro-N-[(5-{[4-(4-fluorobenzyl)piperazin-1-yl]sulfonyl}thien-2-yl)methyl]benzamide 4-chloro-N-[(5-{[4-(2-cyanophenyl)piperazin-1-yl]sulfonyl}thien-2-yl)methyl]benzamide 4-chloro-N-{[5-({4-[4-chloro-3-(trifluoromethyl)phenyl]piperazin-1-yl}sulfonyl)thien-2-yl]methyl}benzamide 4-chloro-N-[(5-{[4-(3-piperidin-1-ylpropyl)piperazin-1-yl]sulfonyl}thien-2-yl)methyl]benzamide 4-chloro-N-({5-[(4-{4-chloro-2-nitrophenyl}piperazin-1-yl)sulfonyl]thien-2-yl}methyl)benzamide 4-chloro-N-[(5-{[4-(6-methylpyridin-2-yl)piperazin-1-yl]sulfonyl}thien-2-yl)methyl]benzamide 4-chloro-N-({5-[(4-hydroxy-4-phenylpiperidin-1-yl)sulfonyl]thien-2-yl}methyl)benzamide N-({5-[(4-benzoylpiperidin-1-yl)sulfonyl]thien-2-yl}methyl)-4-chlorobenzamide 4-chloro-N-[(5-{[4-(2-oxo-2,3-dihydro-1H-benzimidazol-1-yl)piperidin-1-yl]sulfonyl}thien-2-yl)methyl]benzamide Thereby, $L^1$ and $L^2$ are independently selected from each other from the group consisting of unsubstituted or a substituted $C_1$-$C_6$-alkyl, unsubstituted or a substituted $C_2$-$C_6$-alkenyl, unsubstituted or a substituted $C_2$-$C_6$-alkynyl, unsubstituted or a substituted $C_4$-$C_8$-cycloalkyl optionally containing 1-3 heteroatoms and optionally fused with aryl or heteroaryl.

Alternatively, $L^1$ and $L^2$ are independently selected from the group consisting of unsubstituted or a substituted aryl, unsubstituted or a substituted heteroaryl, unsubstituted or a substituted aryl-$C_1$-$C_6$-alkyl, unsubstituted or a substituted heteroaryl-$C_1$-$C_6$-alkyl, —C(O)—$OR^3$, —C(O)—$R^3$, —C(O)—$NR^{3'}R^3$, —$NR^{3'}R^3$, —$NR^{3'}C(O)R^3$, —$NR^{3'}C(O)NR^{3'}R^3$, —(SO)$R^3$, —(SO$_2$)$R^3$, —$NSO_2R^3$, —$SO_2NR^{3'}R^3$.

Alternatively, $L^1$ and $L^2$ taken together may form a 4-8-membered, unsubstituted or a substituted saturated cyclic alkyl or heteroalkyl ring.

$R^3$, $R^{3'}$ are independently selected from the group consisting of H, unsubstituted or a substituted $C_1$-$C_6$-alkyl, unsubstituted or a substituted $C_2$-$C_6$-alkenyl, unsubstituted or a substituted aryl, unsubstituted or a substituted heteroaryl, unsubstituted or a substituted aryl-$C_1$-$C_6$-alkyl, unsubstituted or a substituted heteroaryl-$C_1$-$C_6$-alkyl.

$R^6$ is selected from the group consisting of hydrogen, unsubstituted or a substituted $C_1$-$C_6$-alkyl, $C_1$-$C_6$-alkoxy, OH, halogen, nitro, cyano, sulfonyl, oxo (=O), and n' is an integer from 0 to 4, preferably 1 or 2. In one embodiment $R^6$ is hydrogen.

In a further specific embodiment $R^6$ is H, $L^2$ is H, $L^1$ is —$NR^{3'}R^3$; where at least one of $R^{3'}$ and $R^3$ is not hydrogen, but a substituent selected from the group consisting of straight or branched $C_4$-$C_{18}$-alkyl, aryl-$C_1$-$C_{18}$-alkyl, heteroaryl-$C_2$-$C_{18}$-alkyl, $C_1$-$C_{14}$-alkyl substituted with a $C_3$-$C_{12}$-cycloalkyl or -bicyclo or -tricyloalkyl, and whereby said alkyl chain may contain 1-3 O or S atoms.

In a more specific embodiment $L^1$ is —$NHR^3$; where $R^3$ is a straight or branched $C_4$-$C_{12}$-alkyl, preferably a $C_6$-$C_{12}$-alkyl, optionally substituted with a cyclohexyl group or a benzyl group.

In an even more specific embodiment Y is a piperidine group

N-({5-[(4-benzylpiperidin-1-yl)sulfonyl]thien-2-yl}methyl)-4-chlorobenzamide
4-chloro-N-({5-[(4-oxo-1-phenyl-1,3,8-triazaspiro[4.5]dec-8-yl)sulfonyl]thien-2-yl}methyl)benzamide
4-chloro-N-{[5-({4-[2-(methylanilino)-2-oxoethyl]piperazin-1-yl}sulfonyl)thien-2-yl]methyl}benzamide
4-chloro-N-{[5-({4-[hydroxy(diphenyl)methyl]piperidin-1-yl}sulfonyl)thien-2-yl]methyl}benzamide
4-chloro-N-[(5-{[4-(3-cyanopyrazin-2-yl)piperazin-1-yl]sulfonyl}thien-2-yl)methyl]benzamide
4-chloro-N-({5-[(4-{5-nitropyridin-2-yl}piperazin-1-yl)sulfonyl]thien-2-yl}methyl)benzamide
4-chloro-N-{[5-({4-[3-chloro-5-(trifluoromethyl)pyridin-2-yl]piperazin-1-yl}sulfonyl)thien-2-yl]methyl}benzamide
4-chloro-N-{[5-({4-[5-(trifluoromethyl)pyridin-2-yl]piperazin-1-yl}sulfonyl)thien-2-yl]methyl}benzamide
4-chloro-N-{[5-({4-[3-(trifluoromethyl)pyridin-2-yl]piperazin-1-yl}sulfonyl)thien-2-yl]methyl}benzamide
4-chloro-N-[(5-{[4-(2,4-difluorobenzoyl)piperidin-1-yl]sulfonyl}thien-2-yl)methyl]benzamide
methyl 5-{4-[(5-{[(4-chlorobenzoyl)amino]methyl}thien-2-yl)sulfonyl]piperazin-1-yl}-7-(trifluoromethyl)thieno[3,2-b]pyridine-3-carboxylate
ethyl 2-{4-[(5-{[(4-chlorobenzoyl)amino]methyl}thien-2-yl)sulfonyl]piperazin-1-yl}-5-cyano-6-methylnicotinate
4-chloro-N-{[5-({4-[5-cyano-4,6-bis(dimethylamino)pyridin-2-yl]piperazin-1-yl}sulfonyl)thien-2-yl]methyl}benzamide
4-chloro-N-{[5-({4-[6-methyl-2-(trifluoromethyl)quinolin-4-yl]piperazin-1-yl}sulfonyl)thien-2-yl]methyl}benzamide
tert-butyl 4-[(5-{[(4-chlorobenzoyl)amino]methyl}thien-2-yl)sulfonyl]piperazine-1-carboxylate
2-{4-[(5-{[(4-chlorobenzoyl)amino]methyl}thien-2-yl)sulfonyl]piperazin-1-yl}-8-ethyl-5-oxo-5,8-dihydropyrido[2,3-d]pyrimidine-6-carboxylic acid
7-{4-[(5-{[(4-chlorobenzoyl)amino]methyl}thien-2-yl)sulfonyl]piperazin-1-yl}-1-ethyl-6-fluoro-4-oxo-1,4-dihydro[1,8]naphthyridine-3-carboxylic acid
7-{4-[(5-{[(4-chlorobenzoyl)amino]methyl}thien-2-yl)sulfonyl]piperazin-1-yl}-1-ethyl-6-fluoro-4-oxo-1,4-dihydroquinoline-3-carboxylic acid
4-chloro-N-[(5-{[4-(2,3-dihydro-1,4-benzodioxin-2-ylcarbonyl)piperazin-1-yl]sulfonyl}thien-2-yl)methyl]benzamide
4-chloro-N-{[5-({4-[(2E)-3-phenylprop-2-enyl]piperazin-1-yl}sulfonyl)thien-2-yl]methyl}benzamide
4-chloro-N-[(5-{[4-(3-phenylpropyl)piperazin-1-yl]sulfonyl}thien-2-yl)methyl]benzamide
4-chloro-N-[(5-{[4-(3,4,5-trimethoxyphenyl)piperazin-1-yl]sulfonyl}thien-2-yl)methyl]benzamide
N-[(5-{[4-(4-tert-butylbenzyl)piperazin-1-yl]sulfonyl}thien-2-yl)methyl]-4-chlorobenzamide
4-chloro-N-[(5-{[4-(4-fluorophenyl)piperazin-1-yl]sulfonyl}thien-2-yl)methyl]benzamide
4-chloro-N-[(5-{[4-(2-hydroxyphenyl)piperazin-1-yl]sulfonyl}thien-2-yl)methyl]benzamide
4-chloro-N-{[5-({4-[4-(trifluoromethyl)pyridin-2-yl]piperazin-1-yl}sulfonyl)thien-2-yl]methyl}benzamide
4-chloro-N-[(5-{[4-(5-cyanopyridin-2-yl)piperazin-1-yl]sulfonyl}thien-2-yl)methyl]benzamide
tert-butyl 1-[(5-{[(4-chlorobenzoyl)amino]methyl}thien-2-yl)sulfonyl]piperidin-4-ylcarbamate
4-chloro-N-({5-[(4-phenylpiperazin-1-yl)sulfonyl]thien-2-yl}methyl)benzamide
4-chloro-N-{[5-(piperidin-1-ylsulfonyl)thien-2-yl]methyl}benzamide
4-chloro-N-[(5-{[4-(1-naphthyl)piperazin-1-yl]sulfonyl}thien-2-yl)methyl]benzamide
4-chloro-N-[(5-{[4-(3,4-dichlorophenyl)piperazin-1-yl]sulfonyl}thien-2-yl)methyl]benzamide
4-chloro-N-{[5-({4-[3-(trifluoromethyl)phenyl]piperazin-1-yl}sulfonyl)thien-2-yl]methyl}benzamide
4-chloro-N-{[5-({3-hydroxy-4-[3-(trifluoromethyl)phenyl]piperidin-1-yl}sulfonyl)thien-2-yl]methyl}benzamide
4-chloro-N-[(5-{[4-(2-methylphenyl)piperazin-1-yl]sulfonyl}thien-2-yl)methyl]benzamide
N-[(5-{[(1R,4R)-5-benzyl-2,5-diazabicyclo[2.2.1]hept-2-yl]sulfonyl}thien-2-yl)methyl]-4-chlorobenzamide
N-[(5-{[4-(benzyloxy)piperidin-1-yl]sulfonyl}thien-2-yl)methyl]-4-chlorobenzamide
4-chloro-N-[(5-{[4-(2-chlorodibenzo[b,f][1,4]oxazepin-11-yl)piperazin-1-yl]sulfonyl}thien-2-yl)methyl]benzamide
N-(4-chlorophenyl)-2-(5-{[4-(2-oxo-2,3-dihydro-1H-benzimidazol-1-yl)piperidin-1-yl]sulfonyl}thien-2-yl)acetamide
4-chloro-N-({5-[(4-hydroxypiperidin-1-yl)sulfonyl]thien-2-yl}methyl)benzamide
N-[(5-{[4-(4-acetylphenyl)piperazin-1-yl]sulfonyl}thien-2-yl)methyl]-4-chlorobenzamide
4-chloro-N-[(5-{[4-(3,5-dichloropyridin-4-yl)piperazin-1-yl]sulfonyl}thien-2-yl)methyl]benzamide
4-chloro-N-[(5-{[4-(3-methoxyphenyl)piperazin-1-yl]sulfonyl}thien-2-yl)methyl]benzamide
N-({5-[(4-benzyl-4-hydroxypiperidin-1-yl)sulfonyl]thien-2-yl}methyl)-4-chlorobenzamide
N-{[5-({4-[(2-tert-butyl-1H-indol-5-yl)amino]piperidin-1-yl}sulfonyl)thien-2-yl]methyl}-4-chlorobenzamide
4-chloro-N-{[5-({4-[(phenylacetyl)amino]piperidin-1-yl}sulfonyl)thien-2-yl]methyl}benzamide
4-chloro-N-[(5-{[4-(tetrahydrofuran-2-ylcarbonyl)piperazin-1-yl]sulfonyl}thien-2-yl)methyl]benzamide
4-chloro-N-[(5-{[4-(6-chloropyridin-2-yl)piperazin-1-yl]sulfonyl}thien-2-yl)methyl]benzamide
4-chloro-N-[(5-{[4-(4-chlorophenyl)piperazin-1-yl]sulfonyl}thien-2-yl)methyl]benzamide
N-[(5-{[4-(2H-1,2,3-benzotriazol-2-yl)piperidin-1-yl]sulfonyl}thien-2-yl)methyl]-4-chlorobenzamide
4-chloro-N-[(5-{[4-(4-chlorobenzoyl)piperidin-1-yl]sulfonyl}thien-2-yl)methyl]benzamide
4-chloro-N-({5-[(4-phenoxypiperidin-1-yl)sulfonyl]thien-2-yl}methyl)benzamide
N-{[5-({4-[benzyl(methyl)amino]piperidin-1-yl}sulfonyl)thien-2-yl]methyl}-4-chlorobenzamide
4-chloro-N-{[5-({4-[3-(2,4-dichlorophenyl)-1H-pyrazol-5-yl]piperidin-1-yl}sulfonyl)thien-2-yl]methyl}benzamide
4-chloro-N-[(5-{[4-(5-thien-2-yl-1H-pyrazol-3-yl)piperidin-1-yl]sulfonyl}thien-2-yl)methyl]benzamide
4-chloro-N-[(5-{[4-(2,3,4,5,6-pentamethylbenzoyl)piperidin-1-yl]sulfonyl}thien-2-yl)methyl]benzamide
4-chloro-N-[(5-{[4-(phenylacetyl)-1,4-diazepan-1-yl]sulfonyl}thien-2-yl)methyl]benzamide
4-chloro-N-{[5-({4-[5-(4-methoxyphenyl)-1H-pyrazol-3-yl]piperidin-1-yl}sulfonyl)thien-2-yl]methyl}benzamide
N-({5-[(4-anilinopiperidin-1-yl)sulfonyl]thien-2-yl}methyl)-4-chlorobenzamide
4-chloro-N-[(5-{[4-(3-phenyl-1,2,4-thiadiazol-5-yl)piperazin-1-yl]sulfonyl}thien-2-yl)methyl]benzamide
4-chloro-N-[(5-{[4-(2-phenylethyl)piperidin-1-yl]sulfonyl}thien-2-yl)methyl]benzamide
4-chloro-N-({5-[(4-heptylpiperazin-1-yl)sulfonyl]thien-2-yl}methyl)benzamide
4-chloro-N-({5-[(4-octylpiperazin-1-yl)sulfonyl]thien-2-yl}methyl)benzamide N-[(5-{[4-(1H-1,2,3-benzotriazol-1-yl)piperidin-1-yl]sulfonyl}thien-2-yl)methyl]-4-chlorobenzamide
2-(5-{[4-(1H-1,2,3-benzotriazol-1-yl)piperidin-1-yl]sulfonyl}thien-2-yl)-N-(4-chlorophenyl)acetamide
2-{1-[(5-{[(4-chlorobenzoyl)amino]methyl}thien-2-yl)sulfonyl]piperidin-4-yl}-2H-1,2,3-benzotriazole-5-carboxylic acid
4-chloro-N-[(5-{[4-(5-chloro-1H-1,2,3-benzotriazol-1-yl)piperidin-1-yl]sulfonyl}thien-2-yl)methyl]benzamide
methyl 1-{1-[(5-{[(4-chlorobenzoyl)amino]methyl}thien-2-yl)sulfonyl]piperidin-4-yl}-1H-1,2,3-benzotriazole-5-carboxylate
methyl 1-{1-[(5-{[(4-chlorobenzoyl)amino]methyl}thien-2-yl)sulfonyl]piperidin-4-yl}-1H-1,2,3-benzotriazole-6-carboxylate
methyl 2-{1-[(5-{[(4-chlorobenzoyl)amino]methyl}thien-2-yl)sulfonyl]piperidin-4-yl}-2H-1,2,3-benzotriazole-5-carboxylate
4-chloro-N-[(5-{[4-(6-chloro-1H-1,2,3-benzotriazol-1-yl)piperidin-1-yl]sulfonyl}thien-2-yl)methyl]benzamide
4-chloro-N-{[5-({4-[5-(trifluoromethyl)-1H-1,2,3-benzotriazol-1-yl]piperidin-1-yl}sulfonyl)thien-2-yl]methyl}benzamide
N-[(5-{[4-(7-aza-1H-benzimidazol-1-yl)piperidin-1-yl]sulfonyl}thien-2-yl)methyl]-4-chlorobenzamide
1-{1-[(5-{[(4-chlorobenzoyl)amino]methyl}thien-2-yl)sulfonyl]piperidin-4-yl}-1H-1,2,3-benzotriazole-5-carboxylic acid
1-{1-[(5-{[(4-chlorobenzoyl)amino]methyl}thien-2-yl)sulfonyl]piperidin-4-yl}-1H-1,2,3-benzotriazole-6-carboxylic acid
N-[(5-{[4-(2-amino-9H-purin-9-yl)piperidin-1-yl]sulfonyl}thien-2-yl)methyl]-4-chlorobenzamide
4-chloro-N-[(5-{[4-(9H-purin-9-yl)piperidin-1-yl]sulfonyl}thien-2-yl)methyl]benzamide
N-[(5-{[4-(6-amino-9H-purin-9-yl)piperidin-1-yl]sulfonyl}thien-2-yl)methyl]-4-chlorobenzamide
4-chloro-N-({5-[(4-{6-nitro-1H-benzimidazol-1-yl}piperidin-1-yl)sulfonyl]thien-2-yl}methyl)benzamide
4-chloro-N-({5-[(4-{5-nitro-1H-benzimidazol-1-yl}piperidin-1-yl)sulfonyl]thien-2-yl}methyl)benzamide
4-chloro-N-[(5-{[4-(2H-1,2,3-triazol-2-yl)piperidin-1-yl]sulfonyl}thien-2-yl)methyl]benzamide
N-[(5-{[4-(1H-benzimidazol-1-yl)piperidin-1-yl]sulfonyl}thien-2-yl)methyl]-4-chlorobenzamide
4-chloro-N-{[5-({4-[3-propylanilino]piperidin-1-yl}sulfonyl)thien-2-yl]methyl}benzamide
4-chloro-N-{[5-({4-[3-(trifluoromethyl)anilino]piperidin-1-yl}sulfonyl)thien-2-yl]methyl}benzamide
4-chloro-N-{[5-({4-[3-(dimethylamino)anilino]piperidin-1-yl}sulfonyl)thien-2-yl]methyl}benzamide
methyl 3-({1-[(5-{[(4-chlorobenzoyl)amino]-methyl}thien-2-yl)sulfonyl]-piperidin-4-yl}amino)-benzoate
4-chloro-N-{[5-({4-[3-(methylsulfanyl)anilino]piperidin-1-yl}sulfonyl)thien-2-yl]methyl}benzamide
4-chloro-N-({5-[(4-{3-nitroanilino}piperidin-1-yl)sulfonyl]thien-2-yl}methyl)benzamide
4-chloro-N-[(5-{[4-(2-methoxyanilino)piperidin-1-yl]sulfonyl}thien-2-yl)methyl]benzamide
3-({1-[(5-{[(4-chlorobenzoyl)amino]methyl}thien-2-yl)sulfonyl]piperidin-4-yl}amino)benzamide
4-chloro-N-{[5-({4-[2-(trifluoromethyl)anilino]piperidin-1-yl}sulfonyl)thien-2-yl]methyl}benzamide
4-chloro-N-({5-[(4-{2-nitro-4-[(trifluoromethyl)sulfonyl]anilino}piperidin-1-yl)sulfonyl]thien-2-yl}methyl)benzamide
4-chloro-N-[(5-{[4-(4-chloroanilino)piperidin-1-yl]sulfonyl}thien-2-yl)methyl]benzamide
4-chloro-N-{[5-({4-[4-(trifluoromethyl)anilino]piperidin-1-yl}sulfonyl)thien-2-yl]methyl}benzamide
4-chloro-N-({5-[(4-{4-[(trifluoromethyl)sulfonyl]anilino}piperidin-1-yl)sulfonyl]thien-2-yl}methyl)benzamide
4-chloro-N-({5-[(4-{2-nitroanilino}piperidin-1-yl)sulfonyl]thien-2-yl}methyl)benzamide
N-{[5-({4-[4-(aminocarbonyl)anilino]piperidin-1-yl}sulfonyl)thien-2-yl]methyl}-4-chlorobenzamide
4-chloro-N-{[5-({4-[4-(1,3-dithiolan-2-yl)anilino]piperidin-1-yl}sulfonyl)thien-2-yl]methyl}benzamide
N-[(5-{[4-(3-chloroanilino)piperidin-1-yl]sulfonyl}thien-2-yl)methyl]-3-nitrobenzamide
4-chloro-N-[(5-{[4-(3-chloroanilino)piperidin-1-yl]sulfonyl}thien-2-yl)methyl]benzamide
4-chloro-N-[(5-{[4-(3-methoxyanilino)piperidin-1-yl]sulfonyl}thien-2-yl)methyl]benzamide
4-chloro-N-{[5-({4-[3-(methylsulfonyl)anilino]piperidin-1-yl}sulfonyl)thien-2-yl]methyl}benzamide
N-({5-[(4-{3-[amino(imino)methyl]anilino}piperidin-1-yl)sulfonyl]thien-2-yl}methyl)-4-chlorobenzamide
4-chloro-N-({5-[(4-{3-[(2-hydroxyethyl)sulfonyl]anilino}piperidin-1-yl)sulfonyl]thien-2-yl}methyl)benzamide
N-[(5-{[4-(2-aminoanilino)piperidin-1-yl]sulfonyl}thien-2-yl)methyl]-4-chlorobenzamide
4-chloro-N-[(5-{[4-(2-hydroxyanilino)piperidin-1-yl]sulfonyl}thien-2-yl)methyl]benzamide
4-chloro-N-[(5-{[4-(4-hydroxyanilino)piperidin-1-yl]sulfonyl}thien-2-yl)methyl]benzamide
4-chloro-N-({5-[(4-{3-[(trifluoromethyl)sulfanyl]anilino}piperidin-1-yl)sulfonyl]thien-2-yl}methyl)benzamide
4-chloro-N-[(5-{[4-(3-toluidino)piperidin-1-yl]sulfonyl}thien-2-yl)methyl]benzamide
4-chloro-N-({5-[(4-{[3-chloro-5-(trifluoromethyl)pyridin-2-yl]amino}piperidin-1-yl)sulfonyl]thien-2-yl}methyl)benzamide
4-chloro-N-{[5-({4-[3-(1,3-oxazol-5-yl)anilino]piperidin-1-yl}sulfonyl)thien-2-yl]methyl}benzamide
N-[(5-{[4-(3-tert-butylanilino)piperidin-1-yl]sulfonyl}thien-2-yl)methyl]-4-chlorobenzamide
4-chloro-N-[(5-{[4-(2-propylanilino)piperidin-1-yl]sulfonyl}thien-2-yl)methyl]benzamide
4-chloro-N-{[5-({4-[(2,2-dioxido-1,3-dihydro-2-benzothien-5-yl)amino]piperidin-1-yl}sulfonyl)thien-2-yl]methyl}benzamide
4-chloro-N-[(5-{[4-(2,3-dihydro-1H-inden-5-ylamino)piperidin-1-yl]sulfonyl}thien-2-yl)methyl]benzamide
4-chloro-N-[(5-{[4-(4-propylanilino)piperidin-1-yl]sulfonyl}thien-2-yl)methyl]benzamide
4-chloro-N-[(5-{[4-({3-nitropyridin-2-yl}amino)piperidin-1-yl]sulfonyl}thien-2-yl)methyl]benzamide
N-{[5-({4-[(3-aminopyridin-2-yl)amino]piperidin-1-yl}sulfonyl)thien-2-yl]methyl}-4-chlorobenzamide
N-[(5-{[4-([1,1'-biphenyl]-3-ylamino)piperidin-1-yl]sulfonyl}thien-2-yl)methyl]-4-chlorobenzamide
N-[(5-{[4-(3-benzylanilino)piperidin-1-yl]sulfonyl}thien-2-yl)methyl]-4-chlorobenzamide
4-chloro-N-[(5-{[4-(pyrimidin-2-ylamino)piperidin-1-yl]sulfonyl}thien-2-yl)methyl]benzamide
4-chloro-N-{[5-({4-[4-(morpholin-4-ylsulfonyl)anilino]piperidin-1-yl}sulfonyl)thien-2-yl]methyl}benzamide 4-chloro-N-({5-[(4-{[4-(trifluoromethyl)pyrimidin-2-yl]amino}piperidin-1-yl)sulfonyl]thien-2-yl}methyl)benzamide
4-chloro-N-[(5-{[4-(3-cyclohexyl-4-hydroxyanilino)piperidin-1-yl]sulfonyl}thien-2-yl)methyl]benzamide
N-({5-[(4-{3-[(butylamino)sulfonyl]anilino}piperidin-1-yl)sulfonyl]thien-2-yl}methyl)-4-chlorobenzamide
4-chloro-N-[(5-{[4-(3-ethylanilino)piperidin-1-yl]sulfonyl}thien-2-yl)methyl]benzamide
4-chloro-N-[(5-{[4-(5,6,7,8-tetrahydronaphthalen-1-ylamino)piperidin-1-yl]sulfonyl}thien-2-yl)methyl]benzamide
N-{[5-({4-[3-(aminosulfonyl)anilino]piperidin-1-yl}sulfonyl)thien-2-yl]methyl}-4-chlorobenzamide
4-chloro-N-[(5-{[4-(quinolin-5-ylamino)piperidin-1-yl]sulfonyl}thien-2-yl)methyl]benzamide
4-chloro-N-[(5-{[4-(quinolin-8-ylamino)piperidin-1-yl]sulfonyl}thien-2-yl)methyl]benzamide
4-Chloro-N-[(5-{[4-(3-propylphenoxy)piperidin-1-yl]sulfonyl}thien-2-yl)methyl]benzamide
4-chloro-N-{5-({4-[(2E)-3-phenylprop-2-enoyl]piperazin-1-yl}sulfonyl)thien-2-yl]methyl}benzamide
4-chloro-N-({5-[(4-{4-nitrobenzoyl}piperazin-1-yl)sulfonyl]thien-2-yl}methyl)benzamide
N-({5-[(4-benzoylpiperazin-1-yl)sulfonyl]thien-2-yl}methyl)-4-chlorobenzamide
4-chloro-N-{[5-({4-[4-(trifluoromethyl)benzoyl]piperazin-1-yl}sulfonyl)thien-2-yl]methyl}benzamide
4-chloro-N-{[5-({4-[4-(dimethylamino)benzoyl]piperazin-1-yl}sulfonyl)thien-2-yl]methyl}benzamide
4-chloro-N-[(5-{[4-(2-fluorobenzoyl)piperazin-1-yl]sulfonyl}thien-2-yl)methyl]benzamide
4-chloro-N-[(5-{[4-(2,6-difluorobenzoyl)piperazin-1-yl]sulfonyl}thien-2-yl)methyl]benzamide
4-chloro-N-[(5-{[4-(3-fluorobenzoyl)piperazin-1-yl]sulfonyl}thien-2-yl)methyl]benzamide
4-chloro-N-[(5-{[4-(2-naphthoyl)piperazin-1-yl]sulfonyl}thien-2-yl)methyl]benzamide
4-chloro-N-[(5-{[4-(1-naphthoyl)piperazin-1-yl]sulfonyl}thien-2-yl)methyl]benzamide
4-chloro-N-({5-[(4-{2-nitrobenzoyl}piperazin-1-yl)sulfonyl]thien-2-yl}methyl)benzamide
4-chloro-N-[(5-{[4-(pyridin-3-ylcarbonyl)piperazin-1-yl]sulfonyl}thien-2-yl)methyl]benzamide
N-[(5-{[4-(2,1,3-benzoxadiazol-5-ylcarbonyl)piperazin-1-yl]sulfonyl}thien-2-yl)methyl]-4-chlorobenzamide
4-chloro-N-[(5-{[4-(2,4-difluorobenzoyl)piperazin-1-yl]sulfonyl}thien-2-yl)methyl]benzamide
4-chloro-N-[(5-{[4-(2,4,6-trifluorobenzoyl)piperazin-1-yl]sulfonyl}thien-2-yl)methyl]benzamide
4-chloro-N-[(5-{[4-(2,6-dichlorobenzoyl)piperazin-1-yl]sulfonyl}thien-2-yl)methyl]benzamide
4-chloro-N-({5-[(4-heptanoylpiperazin-1-yl)sulfonyl]thien-2-yl}methyl)benzamide
4-chloro-N-[(5-{[4-(quinolin-8-ylsulfonyl)piperazin-1-yl]sulfonyl}thien-2-yl)methyl]benzamide
4-nitro-N-({5-[(4-{3-[(trifluoromethyl)sulfonyl]anilino}piperidin-1-yl)sulfonyl]thien-2-yl}methyl)benzamide
N-[(5-{[4-(1H-1,2,3-benzotriazol-1-yl)piperidin-1-yl]sulfonyl}thien-2-yl)methyl]-3-nitrobenzamide
4-nitro-N-({5-[(4-{3-[(trifluoromethyl)sulfonyl]anilino}piperidin-1-yl)sulfonyl]thien-2-yl}methyl)benzamide
N-[(5-{[4-(2,4-difluorobenzoyl)piperidin-1-yl]sulfonyl}thien-2-yl)methyl]-4-nitrobenzamide
N-[(5-{[4-(1H-1,2,3-benzotriazol-1-yl)piperidin-1-yl]sulfonyl}thien-2-yl)methyl]-4-nitrobenzamide
N-[(5-{[4-(1H-1,2,3-benzotriazol-1-yl)piperidin-1-yl]sulfonyl}thien-2-yl)methyl]-3-nitrobenzamide
4-nitro-N-({5-[(4-{3-[(trifluoromethyl)sulfonyl]anilino}piperidin-1-yl)sulfonyl]thien-2-yl}methyl)benzamide
N-[(5-{[4-(2,4-difluorobenzoyl)piperidin-1-yl]sulfonyl}thien-2-yl)methyl]-4-nitrobenzamide
N-[(5-{[4-(1H-1,2,3-benzotriazol-1-yl)piperidin-1-yl]sulfonyl}thien-2-yl)methyl]-4-nitrobenzamide
3-nitro-N-[(5-{[4-(3-methoxyanilino)piperidin-1-yl]sulfonyl}thien-2-yl)methyl]benzamide
3-nitro-N-{[5-({4-[3-(trifluoromethyl)anilino]piperidin-1-yl}sulfonyl)thien-2-yl]methyl}benzamide
N-{[5-({4-[3-(dimethylamino)anilino]piperidin-1-yl}sulfonyl)thien-2-yl]methyl}-3-nitrobenzamide
3-nitro-N-{[5-({4-[3-(methylsulfonyl)anilino]piperidin-1-yl}sulfonyl)thien-2-yl]methyl}benzamide
3-nitro-N-{[5-({4-[3-(methylsulfanyl)anilino]piperidin-1-yl}sulfonyl)thien-2-yl]methyl}benzamide
N-{[5-({4-[3-(aminosulfonyl)anilino]piperidin-1-yl}sulfonyl)thien-2-yl]methyl}-3-nitrobenzamide
methyl 3-{[1-({5-[({3-nitrobenzoyl}amino)methyl]-thien-2-yl}sulfonyl)-piperidin-4-yl]amino}benzoate
N-{[5-({4-[3-(aminocarbonyl)anilino]piperidin-1-yl}sulfonyl)thien-2-yl]methyl}-3-nitrobenzamide
3-nitro-N-({5-[(4-{3-nitroanilino}piperidin-1-yl)sulfonyl]thien-2-yl}methyl)benzamide
3-nitro-N-[(5-{[4-(2-methoxyanilino)piperidin-1-yl]sulfonyl}thien-2-yl)methyl]benzamide
3-nitro-N-{[5-({4-[2-(trifluoromethyl)anilino]piperidin-1-yl}sulfonyl)thien-2-yl]methyl}benzamide
3-nitro-N-({5-[(4-{2-nitroanilino}piperidin-1-yl)sulfonyl]thien-2-yl}methyl)benzamide
N-[(5-{[4-(4-chloroanilino)piperidin-1-yl]sulfonyl}thien-2-yl)methyl]-3-nitrobenzamide
3-nitro-N-{[5-({4-[4-(trifluoromethyl)anilino]piperidin-1-yl}sulfonyl)thien-2-yl]methyl}benzamide
3-nitro-N-({5-[(4-{[(trifluoromethyl)sulfonyl]anilino}piperidin-1-yl)sulfonyl]thien-2-yl}methyl)benzamide
N-{[5-({4-[4-(aminocarbonyl)anilino]piperidin-1-yl}sulfonyl)thien-2-yl]methyl}-3-nitrobenzamide
N-[(5-{[4-(3-propylanilino)piperidin-1-yl]sulfonyl}thien-2-yl)methyl]-3-nitrobenzamide
N-[(5-{[4-(3-chloroanilino)piperidin-1-yl]sulfonyl}thien-2-yl)methyl]-4-nitrobenzamide
4-nitro-N-[(5-{[4-(3-methoxyanilino)piperidin-1-yl]sulfonyl}thien-2-yl)methyl]benzamide
4-nitro-N-{[5-({4-[3-(trifluoromethyl)anilino]piperidin-1-yl}sulfonyl)thien-2-yl]methyl}benzamide
N-{[5-({4-[3-(dimethylamino)anilino]piperidin-1-yl}sulfonyl)thien-2-yl]methyl}-4-nitrobenzamide
4-nitro-N-[(5-{[4-(3-propylanilino)piperidin-1-yl]sulfonyl}thien-2-yl)methyl]benzamide
4-nitro-N-{[5-({4-[3-(methylsulfonyl)anilino]piperidin-1-yl}sulfonyl)thien-2-yl]methyl}benzamide
4-nitro-N-{[5-({4-[3-(methylsulfanyl)anilino]piperidin-1-yl}sulfonyl)thien-2-yl]methyl}benzamide
N-{[5-({4-[3-(aminosulfonyl)anilino]piperidin-1-yl}sulfonyl)thien-2-yl]methyl}-4-nitrobenzamide
3-{[1-({5-[({4-nitrobenzoyl}amino)methyl]thien-2-yl}sulfonyl)piperidin-4-yl]amino}benzamide
3-{[1-({5-[({4-nitrobenzoyl}amino)methyl]thien-2-yl}sulfonyl)piperidin-4-yl]amino}benzamide 4-nitro-N-({5-[(4-{3-nitroanilino}piperidin-1-yl)sulfonyl]thien-2-yl}methyl)benzamide
4-nitro-N-[(5-{[4-(2-methoxyanilino)piperidin-1-yl]sulfonyl}thien-2-yl)methyl]benzamide
4-nitro-N-{[5-({4-[2-(trifluoromethyl)anilino]piperidin-1-yl}sulfonyl)thien-2-yl]methyl}benzamide
4-nitro-N-({5-[(4-{2-nitroanilino}piperidin-1-yl)sulfonyl]thien-2-yl}methyl)benzamide
N-[(5-{[4-(4-chloroanilino)piperidin-1-yl]sulfonyl}thien-2-yl)methyl]-4-nitrobenzamide
4-nitro-N-{[5-({4-[4-(trifluoromethyl)anilino]piperidin-1-yl}sulfonyl)thien-2-yl]methyl}benzamide
4-nitro-N-({5-[(4-{4-[(trifluoromethyl)sulfonyl]anilino}piperidin-1-yl)sulfonyl]thien-2-yl}methyl)benzamide
N-{[5-({4-[4-(aminocarbonyl)anilino]piperidin-1-yl}sulfonyl)thien-2-yl]methyl}-4-nitrobenzamide
N-{[5-({4-[4-(1,3-dithiolan-2-yl)anilino]piperidin-1-yl}sulfonyl)thien-2-yl]methyl}-4-nitrobenzamide
N-({5-[(4-{3-[amino(imino)methyl]anilino}piperidin-1-yl)sulfonyl]thien-2-yl}methyl)-3-nitrobenzamide
N-({5-[(4-{3-[(2-hydroxyethyl)sulfonyl]anilino}piperidin-1-yl)sulfonyl]thien-2-yl}methyl)-3-nitrobenzamide
N-({5-[(4-anilinopiperidin-1-yl)sulfonyl]thien-2-yl}methyl)-3-nitrobenzamide
N-({5-[(4-{3-[(2-hydroxyethyl)sulfonyl]anilino}piperidin-1-yl)sulfonyl]thien-2-yl}methyl)-4-nitrobenzamide
N-({5-[(4-anilinopiperidin-1-yl)sulfonyl]thien-2-yl}methyl)-4-nitrobenzamide
N-({5-[(4-{3-[amino(imino)methyl]anilino}piperidin-1-yl)sulfonyl]thien-2-yl}methyl)-4-nitrobenzamide
3-nitro-N-({5-[(4-{3-[(trifluoromethyl)sulfanyl]anilino}piperidin-1-yl)sulfonyl]thien-2-yl}methyl)benzamide
4-nitro-N-({5-[(4-{3-[(trifluoromethyl)sulfanyl]anilino}piperidin-1-yl)sulfonyl]thien-2-yl}methyl)benzamide
3-nitro-N-[(5-{[4-({3-nitropyridin-2-yl}amino)piperidin-1-yl]sulfonyl}thien-2-yl)methyl]benzamide
N-{[5-({4-[(2,2-dioxido-1,3-dihydro-2-benzothien-5-yl)amino]piperidin-1-yl}sulfonyl)thien-2-yl]methyl}-3-nitrobenzamide
N-[(5-{[4-(2,3-dihydro-1H-inden-5-ylamino)piperidin-1-yl]sulfonyl}thien-2-yl)methyl]-3-nitrobenzamide
3-nitro-N-[(5-{[4-(2-propylanilino)piperidin-1-yl]sulfonyl}thien-2-yl)methyl]benzamide
3-nitro-N-[(5-{[4-(4-propylanilino)piperidin-1-yl]sulfonyl}thien-2-yl)methyl]benzamide
N-[(5-{[4-(3-tert-butylanilino)piperidin-1-yl]sulfonyl}thien-2-yl)methyl]-3-nitrobenzamide
3-nitro-N-{[5-({4-[3-(1,3-oxazol-5-yl)anilino]piperidin-1-yl}sulfonyl)thien-2-yl]methyl}benzamide
3-nitro-N-[(5-{[4-(2-phenylethyl)piperidin-1-yl]sulfonyl}thien-2-yl)methyl]benzamide
N-({5-[(4-{[3-chloro-5-(trifluoromethyl)pyridin-2-yl]amino}piperidin-1-yl)sulfonyl]thien-2-yl}methyl)-3-nitrobenzamide
N-[(5-{[4-([1,1'-biphenyl]-3-ylamino)piperidin-1-yl]sulfonyl}thien-2-yl)methyl]-3-nitrobenzamide
N-[(5-{[4-(3-benzylanilino)piperidin-1-yl]sulfonyl}thien-2-yl)methyl]-3-nitrobenzamide
3-nitro-N-{[5-({4-[3-(morpholin-4-ylsulfonyl)anilino]piperidin-1-yl}sulfonyl)thien-2-yl]methyl}benzamide
3-nitro-N-[(5-{[4-(3-propylphenoxy)piperidin-1-yl]sulfonyl}thien-2-yl)methyl]benzamide
4-nitro-N-[(5-{[4-(pyrimidin-2-ylamino)piperidin-1-yl]sulfonyl}thien-2-yl)methyl]benzamide
N-{[5-({4-[(3-aminopyridin-2-yl)amino]piperidin-1-yl}sulfonyl)thien-2-yl]methyl}-4-nitrobenzamide
4-nitro-N-[(5-{[4-({3-nitropyridin-2-yl}amino)piperidin-1-yl]sulfonyl}thien-2-yl)methyl]benzamide
N-[(5-{[4-(2,3-dihydro-1H-inden-5-ylamino)piperidin-1-yl]sulfonyl}thien-2-yl)methyl]-4-nitrobenzamide
4-nitro-N-[(5-{[4-(2-propylanilino)piperidin-1-yl]sulfonyl}thien-2-yl)methyl]benzamide
4-nitro-N-[(5-{[4-(4-propylanilino)piperidin-1-yl]sulfonyl}thien-2-yl)methyl]benzamide
N-[(5-{[4-(3-tert-butylanilino)piperidin-1-yl]sulfonyl}thien-2-yl)methyl]-4-nitrobenzamide
4-nitro-N-{[5-({4-[3-(1,3-oxazol-5-yl)anilino]piperidin-1-yl}sulfonyl)thien-2-yl]methyl}benzamide
4-nitro-N-[(5-{[4-(2-phenylethyl)piperidin-1-yl]sulfonyl}thien-2-yl)methyl]benzamide
N-({5-[(4-{[3-chloro-5-(trifluoromethyl)pyridin-2-yl]amino}piperidin-1-yl)sulfonyl]thien-2-yl}methyl)-4-nitrobenzamide
N-[(5-{[4-([1,1'-biphenyl]-3-ylamino)piperidin-1-yl]sulfonyl}thien-2-yl)methyl]-4-nitrobenzamide
N-[(5-{[4-(3-benzylanilino)piperidin-1-yl]sulfonyl}thien-2-yl)methyl]-4-nitrobenzamide
4-nitro-N-{[5-({4-[3-(morpholin-4-ylsulfonyl)anilino]piperidin-1-yl}sulfonyl)thien-2-yl]methyl}benzamide
N-[(5-{[4-(2-aminoanilino)piperidin-1-yl]sulfonyl}thien-2-yl)methyl]-3-nitrobenzamide
3-nitro-N-[(5-{[4-(pyrimidin-2-ylamino)piperidin-1-yl]sulfonyl}thien-2-yl)methyl]benzamide
N-{[5-({4-[(3-aminopyridin-2-yl)amino]piperidin-1-yl}sulfonyl)thien-2-yl]methyl}-3-nitrobenzamide
N-({5-[(4-{2-nitro-4-[(trifluoromethyl)sulfonyl]anilino}piperidin-1-yl)sulfonyl]thien-2-yl}methyl)-3-methoxybenzamide
3-nitro-N-[(5-{[4-(3-phenylpropyl)piperazin-1-yl]sulfonyl}thien-2-yl)methyl]benzamide
3-nitro-N-({5-[(4-{[4-(trifluoromethyl)pyrimidin-2-yl]amino}piperidin-1-yl)sulfonyl]thien-2-yl}methyl)benzamide
N-[(5-{[4-(3-cyclohexyl-4-hydroxyanilino)piperidin-1-yl]sulfonyl}thien-2-yl)methyl]-3-nitrobenzamide
N-({5-[(4-{3-[(butylamino)sulfonyl]anilino}piperidin-1-yl)sulfonyl]thien-2-yl}methyl)-3-nitrobenzamide
N-[(5-{[4-(3-ethylanilino)piperidin-1-yl]sulfonyl}thien-2-yl)methyl]-3-nitrobenzamide
3-nitro-N-[(5-{[4-(5,6,7,8-tetrahydronaphthalen-1-ylamino)piperidin-1-yl]sulfonyl}thien-2-yl)methyl]benzamide
4-nitro-N-[(5-{[4-(3-propylphenoxy)piperidin-1-yl]sulfonyl}thien-2-yl)methyl]benzamide
N-[(5-{[4-(2,4-difluorobenzoyl)piperidin-1-yl]sulfonyl}thien-2-yl)methyl]-3-nitrobenzamide
N-[(5-{[4-(2,4-difluorobenzoyl)piperidin-1-yl]sulfonyl}thien-2-yl)methyl]-3-methoxybenzamide
2-Hydroxy-N-({5-[(4-{3-[(trifluoromethyl)sulfonyl]anilino}piperidin-1-yl)sulfonyl]thien-2-yl}methyl)benzamide
N-[(5-{[4-(1H-1,2,3-benzotriazol-1-yl)piperidin-1-yl]sulfonyl}thien-2-yl)methyl]-3-methoxybenzamide
N-[(5-{[4-(1H-1,2,3-benzotriazol-1-yl)piperidin-1-yl]sulfonyl}thien-2-yl)methyl]-2-hydroxybenzamide
N-{[5-({4-[4-(1,3-dithiolan-2-yl)anilino]piperidin-1-yl}sulfonyl)thien-2-yl]methyl}-3-nitrobenzamide
3-methoxy-N-[(5-{[4-(3-methoxyanilino)piperidin-1-yl]sulfonyl}thien-2-yl)methyl]benzamide
3-methoxy-N-{[5-({4-[3-(trifluoromethyl)anilino]piperidin-1-yl}sulfonyl)thien-2-yl]methyl}benzamide N-{[5-({4-[3-(dimethylamino)anilino]piperidin-1-yl}sulfonyl)thien-2-yl]methyl}-3-methoxybenzamide
3-methoxy-N-[(5-{[4-(3-propylanilino)piperidin-1-yl]sulfonyl}thien-2-yl)methyl]benzamide
3-methoxy-N-{[5-({4-[3-(methylsulfonyl)anilino]piperidin-1-yl}sulfonyl)thien-2-yl]methyl}benzamide
3-methoxy-N-{[5-({4-[3-(methylsulfanyl)anilino]piperidin-1-yl}sulfonyl)thien-2-yl]methyl}benzamide
N-{[5-({4-[3-(aminosulfonyl)anilino]piperidin-1-yl}sulfonyl)thien-2-yl]methyl}-3-methoxybenzamide
methyl 3-({1-[(5-{[(3-methoxybenzoyl)amino]methyl}thien-2-yl)sulfonyl]-piperidin-4-yl}amino)-benzoate
N-{[5-({4-[3-(aminocarbonyl)anilino]piperidin-1-yl}sulfonyl)thien-2-yl]methyl}-3-methoxybenzamide
3-methoxy-N-[(5-{[4-(2-methoxyanilino)piperidin-1-yl]sulfonyl}thien-2-yl)methyl]benzamide
N-({5-[(4-{3-nitroanilino}piperidin-1-yl)sulfonyl]thien-2-yl}methyl)-3-methoxybenzamide
3-methoxy-N-{[5-({4-[2-(trifluoromethyl)anilino]piperidin-1-yl}sulfonyl)thien-2-yl]methyl}benzamide
N-({5-[(4-{2-nitroanilino}piperidin-1-yl)sulfonyl]thien-2-yl}methyl)-3-methoxybenzamide
N-{[5-({4-[4-(aminocarbonyl)anilino]piperidin-1-yl}sulfonyl)thien-2-yl]methyl}-3-methoxybenzamide
N-{[5-({4-[4-(1,3-dithiolan-2-yl)anilino]piperidin-1-yl}sulfonyl)thien-2-yl]methyl}-3-methoxybenzamide
N-[(5-{[4-(3-chloroanilino)piperidin-1-yl]sulfonyl}thien-2-yl)methyl]-3-methoxybenzamide
N-[(5-{[4-(4-chloroanilino)piperidin-1-yl]sulfonyl}thien-2-yl)methyl]-3-methoxybenzamide
3-methoxy-N-({5-[(4-{4-[(trifluoromethyl)sulfonyl]anilino}piperidin-1-yl)sulfonyl]thien-2-yl}methyl)benzamide
N-({5-[(4-{3-[amino(imino)methyl]anilino}piperidin-1-yl)sulfonyl]thien-2-yl}methyl)-3-methoxybenzamide
N-({5-[(4-{3-[(2-hydroxyethyl)sulfonyl]anilino}piperidin-1-yl)sulfonyl]thien-2-yl}methyl)-3-methoxybenzamide
3-methoxy-N-({5-[(4-{3-[(trifluoromethyl)sulfonyl]anilino}piperidin-1-yl)sulfonyl]thien-2-yl}methyl)benzamide
N-({5-[(4-anilinopiperidin-1-yl)sulfonyl]thien-2-yl}methyl)-3-methoxybenzamide
3-methoxy-N-({5-[(4-{3-[(trifluoromethyl)sulfanyl]anilino}piperidin-1-yl)sulfonyl]thien-2-yl}methyl)benzamide
N-[(5-{[4-(4-hydroxyanilino)piperidin-1-yl]sulfonyl}thien-2-yl)methyl]-3-methoxybenzamide
3-nitro-N-({5-[(4-{3-[(trifluoromethyl)sulfanyl]anilino}piperidin-1-yl)sulfonyl]thien-2-yl}methyl)benzamide
4-nitro-N-({5-[(4-{3-[(trifluoromethyl)sulfanyl]anilino}piperidin-1-yl)sulfonyl]thien-2-yl}methyl)benzamide
N-[(5-{[4-(2-hydroxyanilino)piperidin-1-yl]sulfonyl}thien-2-yl)methyl]-3-methoxybenzamide
3-methoxy-N-[(5-{[4-(pyrimidin-2-ylamino)piperidin-1-yl]sulfonyl}thien-2-yl)methyl]benzamide
N-{[5-({4-[(3-aminopyridin-2-yl)amino]piperidin-1-yl}sulfonyl)thien-2-yl]methyl}-3-methoxybenzamide
N-[(5-{[4-({3-nitropyridin-2-yl}amino)piperidin-1-yl]sulfonyl}thien-2-yl)methyl]-3-methoxybenzamide
N-{[5-({4-[(2,2-dioxido-1,3-dihydro-2-benzothien-5-yl)amino]piperidin-1-yl}sulfonyl)thien-2-yl]methyl}-3-methoxybenzamide
N-[(5-{[4-(2,3-dihydro-1H-inden-5-ylamino)piperidin-1-yl]sulfonyl}thien-2-yl)methyl]-3-methoxybenzamide
3-methoxy-N-[(5-{[4-(2-propylanilino)piperidin-1-yl]sulfonyl}thien-2-yl)methyl]benzamide
3-methoxy-N-[(5-{[4-(4-propylanilino)piperidin-1-yl]sulfonyl}thien-2-yl)methyl]benzamide
N-[(5-{[4-(3-tert-butylanilino)piperidin-1-yl]sulfonyl}thien-2-yl)methyl]-3-methoxybenzamide
N-({5-[(4-{[3-chloro-5-(trifluoromethyl)pyridin-2-yl]amino}piperidin-1-yl)sulfonyl]thien-2-yl}methyl)-3-methoxybenzamide
3-methoxy-N-{[5-({4-[3-(1,3-oxazol-5-yl)anilino]piperidin-1-yl}sulfonyl)thien-2-yl]methyl}benzamide
N-[(5-{[4-([1,1'-biphenyl]-3-ylamino)piperidin-1-yl]sulfonyl}thien-2-yl)methyl]-3-methoxybenzamide
3-methoxy-N-[(5-{[4-(3-propylphenoxy)piperidin-1-yl]sulfonyl}thien-2-yl)methyl]benzamide
3-methoxy-N-{[5-({4-[3-(morpholin-4-ylsulfonyl)anilino]piperidin-1-yl}sulfonyl)thien-2-yl]methyl}benzamide
3-methoxy-N-[(5-{[4-(2-phenylethyl)piperidin-1-yl]sulfonyl}thien-2-yl)methyl]benzamide
N-[(5-{[4-(3-benzylanilino)piperidin-1-yl]sulfonyl}thien-2-yl)methyl]-3-methoxybenzamide
3-methoxy-N-[(5-{[4-(3-phenylpropyl)piperazin-1-yl]sulfonyl}thien-2-yl)methyl]benzamide
3-methoxy-N-({5-[(4-{[4-(trifluoromethyl)pyrimidin-2-yl]amino}piperidin-1-yl)sulfonyl]thien-2-yl}methyl)benzamide
N-[(5-{[4-(3-cyclohexyl-4-hydroxyanilino)piperidin-1-yl]sulfonyl}thien-2-yl)methyl]-3-methoxybenzamide
N-({5-[(4-{3-[(butylamino)sulfonyl]anilino}piperidin-1-yl)sulfonyl]thien-2-yl}methyl)-3-methoxybenzamide
N-[(5-{[4-(3-ethylanilino)piperidin-1-yl]sulfonyl}thien-2-yl)methyl]-3-methoxybenzamide
3-methoxy-N-[(5-{[4-(5,6,7,8-tetrahydronaphthalen-1-ylamino)piperidin-1-yl]sulfonyl}thien-2-yl)methyl]benzamide
N-[(5-{[4-(1H-1,2,3-benzotriazol-1-yl)piperidin-1-yl]sulfonyl}thien-2-yl)methyl]-5-nitro-1H-pyrazole-3-carboxamide
N-[(5-{[4-(1H-1,2,3-benzotriazol-1-yl)piperidin-1-yl]sulfonyl}thien-2-yl)methyl]-2-oxo-1,2-dihydropyridine-3-carboxamide
N-[(5-{[4-(1H-1,2,3-benzotriazol-1-yl)piperidin-1-yl]sulfonyl}thien-2-yl)methyl]-2-thioxo-1,2-dihydropyridine-3-carboxamide
N-[(5-{[4-(1H-1,2,3-benzotriazol-1-yl)piperidin-1-yl]sulfonyl}thien-2-yl)methyl]-3,4-dihydroxybenzamide
N-[(5-{[4-(1H-1,2,3-benzotriazol-1-yl)piperidin-1-yl]sulfonyl}thien-2-yl)methyl]pyridine-2-carboxamide
N-[(5-{[4-(hexyloxy)piperidin-1-yl]sulfonyl}thien-2-yl)methyl]-3-methoxybenzamide
N-({5-[(4-heptanoylpiperidin-1-yl)sulfonyl]thien-2-yl}methyl)-3-methoxybenzamide
4-chloro-N-[(5-{[4-(3-propylanilino)piperidin-1-yl]sulfonyl}-2-furyl)methyl]benzamide
4-chloro-N-[(5-{[4-(3-chloroanilino)piperidin-1-yl]sulfonyl}-2-furyl)methyl]benzamide
4-chloro-N-[(5-{[4-(3-methoxyanilino)piperidin-1-yl]sulfonyl}-2-furyl)methyl]benzamide
4-chloro-N-{[5-({4-[3-(trifluoromethyl)anilino]piperidin-1-yl}sulfonyl)-2-furyl]methyl}benzamide
4-chloro-N-{[5-(f{4-[3-(dimethylamino)anilino]piperidin-1-yl}sulfonyl)-2-furyl]methyl}benzamide
4-chloro-N-{[5-({4-[3-(methylsulfonyl)anilino]piperidin-1-yl}sulfonyl)-2-furyl]methyl}benzamide
4-chloro-N-{[5-({4-[3-(methylsulfanyl)anilino]piperidin-1-yl}sulfonyl)-2-furyl]methyl}benzamide N-{[5-({4-[3-(aminosulfonyl)anilino]piperidin-1-yl}sulfonyl)-2-furyl]methyl}-4-chlorobenzamide
methyl 3-({1-[(5-{[(4-chlorobenzoyl)amino]methyl}-2-furyl)sulfonyl]piperidin-4-yl}amino)benzoate
3-({1-[(5-{[(4-chlorobenzoyl)amino]methyl}-2-furyl)sulfonyl]piperidin-4-yl}amino)benzamide
4-chloro-N-({5-[(4-{3-nitroanilino}piperidin-1-yl)sulfonyl]-2-furyl}methyl)benzamide
4-chloro-N-[(5-{[4-(2-methoxyanilino)piperidin-1-yl]sulfonyl}-2-furyl)methyl]benzamide
4-chloro-N-{[5-({4-[2-(trifluoromethyl)anilino]piperidin-1-yl}sulfonyl)-2-furyl]methyl}benzamide
4-chloro-N-({5-[(4-{2-nitroanilino}piperidin-1-yl)sulfonyl]-2-furyl}methyl)benzamide
4-chloro-N-[(5-{[4-(4-chloroanilino)piperidin-1-yl]sulfonyl}-2-furyl)methyl]benzamide
4-chloro-N-{[5-({4-[4-(trifluoromethyl)anilino]piperidin-1-yl}sulfonyl)-2-furyl]methyl}benzamide
4-chloro-N-({5-[(4-{4-[(trifluoromethyl)sulfonyl]anilino}piperidin-1-yl)sulfonyl]-2-furyl}methyl)benzamide
N-{[5-({4-[4-(aminocarbonyl)anilino]piperidin-1-yl}sulfonyl)-2-furyl]methyl}-4-chlorobenzamide
4-chloro-N-{[5-({4-[4-(1,3-dithiolan-2-yl)anilino]piperidin-1-yl}sulfonyl)-2-furyl]methyl}benzamide
N-({5-[(4-{3-[amino(imino)methyl]anilino}piperidin-1-yl)sulfonyl]-2-furyl}methyl)-4-chlorobenzamide
4-chloro-N-({5-[(4-{3-[(trifluoromethyl)sulfonyl]anilino}piperidin-1-yl)sulfonyl]-2-furyl}methyl)benzamide
N-({5-[(4-anilinopiperidin-1-yl)sulfonyl]-2-furyl}methyl)-4-chlorobenzamide
4-nitro-N-({5-[(4-{3-[(trifluoromethyl)sulfanyl]anilino}piperidin-1-yl)sulfonyl]2-furyl}methyl)benzamide
4-chloro-N-({5-[(3-{3-[(trifluoromethyl)sulfonyl]anilino}pyrrolidin-1-yl)sulfonyl]thien-2-yl}methyl)benzamide
4-chloro-N-({5-[(4-{3-[(trifluoromethyl)sulfonyl]anilino}azepan-1-yl)sulfonyl]thien-2-yl}methyl)benzamide
5-{[(3-methoxybenzoyl)amino]methyl}-2-[(4-{3-[(trifluoromethyl)sulfonyl]-anilino}piperidin-1-yl)sulfonyl]thiophene-3-carboxylic acid
5-{[(3-methoxybenzoyl)amino]methyl}-2-{[4-(octylamino)piperidin-1-yl]sulfonyl}thiophene-3-carboxylic acid
N-(2-hydroxyethyl)-5-{[(3-methoxybenzoyl)amino]methyl}-2-[(4-{3-[(trifluoro-methyl)sulfonyl]anilino}piperidin-1-yl)sulfonyl]thiophene-3-carboxamide
N-({4-(hydrazinocarbonyl)-5-[(4-{3-[(trifluoromethyl)sulfonyl]anilino}-piperidin-1-yl)sulfonyl]thien-2-yl}methyl)-3-methoxybenzamide
5-{[(3-methoxybenzoyl)amino]methyl}-2-[(4-{3-[(trifluoromethyl)sulfonyl]-anilino}piperidin-1-yl)sulfonyl]thiophene-3-carboxamide
N-[2-(dimethylamino)ethyl]-5-{[(3-methoxybenzoyl)amino]methyl}-2-[(4-{3-[(trifluoromethyl)sulfonyl]anilino}piperidin-1-yl)sulfonyl]thiophene-3-carboxamide
N-({4-(hydroxymethyl)-5-[(4-{3-[(trifluoromethyl)sulfonyl]anilino}piperidin-1-yl)sulfonyl]thien-2-yl}methyl)-3-methoxybenzamide
4-chloro-N-[(5-{[4-(hexylamino)piperidin-1-yl]sulfonyl}thien-2-yl)methyl]benzamide
3-Methoxy-N-{[5-({4-[(4-trifluoromethylbenzyl)amino]piperidin-1-yl}sulfonyl)thien-2-yl]methyl}benzamide
4-chloro-N-[(5-{[4-(1,3-thiazol-2-ylamino)piperidin-1-yl]sulfonyl}thien-2-yl)methyl]benzamide
4-chloro-N-[(5-{[4-(heptylamino)piperidin-1-yl]sulfonyl}thien-2-yl)methyl]benzamide
4-chloro-N-[(5-{[4-(pentylamino)piperidin-1-yl]sulfonyl}thien-2-yl)methyl]benzamide
4-chloro-N-[(5-{[4-(butylamino)piperidin-1-yl]sulfonyl}thien-2-yl)methyl]benzamide
4-chloro-N-[(5-{[4-(dodecylamino)piperidin-1-yl]sulfonyl}thien-2-yl)methyl]benzamide
4-chloro-N-{[5-({4-[(2-cyclohexylethyl)amino]piperidin-1-yl}sulfonyl)thien-2-yl]methyl}benzamide
4-chloro-N-{[5-({4-[(cyclohexylmethyl)amino]piperidin-1-yl}sulfonyl)thien-2-yl]methyl}benzamide
4-chloro-N-({5-[(4-{[(1R)-1-cyclohexylethyl]amino}piperidin-1-yl)sulfonyl]thien-2-yl}methyl)benzamide
N-{[5-({4-[(1R,2R,4S)-bicyclo[2.2.1]hept-2-ylamino]piperidin-1-yl}sulfonyl)thien-2-yl]methyl}-4-chlorobenzamide
4-chloro-N-{[5-({4-[(2-propoxyethyl)amino]piperidin-1-yl}sulfonyl)thien-2-yl]methyl}benzamide
N-{[5-({4-[(1-adamantylmethyl)amino]piperidin-1-yl}sulfonyl)thien-2-yl]methyl}-4-chlorobenzamide
4-chloro-N-{[5-({4-[(2-pyridin-2-ylethyl)amino]piperidin-1-yl}sulfonyl)thien-2-yl]methyl}benzamide
4-chloro-N-{[5-({4-[(2-piperidin-1-ylethyl)amino]piperidin-1-yl}sulfonyl)thien-2-yl]methyl}benzamide
4-chloro-N-{[5-({4-[(2-ethylhexyl)amino]piperidin-1-yl}sulfonyl)thien-2-yl]methyl}benzamide
4-chloro-N-({5-[(4-{[3-(1H-imidazol-1-yl)propyl]amino}piperidin-1-yl)sulfonyl]thien-2-yl}methyl)benzamide
4-chloro-N-[(5-{[4-(octylamino)piperidin-1-yl]sulfonyl}thien-2-yl)methyl]benzamide
N-[(5-{[4-(heptylamino)piperidin-1-yl]sulfonyl}thien-2-yl)methyl]-3-methoxybenzamide
3-methoxy-N-[(5-{[4-(octylamino)piperidin-1-yl]sulfonyl}thien-2-yl)methyl]benzamide
3-methoxy-N-[(5-{[4-(pentylamino)piperidin-1-yl]sulfonyl}thien-2-yl)methyl]benzamide
N-[(5-{[4-(butylamino)piperidin-1-yl]sulfonyl}thien-2-yl)methyl]-3-methoxybenzamide
N-[(5-{[4-(dodecylamino)piperidin-1-yl]sulfonyl}thien-2-yl)methyl]-3-methoxybenzamide
N-{[5-({4-[(2-cyclohexylethyl)amino]piperidin-1-yl}sulfonyl)thien-2-yl]methyl}-3-methoxybenzamide
N-({5-[(4-{[(1R)-1-cyclohexylethyl]amino}piperidin-1-yl)sulfonyl]thien-2-yl}methyl)-3-methoxybenzamide
N-{[5-({4-[(1R,2R,4S)-bicyclo[2.2.1]hept-2-ylamino]piperidin-1-yl}sulfonyl)thien-2-yl]methyl}-3-methoxybenzamide
3-methoxy-N-{[5-({4-[(2-propoxyethyl)amino]piperidin-1-yl}sulfonyl)thien-2-yl]methyl}benzamide
N-{[5-({4-[(1-adamantylmethyl)amino]piperidin-1-yl}sulfonyl)thien-2-yl]methyl}-3-methoxybenzamide
N-{[5-({4-[(3,3-diethoxypropyl)amino]piperidin-1-yl}sulfonyl)thien-2-yl]methyl}-3-methoxybenzamide
3-methoxy-N-{[5-({4-[(3-morpholin-4-ylpropyl)amino]piperidin-1-yl}sulfonyl)thien-2-yl]methyl}benzamide
3-methoxy-N-{[5-({4-[(2-pyridin-2-ylethyl)amino]piperidin-1-yl}sulfonyl)thien-2-yl]methyl}benzamide
3-methoxy-N-{[5-({4-[(2-piperidin-1-ylethyl)amino]piperidin-1-yl}sulfonyl)thien-2-yl]methyl}benzamide
N-{[5-({4-[(2-ethylhexyl)amino]piperidin-1-yl}sulfonyl)thien-2-yl]methyl}-3-methoxybenzamide N-({5-[(4-{[3-(1H-imidazol-1-yl)propyl]amino}piperidin-1-yl)sulfonyl]thien-2-yl}methyl)-3-methoxybenzamide
N-[(5-{[4-(hexylamino)piperidin-1-yl]sulfonyl}thien-2-yl)methyl]-3-methoxybenzamide
N-[(5-{[4-(heptylamino)azepan-1-yl]sulfonyl}thien-2-yl)methyl]-3-methoxybenzamide
3-methoxy-N-[(5-{[4-(octylamino)azepan-1-yl]sulfonyl}thien-2-yl)methyl]benzamide
3-methoxy-N-[(5-{[4-(pentylamino)azepan-1-yl]sulfonyl}thien-2-yl)methyl]benzamide
N-[(5-{[4-(butylamino)azepan-1-yl]sulfonyl}thien-2-yl)methyl]-3-methoxybenzamide
N-[(5-{[4-(dodecylamino)azepan-1-yl]sulfonyl}thien-2-yl)methyl]-3-methoxybenzamide
N-{[5-({4-[(2-cyclohexylethyl)amino]azepan-1-yl}sulfonyl)thien-2-yl]methyl}-3-methoxybenzamide
N-({5-[(4-{[(1R)-1-cyclohexylethyl]amino}azepan-1-yl)sulfonyl]thien-2-yl}methyl)-3-methoxybenzamide
N-({5-[(4-{[(1R,2R,4S)-bicyclo[2.2.1]hept-2-ylamino]azepan-1-yl}sulfonyl)thien-2-yl]methyl}-3-methoxybenzamide
3-methoxy-N-{[5-({4-[(2-propoxyethyl)amino]azepan-1-yl}sulfonyl)thien-2-yl]methyl}benzamide
N-{[5-({4-[(cyclohexylmethyl)amino]azepan-1-yl}sulfonyl)thien-2-yl]methyl}-3-methoxybenzamide
N-{[5-({4-[(1-adamantylmethyl)amino]azepan-1-yl}sulfonyl)thien-2-yl]methyl}-3-methoxybenzamide
3-methoxy-N-{[5-({4-[(3-morpholin-4-ylpropyl)amino]azepan-1-yl}sulfonyl)thien-2-yl]methyl}benzamide
3-methoxy-N-{[5-({4-[(2-pyridin-2-ylethyl)amino]azepan-1-yl}sulfonyl)thien-2-yl]methyl}benzamide
3-methoxy-N-{[5-({4-[(2-piperidin-1-ylethyl)amino]azepan-1-yl}sulfonyl)thien-2-yl]methyl}benzamide
N-{[5-({4-[(2-ethylhexyl)amino]azepan-1-yl}sulfonyl)thien-2-yl]methyl}-3-methoxybenzamide
N-({5-[(4-{[3-(1H-imidazol-1-yl)propyl]amino}azepan-1-yl)sulfonyl]thien-2-yl}methyl)-3-methoxybenzamide
4-chloro-N-[(5-{[4-(heptylamino)azepan-1-yl]sulfonyl}thien-2-yl)methyl]benzamide
4-chloro-N-[(5-{[4-(octylamino)azepan-1-yl]sulfonyl}thien-2-yl)methyl]benzamide
4-chloro-N-[(5-{[4-(pentylamino)azepan-1-yl]sulfonyl}thien-2-yl)methyl]benzamide
N-[(5-{[4-(butylamino)azepan-1-yl]sulfonyl}thien-2-yl)methyl]-4-chlorobenzamide
4-chloro-N-[(5-{[4-(dodecylamino)azepan-1-yl]sulfonyl}thien-2-yl)methyl]benzamide
4-chloro-N-{[5-({4-[(2-cyclohexylethyl)amino]azepan-1-yl}sulfonyl)thien-2-yl]methyl}benzamide
N-{[5-({4-[(1R,2R,4S)-bicyclo[2.2.1]hept-2-ylamino]azepan-1-yl}sulfonyl)thien-2-yl]methyl}-4-chlorobenzamide
4-chloro-N-{[5-({4-[(2-propoxyethyl)amino]azepan-1-yl}sulfonyl)thien-2-yl]methyl}benzamide
4-chloro-N-{[5-({4-[(2-ethylhexyl)amino]azepan-1-yl}sulfonyl)thien-2-yl]methyl}benzamide
4-chloro-N-[(5-{[4-(hexylamino)azepan-1-yl]sulfonyl}thien-2-yl)methyl]benzamide
N-[(5-{[4-(hexylamino)azepan-1-yl]sulfonyl}thien-2-yl)methyl]-3-methoxybenzamide
3-methoxy-N-[(5-{[4-({2-[3-(trifluoromethyl)phenyl]ethyl}amino)piperidin-1-yl]sulfonyl}thien-2-yl)methyl]benzamide
3-methoxy-N-({5-[(4-{[2-(4-methylphenyl)ethyl]amino}piperidin-1-yl)sulfonyl]thien-2-yl}methyl)benzamide
3-methoxy-N-({5-[(4-{[(1S,2R)-2-phenylcyclopropyl]amino}piperidin-1-yl)sulfonyl]thien-2-yl}methyl)benzamide
3-methoxy-N-{[5-({4-[(1-naphthylmethyl)amino]piperidin-1-yl}sulfonyl)thien-2-yl]methyl}benzamide
3-methoxy-N-{[5-({4-[(2-phenylpropyl)amino]piperidin-1-yl}sulfonyl)thien-2-yl]methyl}benzamide
N-({5-[(4-{[2-(4-hydroxyphenyl)ethyl]amino}piperidin-1-yl)sulfonyl]thien-2-yl}methyl)-3-methoxybenzamide
3-methoxy-N-{[5-({4-[(3-phenylpropyl)amino]piperidin-1-yl}sulfonyl)thien-2-yl]methyl}benzamide
N-{[5-({4-[(2,3-dihydroxypropyl)amino]piperidin-1-yl}sulfonyl)thien-2-yl]methyl}-3-methoxybenzamide
N-{[5-({4-[(2-hydroxyethyl)amino]piperidin-1-yl}sulfonyl)thien-2-yl]methyl}-3-methoxybenzamide
3-methoxy-N-[(5-{[4-(nonylamino)piperidin-1-yl]sulfonyl}thien-2-yl)methyl]benzamide
3-methoxy-N-[(5-{[4-(decylamino)piperidin-1-yl]sulfonyl}thien-2-yl)methyl]benzamide
3-methoxy-N-[(5-{[4-(ethylamino)piperidin-1-yl]sulfonyl}thien-2-yl)methyl]benzamide
N-{[5-({4-[(2-[1,1'-biphenyl]-4-ylethyl)amino]piperidin-1-yl}sulfonyl)thien-2-yl]methyl}-3-methoxybenzamide
N-{[5-({4-[([1,1'-biphenyl]-3-ylmethyl)amino]piperidin-1-yl}sulfonyl)thien-2-yl]methyl}-3-methoxybenzamide
3-methoxy-N-{[5-({4-[(2-thien-2-ylethyl)amino]piperidin-1-yl}sulfonyl)thien-2-yl]methyl}benzamide
3-methoxy-N-[(5-{[4-({4-[(trifluoromethyl)sulfonyl]benzyl}amino)piperidin-1-yl]sulfonyl}thien-2-yl)methyl]benzamide
3-methoxy-N-{[5-(f{4-[(quinolin-4-ylmethyl)amino]piperidin-1-yl}sulfonyl)thien-2-yl]methyl}benzamide
N-{[5-({4-[([1,1'-biphenyl]-4-ylmethyl)amino]-1-piperidinyl}sulfonyl)-2-thienyl]methyl}-3-methoxybenzamide
4-chloro-N-{[5-({4-[(2-{[(trifluoromethyl)sulfonyl]amino}ethyl)amino]-1-piperidinyl}sulfonyl)-2-thienyl]methyl}benzamide
4-chloro-N-[(5-{[4-(propylamino)-1-piperidinyl]sulfonyl}-2-thienyl)methyl]benzamide
4-chloro-N-[(5-{[4-({4-[(trifluoromethyl)sulfonyl]benzyl}amino)-1-piperidinyl]sulfonyl}-2-thienyl)methyl]benzamide
4-chloro-N-{[5-({4-[(3,4-dihydroxybenzyl)amino]-1-piperidinyl}sulfonyl)-2-thienyl]methyl}benzamide
methyl[{1-[(5-{[(4-chlorobenzoyl)amino]methyl}-2-thienyl)sulfonyl]-4-piperidinyl}(hexyl)amino]acetate
tert-butyl[{1-[(5-{[(4-chlorobenzoyl)amino]methyl}-2-thienyl)sulfonyl]-4-piperidinyl}(hexyl)amino]acetate
[{1-[(5-{[(4-chlorobenzoyl)amino]methyl}-2-thienyl)sulfonyl]-4-piperidinyl}(hexyl)amino]acetic acid
N-[(5-{[3-(heptylamino)pyrrolidin-1-yl]sulfonyl}thien-2-yl)methyl]-3-methoxybenzamide
3-methoxy-N-[(5-{[3-(octylamino)pyrrolidin-1-yl]sulfonyl}thien-2-yl)methyl]benzamide
3-methoxy-N-[(5-{[3-(pentylamino)pyrrolidin-1-yl]sulfonyl}thien-2-yl)methyl]benzamide
N-[(5-{[3-(butylamino)pyrrolidin-1-yl]sulfonyl}thien-2-yl)methyl]-3-methoxybenzamide
N-[(5-{[3-(dodecylamino)pyrrolidin-1-yl]sulfonyl}thien-2-yl)methyl]-3-methoxybenzamide
N-{[5-({3-[(2-cyclohexylethyl)amino]pyrrolidin-1-yl}sulfonyl)thien-2-yl]methyl}-3-methoxybenzamide
N-({5-[(3-{[(1R)-1-cyclohexylethyl]amino}pyrrolidin-1-yl)sulfonyl]thien-2-yl}methyl)-3-methoxybenzamide N-{[5-({3-[(1R,2R,4S)-bicyclo[2.2.1]hept-2-ylamino]pyrrolidin-1-yl}sulfonyl)thien-2-yl]methyl}-3-methoxybenzamide
3-methoxy-N-{[5-({3-[(2-propoxyethyl)amino]pyrrolidin-1-yl}sulfonyl)thien-2-yl]methyl}benzamide
N-{[5-({3-[(cyclohexylmethyl)amino]pyrrolidin-1-yl}sulfonyl)thien-2-yl]methyl}-3-methoxybenzamide
N-{[5-({3-[(1-adamantylmethyl)amino]pyrrolidin-1-yl}sulfonyl)thien-2-yl]methyl}-3-methoxybenzamide
3-methoxy-N-{[5-({3-[(3-morpholin-4-ylpropyl)amino]pyrrolidin-1-yl}sulfonyl)thien-2-yl]methyl}benzamide
3-methoxy-N-{[5-({3-[(2-pyridin-2-ylethyl)amino]pyrrolidin-1-yl}sulfonyl)thien-2-yl]methyl}benzamide
3-methoxy-N-{[5-({3-[(2-piperidin-1-ylethyl)amino]pyrrolidin-1-yl}sulfonyl)thien-2-yl]methyl}benzamide
N-{[5-({3-[(2-ethylhexyl)amino]pyrrolidin-1-yl}sulfonyl)thien-2-yl]methyl}-3-methoxybenzamide
N-[(5-{[3-(hexylamino)pyrrolidin-1-yl]sulfonyl}thien-2-yl)methyl]-3-methoxybenzamide
4-chloro-N-[(5-{[3-(heptylamino)pyrrolidin-1-yl]sulfonyl}thien-2-yl)methyl]benzamide
4-chloro-N-[(5-{[3-(hexylamino)pyrrolidin-1-yl]sulfonyl}thien-2-yl)methyl]benzamide
4-chloro-N-[(5-{[3-(pentylamino)pyrrolidin-1-yl]sulfonyl}thien-2-yl)methyl]benzamide
N-[(5-{[3-(butylamino)pyrrolidin-1-yl]sulfonyl}thien-2-yl)methyl]-4-chlorobenzamide
4-chloro-N-{[5-({3-[(2-cyclohexylethyl)amino]pyrrolidin-1-yl}sulfonyl)thien-2-yl]methyl}benzamide
N-{[5-({3-[(1R,2R,4S)-bicyclo[2.2.1]hept-2-ylamino]pyrrolidin-1-yl}sulfonyl)thien-2-yl]methyl}-4-chlorobenzamide
4-chloro-N-({5-[(3-{[(1-hydroxycyclohexyl)methyl]amino}pyrrolidin-1-yl)sulfonyl]thien-2-yl}methyl)benzamide
N-{[5-({3-[(1-adamantylmethyl)amino]pyrrolidin-1-yl}sulfonyl)thien-2-yl]methyl}-4-chlorobenzamide
4-chloro-N-{[5-({3-[(3-morpholin-4-ylpropyl)amino]pyrrolidin-1-yl}sulfonyl)thien-2-yl]methyl}benzamide
4-chloro-N-{[5-({3-[(2-pyridin-2-ylethyl)amino]pyrrolidin-1-yl}sulfonyl)thien-2-yl]methyl}benzamide
4-chloro-N-{[5-({3-[(2-piperidin-1-ylethyl)amino]pyrrolidin-1-yl}sulfonyl)thien-2-yl]methyl}benzamide
4-chloro-N-{[5-({3-[(2-ethylhexyl)amino]pyrrolidin-1-yl}sulfonyl)thien-2-yl]methyl}benzamide
4-chloro-N-[(5-{[3-(octylamino)pyrrolidin-1-yl]sulfonyl}thien-2-yl)methyl]benzamide
methyl (2S)-1-[(5-{[(4-chlorobenzoyl)amino]methyl}-2-thienyl)sulfonyl]-4-(hexylamino)-2-pyrrolidinecarboxylate
3-methoxy-N-{[5-({4-[(pentylamino)methyl]piperidin-1-yl}sulfonyl)thien-2-yl]methyl}benzamide
N-{[5-({4-[2-(butylamino)ethyl]piperidin-1-yl}sulfonyl)thien-2-yl]methyl}-3-methoxybenzamide
N-{[5-({4-[(4-butylanilino)methyl]-1-piperidinyl}sulfonyl)-2-thienyl]methyl}-3-methoxybenzamide
4-chloro-N-{[5-({4-[hexyl(methyl)amino]piperidin-1-yl}sulfonyl)thien-2-yl]methyl}benzamide
4-chloro-N-{[5-(f{4-[(cyclohexylmethyl)(hexyl)amino]piperidin-1-yl}sulfonyl)thien-2-yl]methyl}benzamide
N-{[5-({4-[benzyl(hexyl)amino]piperidin-1-yl}sulfonyl)thien-2-yl]methyl}-4-chlorobenzamide
4-chloro-N-{[5-({4-[hexyl(pyridin-3-ylmethyl)amino]piperidin-1-yl}sulfonyl)thien-2-yl]methyl}benzamide
4-chloro-N-{[5-({4-[hexyl(pyridin-4-ylmethyl)amino]piperidin-1-yl}sulfonyl)thien-2-yl]methyl}benzamide
4-chloro-N-{[5-({4-[hexyl(pyridin-2-ylmethyl)amino]piperidin-1-yl}sulfonyl)thien-2-yl]methyl}benzamide
N-{[5-({4-[butyl(hexyl)amino]piperidin-1-yl}sulfonyl)thien-2-yl]methyl}-4-chlorobenzamide
4-chloro-N-{[5-({4-[hexyl(3-phenylpropyl)amino]piperidin-1-yl}sulfonyl)thien-2-yl]methyl}benzamide
4-chloro-N-{[5-({4-[hexyl(2-phenylethyl)amino]piperidin-1-yl}sulfonyl)thien-2-yl]methyl}benzamide
N-{[5-({4-[[(5-bromo-2-furyl)methyl](hexyl)amino]piperidin-1-yl}sulfonyl)thien-2-yl]methyl}-4-chlorobenzamide
3-methoxy-N-({5-[(4-{methyl[4-(trifluoromethyl)benzyl]amino}-1-piperidinyl)sulfonyl]-2-thienyl}methyl)benzamide
4-chloro-N-{[5-({4-[(3-chlorobenzyl)amino]piperidin-1-yl}sulfonyl)thien-2-yl]methyl}benzamide
3-methoxy-N-({5-[(4-{[4-(trifluoromethyl)benzyl]amino}piperidin-1-yl)sulfonyl]thien-2-yl}methyl)benzamide
3-methoxy-N-{[5-({4-[(3-methylbenzyl)amino]piperidin-1-yl}sulfonyl)thien-2-yl]methyl}benzamide
3-methoxy-N-{[5-({4-[(4-propylbenzyl)amino]piperidin-1-yl}sulfonyl)thien-2-yl]methyl}benzamide
3-methoxy-N-({5-[(4-{[3-(trifluoromethyl)benzyl]amino}piperidin-1-yl)sulfonyl]thien-2-yl}methyl)benzamide
3-methoxy-N-({5-[(4-{[4-(trifluoromethoxy)benzyl]amino}piperidin-1-yl)sulfonyl]thien-2-yl}methyl)benzamide
N-({5-[(4-{[4-(difluoromethoxy)benzyl]amino}piperidin-1-yl)sulfonyl]thien-2-yl}methyl)-3-methoxybenzamide
3-methoxy-N-{[5-({4-[(2,3,4,5,6-pentamethylbenzyl)amino]piperidin-1-yl}sulfonyl)thien-2-yl]methyl}benzamide
3-methoxy-N-{[5-({4-[(4-propoxybenzyl)amino]piperidin-1-yl}sulfonyl)thien-2-yl]methyl}benzamide
N-{[5-({4-[(4-butoxybenzyl)amino]piperidin-1-yl}sulfonyl)thien-2-yl]methyl}-3-methoxybenzamide
3-methoxy-N-{[5-({4-[(4-methoxybenzyl)amino]piperidin-1-yl}sulfonyl)thien-2-yl]methyl}benzamide
3-methoxy-N-{[5-({4-[(pyridin-4-ylmethyl)amino]piperidin-1-yl}sulfonyl)thien-2-yl]methyl}benzamide
3-methoxy-N-{[5-({4-[(pyridin-2-ylmethyl)amino]piperidin-1-yl}sulfonyl)thien-2-yl]methyl}benzamide
3-methoxy-N-{[5-({4-[(pyridin-3-ylmethyl)amino]piperidin-1-yl}sulfonyl)thien-2-yl]methyl}benzamide
N-{[5-({4-[(4-tert-butylbenzyl)amino]piperidin-1-yl}sulfonyl)thien-2-yl]methyl}-3-methoxybenzamide
N-{[5-({4-[(3-ethoxybenzyl)amino]piperidin-1-yl}sulfonyl)thien-2-yl]methyl}-3-methoxybenzamide
3-methoxy-N-{[5-({4-[(4-phenoxybenzyl)amino]piperidin-1-yl}sulfonyl)thien-2-yl]methyl}benzamide
3-methoxy-N-[(5-{[4-({4-[(trifluoromethyl)sulfanyl]benzyl}amino)piperidin-1-yl]sulfonyl}thien-2-yl)methyl]benzamide
3-methoxy-N-({5-[(4-{[4-(methylsulfonyl)benzyl]amino}-1-piperidinyl)sulfonyl]-2-thienyl}methyl)benzamide
N-({5-[(4-{[3,5-bis(trifluoromethyl)benzyl]amino}-1-piperidinyl)sulfonyl]-2-thienyl}methyl)-3-methoxybenzamide
N-({5-[(4-{[2,5-bis(trifluoromethyl)benzyl]amino}-1-piperidinyl)sulfonyl]-2-thienyl}methyl)-3-methoxybenzamide
N-({5-[(4-{[4-(ethylsulfanyl)benzyl]amino}-1-piperidinyl)sulfonyl]-2-thienyl}methyl)-3-methoxybenzamide
3-methoxy-N-[(5-{[4-({3-[(trifluoromethyl)sulfanyl]benzyl}amino)-1-piperidinyl]sulfonyl}-2-thienyl)methyl]benzamide N-({5-[(4-{[(2,2-difluoro-1,3-benzodioxol-5-yl)methyl] amino}-1-piperidinyl)sulfonyl]-2-thienyl}methyl)-3-methoxybenzamide N-{[5-({4-[(4-iodobenzyl)amino]-1-piperidinyl}sulfonyl)-2-thienyl]methyl}-3-methoxybenzamide N-({5-[(4-{[4-(benzyloxy)benzyl]amino}-1-piperidinyl) sulfonyl]-2-thienyl}methyl)-3-methoxybenzamide N-{[5-({4-[(mesitylmethyl)amino]-1-piperidinyl}sulfonyl)-2-thienyl]methyl}-3-methoxybenzamide N-{[5-({4-[(4-chlorobenzyl)amino]-1-piperidinyl}sulfonyl)-2-thienyl]methyl}-3-methoxybenzamide N-{[5-({4-[(4-ethylbenzyl)amino]-1-piperidinyl}sulfonyl)-2-thienyl]methyl}-3-methoxybenzamide 3-methoxy-N-{[5-({4-[(4-pentylbenzyl)amino]-1-piperidinyl}sulfonyl)-2-thienyl]methyl}benzamide 3-methoxy-N-[(5-{[4-({1-[4-(trifluoromethyl)phenyl] ethyl}amino)-1-piperidinyl]sulfonyl}-2-thienyl)methyl] benzamide 3-methoxy-N-{[5-({4-[(4-methylbenzyl)amino]-1-piperidinyl}sulfonyl)-2-thienyl]methyl}benzamide N-{[5-({4-[(4-butylbenzyl)amino]-1-piperidinyl}sulfonyl)-2-thienyl]methyl}-3-methoxybenzamide N-{[5-({4-[(4-isopropylbenzyl)amino]-1-piperidinyl}sulfonyl)-2-thienyl]methyl}-3-methoxybenzamide N-{[5-({4-[(4-isobutylbenzyl)amino]-1-piperidinyl}sulfonyl)-2-thienyl]methyl}-3-methoxybenzamide N-({5-[(4-{[(1-hydroxy-1lambda~5~-pyridin-4-yl)methyl] amino}-1-piperidinyl)sulfonyl]-2-thienyl}methyl)-3-methoxybenzamide N-{[5-({4-[(2,3-dihydro-1,4-benzodioxin-6-ylmethyl) amino]-1-piperidinyl}sulfonyl)-2-thienyl]methyl}-3-methoxybenzamide N-{[5-({4-[(2,3-dihydro-1-benzofuran-5-ylmethyl)amino]-1-piperidinyl}sulfonyl)-2-thienyl]methyl}-3-methoxybenzamide 4-chloro-N-{[5-({4-[(4-propylbenzyl)amino]-1-piperidinyl}sulfonyl)-2-thienyl]methyl}benzamide 4-chloro-N-({5-[(4-{[4-(trifluoromethoxy)benzyl]amino}-1-piperidinyl)sulfonyl]-2-thienyl}methyl)benzamide 4-chloro-N-({5-[(4-{[4-(difluoromethoxy)benzyl]amino}-1-piperidinyl)sulfonyl]-2-thienyl}methyl)benzamide 4-chloro-N-{[5-({4-[(4-propoxybenzyl)amino]-1-piperidinyl}sulfonyl)-2-thienyl]methyl}benzamide N-{[5-({4-[(4-butoxybenzyl)amino]-1-piperidinyl}sulfonyl)-2-thienyl]methyl}-4-chlorobenzamide 4-chloro-N-{[5-({4-[(4-quinolinylmethyl)amino]-1-piperidinyl}sulfonyl)-2-thienyl]methyl}benzamide N-{[5-({4-[(4-tert-butylbenzyl)amino]-1-piperidinyl}sulfonyl)-2-thienyl]methyl}-4-chlorobenzamide 4-chloro-N-{[5-({4-[(4-phenoxybenzyl)amino]-1-piperidinyl}sulfonyl)-2-thienyl]methyl}benzamide 4-chloro-N-[(5-{[4-({4-[(trifluoromethyl)sulfanyl] benzyl}amino)-1-piperidinyl]sulfonyl}-2-thienyl)methyl] benzamide 4-chloro-N-({5-[(4-{[4-(trifluoromethyl)benzyl]amino}-1-piperidinyl)sulfonyl]-2-thienyl}methyl)benzamide 3-methoxy-N-({5-[(4-{[2-(trifluoromethyl)benzyl]amino}-1-piperidinyl)sulfonyl]-2-thienyl}methyl)benzamide 3-methoxy-N-[(5-{[4-({[6-(trifluoromethyl)-3-pyridinyl] methyl}amino)-1-piperidinyl]sulfonyl}-2-thienyl)methyl]benzamide N-[(5-{[4-(benzylamino)-1-piperidinyl]sulfonyl}-2-thienyl) methyl]-3-methoxybenzamide 3-methoxy-N-[(5-{[4-({1-[4-(trifluoromethyl)phenyl] propyl}amino)-1-piperidinyl]sulfonyl}-2-thienyl)methyl] benzamide 3-methoxy-N-[(5-{[4-({1-methyl-1-[4-(trifluoromethyl) phenyl]ethyl}amino)-1-piperidinyl]sulfonyl}-2-thienyl) methyl]benzamide 4-chloro-N-[(5-{[4-(f{1-[4-(trifluoromethyl)phenyl] ethyl}amino)-1-piperidinyl]sulfonyl}-2-thienyl)methyl] benzamide 4-chloro-N-[(5-{[4-({1-methyl-1-[4-(trifluoromethyl)phenyl]ethyl}amino)-1-piperidinyl]sulfonyl}-2-thienyl)methyl]benzamide 4-chloro-N-[(5-{[2-({[4-(trifluoromethyl)benzyl] amino}methyl)-1-pyrrolidinyl]sulfonyl}-2-thienyl)methyl]benzamide 4-chloro-N-[(5-{[(3R)-3-({[4-(trifluoromethyl)benzyl] amino}methyl)pyrrolidinyl]sulfonyl}-2-thienyl)methyl] benzamide 4-chloro-N-({5-[(3-{[4-(trifluoromethyl)benzyl]amino}-1-piperidinyl)sulfonyl]-2-thienyl}methyl)benzamide 4-chloro-N-{[5-({3-[(hexylamino)methyl]-1-piperidinyl}sulfonyl)-2-thienyl]methyl}benzamide 4-chloro-N-({5-[(3-{[4-(trifluoromethyl)benzyl]amino}-1-pyrrolidinyl)sulfonyl]-2-thienyl}methyl)benzamide 4-chloro-N-{[5-({(3R)-3-[(hexylamino)methyl] pyrrolidinyl}sulfonyl)-2-thienyl]methyl}benzamide 4-chloro-N-[(5-{[3-({[4-(trifluoromethyl)benzyl] amino}methyl)-1-piperidinyl]sulfonyl}-2-thienyl)methyl]benzamide 2-oxo-N-({5-[(4-{[4-(trifluoromethyl)benzyl]amino}-1-piperidinyl)sulfonyl]-2-thienyl}methyl)-1,2-dihydro-3-pyridinecarboxamide N-[(5-{[4-(hexylamino)-1-piperidinyl]sulfonyl}-2-thienyl) methyl]-2-oxo-1,2-dihydro-3-pyridinecarboxamide N-[(5-{[4-(hexylamino)-1-piperidinyl]sulfonyl}-2-thienyl) methyl]-2-hydroxybenzamide 2-hydroxy-N-({5-[(4-{[4-(trifluoromethyl)benzyl]amino}-1-piperidinyl)sulfonyl]-2-thienyl}methyl)benzamide N-[(5-{[4-(hexylamino)-1-piperidinyl]sulfonyl}-2-thienyl) methyl]-2-thioxo-1,2-dihydro-3-pyridinecarboxamide 2-thioxo-N-({5-[(4-{[4-(trifluoromethyl)benzyl]amino}-1-piperidinyl)sulfonyl]-2-thienyl}methyl)-1,2-dihydro-3-pyridinecarboxamide N-[(5-{[4-(butylamino)-1-piperidinyl]sulfonyl}-2-thienyl) methyl]-2-oxo-1,2-dihydro-3-pyridinecarboxamide N-({5-[(4-{ethyl[4-(trifluoromethyl)benzyl]amino}-1-piperidinyl)sulfonyl]-2-thienyl}methyl)-3-methoxybenzamide 4-chloro-N-[(5-{[4-({imino[4-(trifluoromethyl)phenyl] methyl}amino)-1-piperidinyl]sulfonyl}-2-thienyl)methyl]benzamide 1-[(5-{[(4-chlorobenzoyl)amino]methyl}-2-thienyl)sulfonyl]-4-(hexylamino)proline ethyl 2-{[4-(hexylamino)piperidin-1-yl]sulfonyl}-5-{[(3-methoxybenzoyl)amino]methyl}thiophene-3-carboxylate N-{[5-{[4-(hexylamino)piperidin-1-yl]sulfonyl}-4-(trimethylsilyl)thien-2-yl]methyl}-3-methoxybenzamide N-({5-{[4-(hexylamino)piperidin-1-yl]sulfonyl}-4-[hydroxy(phenyl)methyl]thien-2-yl}methyl)-3-methoxybenzamide 5-[(3-Methoxy-benzoylamino)-methyl]-2-[4-(4-trifluoromethyl-benzylamino)-piperidine-1-sulfonyl]-thiophene-3-carboxylic acid ethyl ester N-[(4-chloro-5-{[4-(hexylamino)piperidin-1-yl] sulfonyl}thien-2-yl)methyl]-3-methoxybenzamide.

The compounds of formula (III) may be obtained according to the methods described in any of WO 01/23378, WO 02/28856 and WO 02/26733.

In a further embodiment the JNK inhibitors may be a pyrazoloanthrone derivative as shown in formula (C) (WO 01/12609):

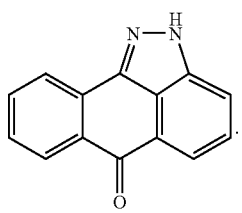

(C)

In a further embodiment the JNK inhibitors may have the formula (IV) (WO 03/018022):

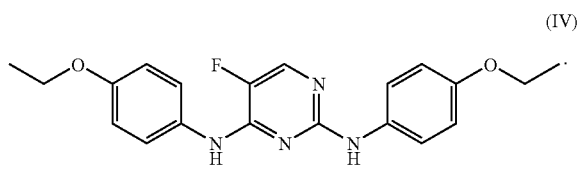 [SMILES: CCOc1ccc(Nc2ncc(F)c(Nc3ccc(OCC)cc3)n2)cc1]

(IV)

The present invention will now be illustrated by the example, which is not intended to be limiting in any way.

EXAMPLES

Example 1

Models for Endometriosis

The effect of the JNK inhibitor was evaluated in both in vitro and in vivo models of endometriosis. The efficacy of the drug treatment in inhibiting endometriosis was tested in two in vivo models, i) nude mouse model and ii) the rat model and an in vitro proliferative organ culture model.

Example 1.1

N-Cadherin Expression

Figure 1:
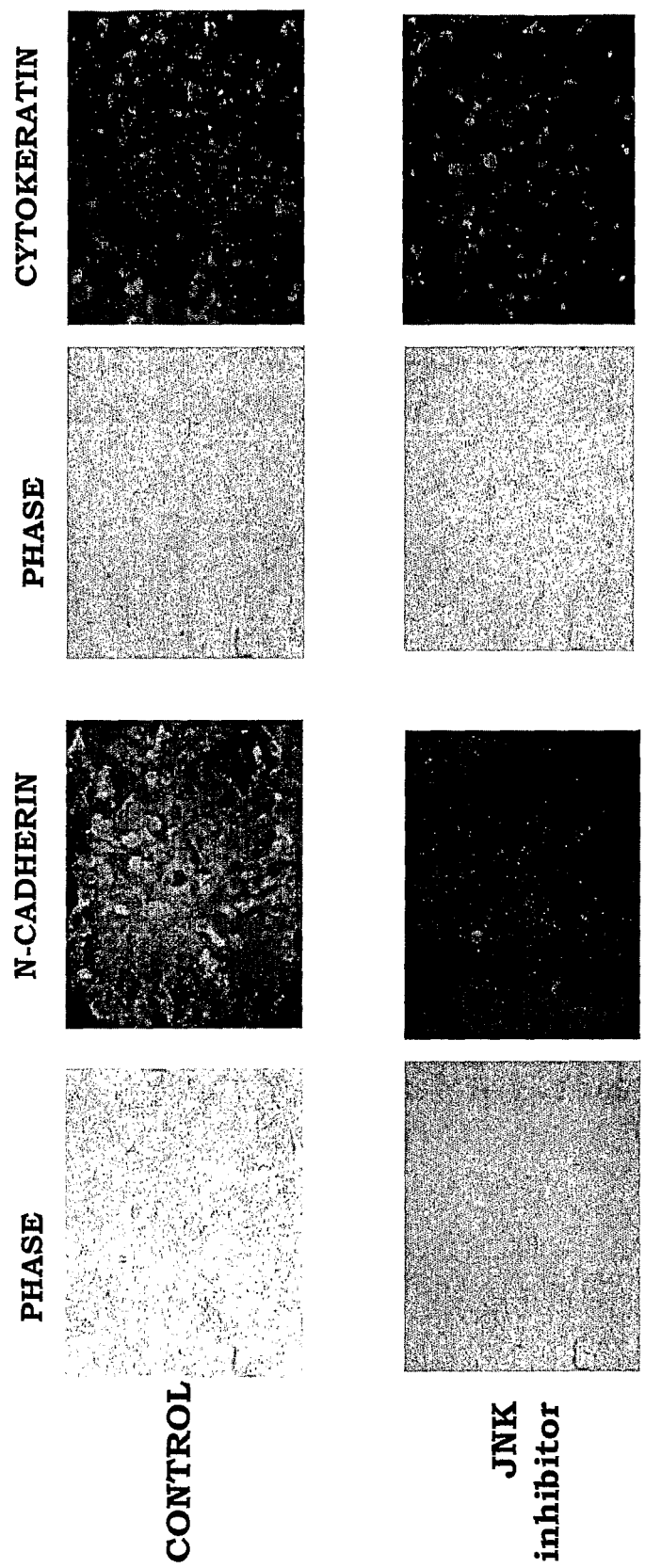
FIG. 1: Expression of N-cadherin and cytokeratin in endometriotic cells (12Z). Cells treated with JNK inhibitor were fixed with paraformaldehyde and stained for N-cadherin and cytokeratin. Cells were observed under fluorescent microscope (phase contrast and fluorescence pictures). Treating cells with a JNK inhibitor decreased the expression of N-cadherin. The expression of cytokeratin was not altered after treatment with the JNK inhibitor.

For in vitro studies, human endometriotic cells (12Z) were used (Zeitvogel et al 2001). These cells are invasive and express N-cadherin, whereas less invasive cells have lower levels of N-cadherin. These cells were treated with the JNK inhibitor and cells were fixed with paraformaldehyde. Fixed cells were stained for N-cadherin and cytokeratin using specific antibodies against these proteins, followed by second antibody conjugated to Alexafluor (a fluorochrome). Cells were observed under fluorescent microscope and both phase contrast and fluorescent pictures were taken. FIG. 1 represents the expression patterns of cytokeratin and N-cadherin in these cells. Treating cells with the JNK inhibitor decreased the expression of N-cadherin (FIG. 1), showing that this pathway is involved in the regulation of N-cadherin expression and invasive activity of endometriosis. On the other hand, expression of cytokeratin, a marker for epithelial cells was not altered following the treatment with the compound (FIG. 1). This shows that only endometriotic cells are affected by treatment with the JNK inhibitor, whereas epithelial cells are not affected. Thus, by blocking the JNK pathway, the invasive properties associated with endometriosis can be specifically inhibited and thus be very useful for treating endometriosis.

Example 1.2

Nude Mouse Model

Human endometrial tissue was injected in ovarectomized nude mice to establish the disease (Bruner-Tran et al 2002). In brief, endometrial biopsies obtained from normal volunteers or from endometriotic patients were cut into small pieces and cultured in the presence of estradiol for 24 h. Treated tissues, were injected either subcutaenously or intraperitoneally into ovarectomized nude mice with estradiol implant. Within 2-4 days of injection, ectopic endometriotic lesions developed in animals. Treatment with either progesterone or a JNK inhibitor was started 10-12 days following the injection of tissue. The compound was administered at a dose of 10 mg/kg and 30 mg/kg/animal for 30 days. Earlier work using this model has established that progesterone treatment prevents disease progression, hence this was used as control. Following the completion of treatment, animals were sacrificed, lesions developed from the transplanted tissue found in both subcutaneous and intraperitoneal sites, were measured (both size and number).

Table 1 below, illustrates the results of studies carried out as described above. The JNK inhibitor at a dose of 30 mg/kg was effective in regressing the established disease in 50% animals compared to progesterone treatment. The mean lesion size was also reduced by 20% by the treatment. In another experiment conducted with TBP, about 60% reduction in number of animals having the disease was observed compared to the positive control, progesterone, without any effect on lesion size. These results are significant, since the model measures the growth/regression of human endometrial tissue and thus has a direct relevance for treating the human disease.

TABLE 1

Effects of JNK inhibitors (a JNK inhibitor of formula I) and protein immunomodulatory agents on regression of endometriotic lesions in the nude mouse xenograft model.

| Treatment | Lesion (% Progesterone) Compared to progesterone treated group | Lesion size |
| --- | --- | --- |
| JNK inhibitor 30 mg/kg × 30 days | 50% Decrease | 20% Decrease |
| TBP-1 (control) 5 mg/kg × 30 days | 60% Decrease | No change |

In another experiment in nude mice, human endometrial tissue was obtained from endometriotic patients, and cultured in the presence of either estradiol alone, estradiol plus medroxy progesterone acetate (MPA) or JNK inhibitor for 24 h. Treated tissues were then injected either subcutaneously or intraperitoneally into ovarectomized mice with estradiol implant. Within 2-4 days of injection, ectopic endometriotic lesions developed in animals. At 10-12 days following injection of tissue, treatment was begun with either MPA alone, JNK inhibitor alone or MPA plus JNK inhibitor. The JNK inhibitor was administered at a dose of 30/mg/kg/animal for 30 days. Following the completion of treatment, animals were sacrificed, lesions developed from the transplanted tissue found in both subcutaneous and intraperitoneal sites were measured in both size and number. Treatment with a combination of MPA and JNK inhibitor of formula 1 led to a reduction in the lesion load of approximately 50% with a reduction in lesion size of about 15 to 30% as compared to the lesion load and size of those treated with estradiol alone. These results indicate that the combination of a JNK inhibitor of formula 1 in combination with a progestin would be effective in treating and/or preventing endometriosis.

Example 1.3

Rat Model

Figure 2:
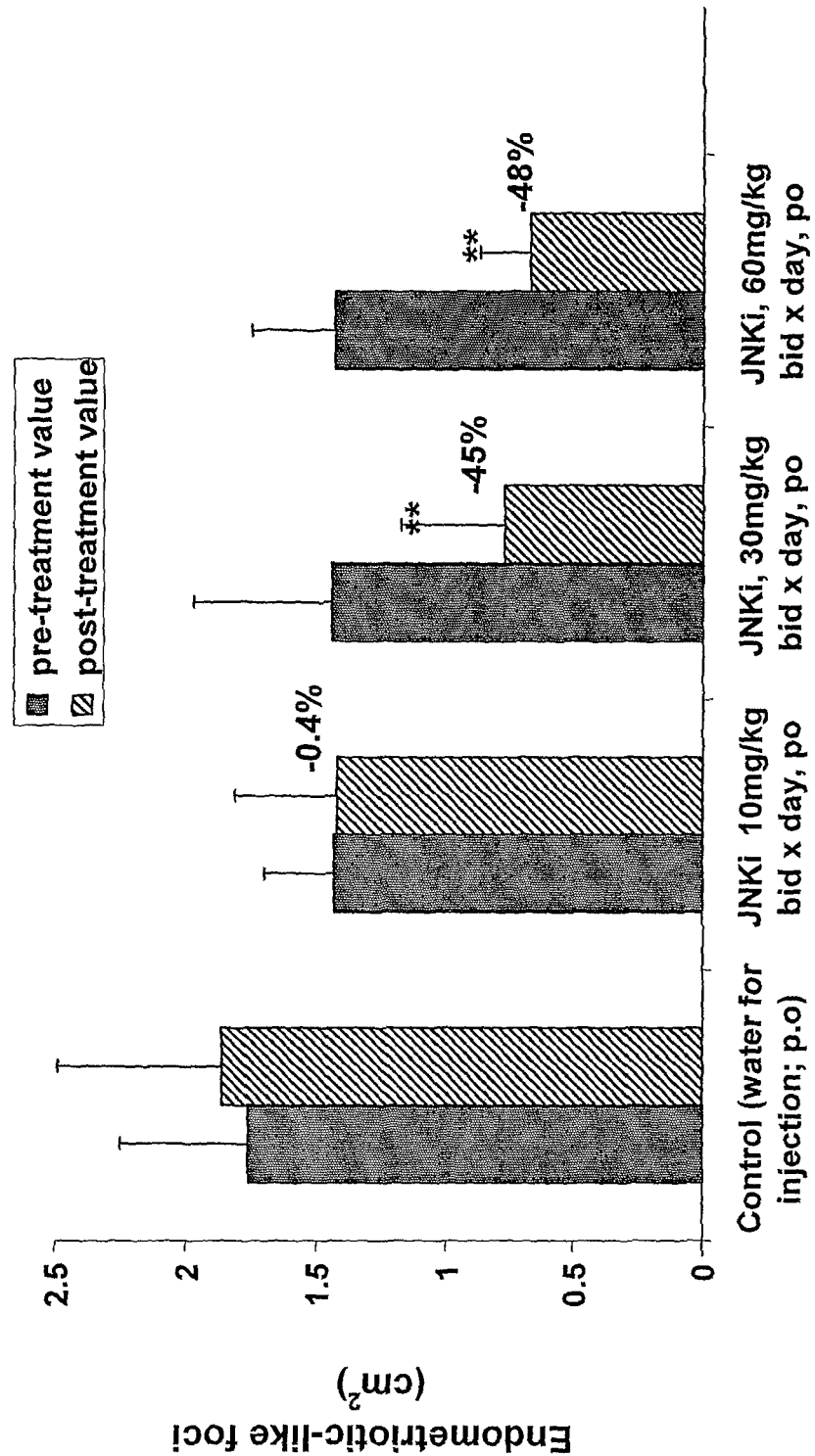
FIG. 2: Effect of a JNK inhibitor on the growth of endometriotic-like foci in experimentally induced endometriosis in rats. The effect of the JNK inhibitor given at a dose of 10 mg/kg was not different from the vehicle. 30 mg/kg and 60 mg/kg doses showed a significant regression of established endometriotic lesions.

Endometriosis was induced in rats as described earlier (D'Antonio et al 2000). In brief, autologous uterine horn fragment was transplanted onto the inner surface of the abdominal wall in rat. Three weeks following transplantation, the size and the viability of the engrafted tissue was measured. One week after the confirmation of the tissue attachment, treatments were started. The control group received the vehicle only. The JNK inhibitor was administered orally (po) at doses of 10 mg/kg and 30 mg/kg per day. Treatment with JNK inhibitor was conducted for nine days, animals were anaesthetized 2 hr following the last treatment and blood samples were collected. Surface area of the endometriosis-like foci was measured, endometriotic-like foci flushed with PBS and contralateral uterine flushing was also collected for measuring cytokine. The endometriotic-like foci and spleen was removed for histology and for NK cell activity measurement respectively. In this model, the effect of the JNK inhibitor at 10 mg/kg dose was not different from the vehicle, but at 30 mg/kg and 60 mg/kg a significant regression of established endometriotic lesions was observed (FIG. 2). Treatment with antide (for comparison) showed about 85% regression (data not shown).

Example 1.4

Rat Model/Determination of Cytokine Levels

Of additional significance from these recent studies are modifications in cytokine levels measured in either the endometriotic foci or in the contralateral uterine horn without any lesion. The effect of the JNK inhibitor on the cytokine levels was determined in the rat model (see Example 1.3). The results demonstrate that treatment with the JNK inhibitor reduced the levels of inflammatory cytokines, IL-12, INF-γ, IL-10 and MCP-1 in the endometriotic foci (FIG. 3). These cytokines have been previously reported to be elevated in peritoneal fluid of women with disease. In the contralateral horn, the JNK inhibitor was without effect on the cytokine expression (FIG. 4). In addition, inhibitor treatment increased NK cell activity compared to the vehicle treated group (FIG. 5). A reduced lymphocyte cytolytic activity has been observed in women with endometriosis. Therefore, these results suggest that an increase in the NK cell cytolytic activity due to the JNK inhibitor treatment may contribute to the elimination of ectopic endometrium. Further, these results with JNK inhibitors suggest that the effects of the inhibitor may treat the diseased tissue without affecting portions of the uterus or peritoneal cavity without disease.

The immune system of the rat in this model is intact, suggesting that if molecules had as a primary mechanism to affect only an immune-modulated pathway of the host, that the effects of the molecules in this model should have been stronger than observed in nude mice. In fact, these results from nude mouse and rat models suggest an important activity of the molecule directly on the endometriotic tissue or in immune cell populations that remain in nude mice. Another important distinction of the rat model is that intact myometrial and endometrial tissues are surgically resected into experimental animals. Taken together, results from these two model systems show that kinase inhibitors which target JNK pathway are involved in endometriosis and can be effective agents for treatment of disease.

Example 1.5

Proliferative Organ Culture Model

Normal endometrial tissues were acquired just prior to ovulation by biopsy from a donor population (no history of endometriosis) and from women with surgically confirmed endometriosis. Informed consent was obtained prior to biopsy and the use of human tissues was approved by Vanderbilt University's Institutional Review Board and Committee for the Protection of Human Subjects.

Endometrial biopsies were dissected into small cubes ($\sim 1\times 1$ mm$^3$) and 8-10 pieces of tissue per treatment group were suspended in tissue culture inserts. Organ cultures were maintained a total of 72 hrs at 37° C. in DME/F-12 media with serum supplements. Tissue treatments included 17β-estradiol (E), E plus progesterone (P), or E plus medroxy progesterone acetate (MPA) with and without the JNK inhibitor. Cultures were maintained for 24 hours in E only until the initiation of experimental conditions. JNK inhibitor was used at a concentration of 5 or 15 µM and MPA was used at a concentration of 50, 100 or 250 µM.

Media was collected from organ cultures and secreted proteins quantified using the Coomassie Plus Protein Assay (Pierce) and 20 µg total protein subjected to 10% SDS-PAGE. Proteins were transferred to PVDF membrane and blocked in PBS with 10% non-fat milk and 0.05% Tween-20. Blots were incubated overnight at 4° C. in PBS/Milk/Tween with a primary antibody recognizing human MMP-3, which is a marker for endometrial tissue, washed and incubated with secondary antibody for one hour. Proteins were visualized by chemiluminesence (Amersham) and autoradiography. As a negative control, identical blots were incubated without a primary antibody.

Results showed that the normal human endometrial cultures were sensitive to MPA treatment, in contrast to endometrial cultures obtained from endometriosis patients, which failed to regress with MPA alone. When a JNK inhibitor of formula 1 was combined with MPA treatment, the sensitivity to MPA was restored in the cultures obtained from endometriosis patients and maintained in the cultures obtained from normal volunteers.

These results indicate that co-administration of a progestin with a JNK inhibitor of formula 1 would treat and prevent the re-establishment of endometriosis.

REFERENCE LIST

Barcz et al., (2000) Med. Sci. Monit 6, 1042-46
Bruner-Tran et al., Ann NY Acad. Sci., 955:328-339 (2002)
Bulun et al., Mol. And Cell. Endocrinol., 248:94-103 (2006)
D'Antonio et al., J. Reprod Immunol. 48:81-98 (2000)
D'Hooghe et al., ASRM (2001)
Dawood, M. Y et al., (1993) Int. J. Gynaecol. Obstet. 40 (Suppl.), 29-42
Dent et al., (2003) Oncogene, 22, 5885-96
Gupta, S. et al., (1996) EMBO J. 15:2760-2770
Frixen et al., J. Cell Biology (1991) 113, 173-85
Giudice et al., (2004) Lancet 364, 1789-99

Kyama et al., (2003) Reprod Biol Endocrinol. 1, 123
Waller. et al., (1993) Fertil. Steril. 59, 511-515
Yoshino et al., (2004) Am J Reprod Immunol. 52, 306-11
Zeitvogel et al., (2001) Am. J Pathol. 159 1839-52
EP 160,699
EP 211,894
EP 322,438
WO 92/13095
WO 00/35909
WO 00/75118
WO 00/35906
WO 00/35920
WO 00/64872
WO 01/47920
WO 01/12621
WO 01/12609
WO 01/23378
WO 01/23379
WO 01/23382
WO 02/28856
WO 02/26733
WO 03/018022

The invention claimed is:

1. A method of treating endometriosis in an individual consisting essentially of administering a therapeutically effective amount of a JNK inhibitor; wherein the JNK inhibitor is a benzothiazole derivative according to formula (I)

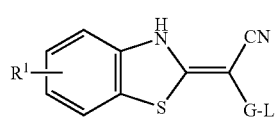

(I)

as well as its tautomers, its geometrical isomers, its optically active forms as enantiomers, diastereomers and its racemate forms, as well as pharmaceutically acceptable salts thereof, wherein:
G is a pyrimidinyl group;
L is selected from:

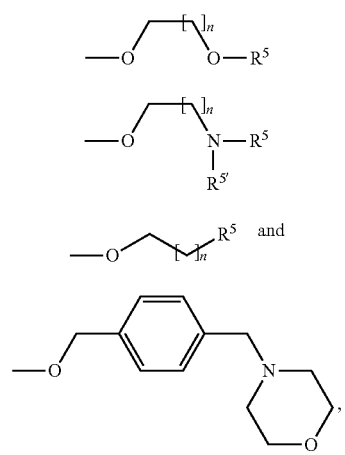

wherein n is 1 to 10;
$R^5$ and $R^{5'}$ are independently selected from each other from the group consisting of H, $C_1$-$C_{10}$ alkyl, aryl or heteroaryl, $C_1$-$C_6$ alkyl-aryl and $C_1$-$C_6$-alkyl-heteroaryl, wherein aryl is selected from the group consisting of phenyl, naphthyl and phenantrenyl, and hetero-aryl is selected from the group consisting of pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl and benzoquinolyl;
$R^1$ is selected from the group consisting of hydrogen, sulfonyl, amino, $C_1$-$C_6$-alkyl, $C_2$-$C_6$-alkenyl, $C_2$-$C_6$-alkynyl or $C_1$-$C_6$-alkoxy, aryl, halogen, cyano and hydroxy.

2. A method of treating endometriosis in an individual consisting essentially of sequentially or simultaneously administering a therapeutically effective amount of a JNK inhibitor in combination with a hormonal suppressor;
wherein the JNK inhibitor is a benzothiazole derivative according to formula (I)

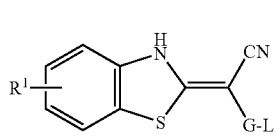

(I)

as well as its tautomers, its geometrical isomers, its optically active forms as enantiomers, diastereomers and its racemate forms, as well as pharmaceutically acceptable salts thereof, wherein:
G is a pyrimidinyl group;
L is selected from:

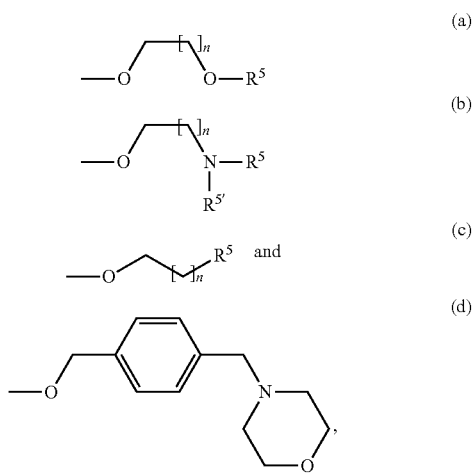

wherein n is 1 to 10;
$R^5$ and $R^{5'}$ are independently selected from each other from the group consisting of H, $C_1$-$C_{10}$ alkyl, aryl or heteroaryl, $C_1$-$C_6$ alkyl-aryl and $C_1$-$C_6$-alkyl-heteroaryl, wherein aryl is selected from the group consisting of phenyl, naphthyl and phenantrenyl, and hetero-aryl is selected from the group consisting of pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl, 1,3,4-triazinyl, 1,2,3- triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl and benzoquinolyl;

$R^1$ is selected from the group consisting of hydrogen, sulfonyl, amino, $C_1$-$C_6$-alkyl, $C_2$-$C_6$-alkenyl, $C_2$-$C_6$-alkynyl or $C_1$-$C_6$-alkoxy, aryl, halogen, cyano and hydroxy.

3. The method according to claim 2, wherein said hormonal suppressor is selected from the group consisting of a GnRH antagonist, GnRH agonist, aromatase inhibitor, progesterone receptor modulator and an estrogen receptor modulator.

4. A method of treating endometriosis in an individual consisting essentially of sequentially or simultaneously administering a therapeutically effective amount of a JNK inhibitor in combination with other fertility drugs for the treatment of endometriosis-related infertility;

wherein the JNK inhibitor is a benzothiazole derivative according to formula (I)

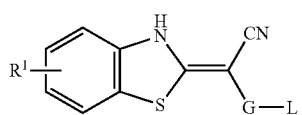

(I)

as well as its tautomers, its geometrical isomers, its optically active forms as enantiomers, diastereomers and its racemate forms, as well as pharmaceutically acceptable salts thereof, wherein:

G is a pyrimidinyl group;
L is selected from:

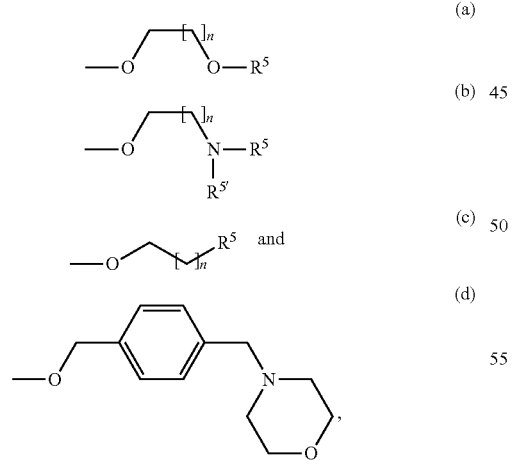

wherein n is 1 to 10;
$R^5$ and $R^{5'}$ are independently selected from each other from the group consisting of H, $C_1$-$C_{10}$ alkyl, aryl or heteroaryl, $C_1$-$C_6$ alkyl-aryl and $C_1$-$C_6$-alkyl-heteroaryl, wherein aryl is selected from the group consisting of phenyl, naphthyl and phenantrenyl, and hetero-aryl is selected from the group consisting of pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl and benzoquinolyl;

$R^1$ is selected from the group consisting of hydrogen, sulfonyl, amino, $C_1$-$C_6$-alkyl, $C_2$-$C_6$-alkenyl, $C_2$-$C_6$-alkynyl or $C_1$-$C_6$-alkoxy, aryl, halogen, cyano and hydroxy.

5. The method according to claim 1, wherein $R^1$ is H or $C_1$-$C_3$ alkyl.

6. The method according to claim 1 wherein the JNK inhibitor is: 1,3-benzothiazol-2-yl(2-{[4-(morpholin-4-ylmethyl)benzyl]oxy}pyrimidin-4-yl)acetonitrile, or a pharmaceutically acceptable salt thereof.

7. A pharmaceutical composition consisting essentially of a JNK inhibitor, a hormonal suppressor and a pharmaceutically acceptable carrier, wherein said JNK inhibitor is a benzothiazole derivative according to formula (I):

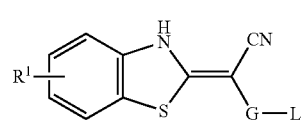

(I)

as well as its tautomers, its geometrical isomers, its optically active forms as enantiomers, diastereomers and its racemate forms, as well as pharmaceutically acceptable salts thereof, wherein:

G is a pyrimidinyl group;
L is selected from:

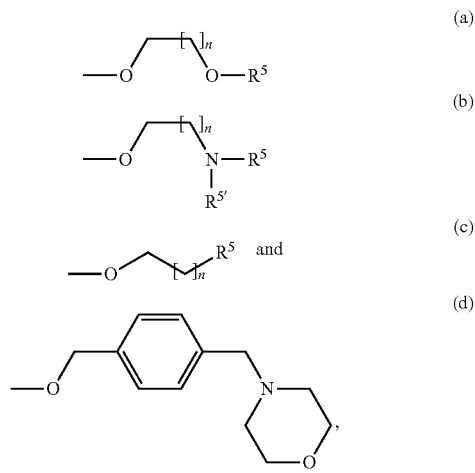

wherein n is 1 to 10;
$R^5$ and $R^{5'}$ are independently selected from each other from the group consisting of H, $C_1$-$C_{10}$ alkyl, aryl or heteroaryl, $C_1$-$C_6$ alkyl-aryl and $C_1$-$C_6$-alkyl-heteroaryl, wherein aryl is selected from the group consisting of phenyl, naphthyl and phenantrenyl, and hetero-aryl is selected from the group consisting of pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl and benzoquinolyl;

$R^1$ is selected from the group consisting of hydrogen, sulfonyl, amino, $C_1$-$C_6$-alkyl, $C_2$-$C_6$-alkenyl, $C_2$-$C_6$-alkynyl or $C_1$-$C_6$-alkoxy, aryl, halogen, cyano and hydroxy.

8. The pharmaceutical composition according to claim 7, wherein said hormonal suppressor is selected from the group consisting of a GnRH antagonist, GnRH agonist, aromatase inhibitor, progesterone receptor modulator and an estrogen receptor modulator.

9. The pharmaceutical composition according to claim 7 wherein said benzazole derivative is 1,3-benzothiazol-2-yl(2-{[4-(morpholin-4-ylmethyl)benzyl]-oxy}pyrimidin-4-yl)-acetonitrile, or a pharmaceutically acceptable salt thereof.

10. A method of treating endometriosis in an individual consisting essentially of administering a pharmaceutical composition consisting essentially of a therapeutically effective amount of a JNK inhibitor and a pharmaceutically acceptable carrier;

wherein the JNK inhibitor is a benzothiazole derivative according to formula (I)

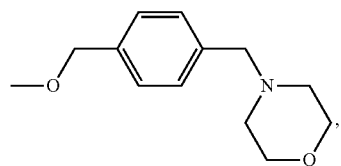

(I)

as well as its tautomers, its geometrical isomers, its optically active forms as enantiomers, diastereomers and its racemate forms, as well as pharmaceutically acceptable salts thereof, wherein:

G is a pyrimidinyl group;

L is selected from:

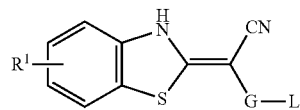

(a)

(b)

(c)

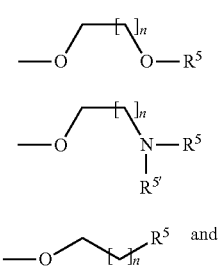

(d)

wherein n is 1 to 10;

$R^5$ and $R^{5'}$ are independently selected from each other from the group consisting of H, $C_1$-$C_{10}$ alkyl, aryl or hetero-aryl, $C_1$-$C_6$ alkyl-aryl and $C_1$-$C_6$-alkyl-heteroaryl, wherein aryl is selected from the group consisting of phenyl, naphthyl and phenantrenyl, and hetero-aryl is selected from the group consisting of pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 311-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl and benzoquinolyl;

$R^1$ is selected from the group consisting of hydrogen, sulfonyl, amino, $C_1$-$C_6$-alkyl, $C_2$-$C_6$-alkenyl, $C_2$-$C_6$-alkynyl or $C_1$-$C_6$-alkoxy, aryl, halogen, cyano and hydroxy.

11. A method of treating endometriosis in an individual in need thereof consisting essentially of administering a therapeutically effective amount of a compound selected from the group consisting of:

1,3-benzothiazol-2-yl(2,6-dimethoxy-4-pyrimidinyl)acetonitrile,
1,3-benzothiazol-2-yl[2-(benzyloxy)pyrimidin-4-yl]acetonitrile,
1,3-benzothiazol-2-yl{2-[(4-pyridin-3-ylbenzyl)oxy]pyrimidin-4-yl}acetonitrile,
1,3-benzothiazol-2-yl[2-(pyridin-4-ylmethoxy)pyrimidin-4-yl]acetonitrile,
1,3-benzothiazol-2-yl[2-(pyridin-2-ylmethoxy)pyrimidin-4-yl]acetonitrile,
1,3-benzothiazol-2-yl[2-(3-pyridin-2-ylpropoxy)pyrimidin-4-yl]acetonitrile,
1,3-benzothiazol-2-yl{2-[(4-methoxybenzyl)oxy]pyrimidin-4-yl}acetonitrile,
1,3-benzothiazol-2-yl[2-(pyridin-3-ylmethoxy)pyrimidin-4-yl]acetonitrile,
1,3-benzothiazol-2-yl{2-[2-(4-methoxyphenyl)ethoxy]pyrimidin-4-yl}acetonitrile,
1,3-benzothiazol-2-yl[2-([1,1'-biphenyl]-3-ylmethoxy)pyrimidin-4-yl]acetonitrile,
1,3-benzothiazol-2-yl{2-[(3,4,5-trimethoxybenzyl)oxy]pyrimidin-4-yl}acetonitrile,
1,3-benzothiazol-2-yl{2-[(3,4-dichlorobenzyl)oxy]pyrimidin-4-yl}acetonitrile,
1,3-benzothiazol-2-yl[2-({3-[(dimethylamino)methyl]benzyl}oxy)pyrimidin-4-yl]acetonitrile,
1,3-benzothiazol-2-yl{2-[(1-oxidopyridin-3-yl)methoxy]pyrimidin-4-yl}acetonitrile, 1,3-benzothiazol-2-yl(2-{[4-(morpholin-4-ylmethyl)benzyl]oxy}pyrimidin-4-yl)acetonitrile,
1,3-benzothiazol-2-yl{2-[(4-pyridin-2-ylbenzyl)oxy]pyrimidin-4-yl}acetonitrile,
1,3-benzothiazol-2-yl(2-{[4-(piperidin-1-ylmethyl)benzyl]oxy}pyrimidin-4-yl)acetonitrile,
1,3-benzothiazol-2-yl[2-(4-methoxyphenoxy)pyrimidin-4-yl]acetonitrile,
1,3-benzothiazol-2-yl[2-(4-butoxyphenoxy)pyrimidin-4-yl]acetonitrile,
{2-[4-(4-acetylpiperazin-1-yl)phenoxy]pyrimidin-4-yl}(1,3-benzothiazol-2-yl)acetonitrile,
[2-(4-methoxyphenoxy)pyrimidin-4-yl][5-(trifluoromethyl)-1,3-benzothiazol-2-yl]acetonitrile,
1,3-benzothiazol-2-yl(2-methoxy-4-pyrimidinyl)acetonitrile,
1,3-benzothiazol-2-yl[2-({4-[(4-methylpiperazin-1-yl)methyl]benzyl}oxy)pyrimidin-4-yl]acetonitrile,
1,3-benzothiazol-2-yl[2-({4-[(4-benzyl-piperazin-1-yl)methyl]-benzyl}oxy)pyrimidin-4-yl]acetonitrile,
1,3-benzothiazol-2-yl(2-{[4-(piperazin-1-ylmethyl)benzyl]oxy}pyrimidin-4-yl)acetonitrile,
1,3-benzothiazol-2-yl[2-({4-[(4-formylpiperazin-1-yl)methyl]benzyl}oxy)pyrimidin-4-yl]acetonitrile,
[2-({4-[(4-acetylpiperazin-1-yl)methyl]benzyl}oxy)pyrimidin-4-yl](1,3-benzothiazol-2-yl)acetonitrile,
(3H-Benzothiazol-2-ylidene)-{2-[4-(4-[1,2,4]oxadiazol-3-ylmethyl-piperazin-1-ylmethyl)-benzyloxy]-pyrimidin-4-yl}-acetonitrile,
4-(4-{4-[(3H-Benzothiazol-2-ylidene)-cyano-methyl]-pyrimidin-2-yloxymethyl}-benzyl)-piperazine-1-carboxylic acid methyl ester,
2-[4-(4-{4-[(3H-Benzothiazol-2-ylidene)-cyano-methyl]-pyrimidin-2-yloxymethyl}-benzyl)-piperazin-1-yl]-acetamide,
(2-{4-[4-(2-Amino-acetyl)-piperazin-1-ylmethyl]-benzyloxy}-pyrimidin-4-yl)-(3H-benzothiazol-2-ylidene)-acetonitrile,
[4-(4-{4-[(3H-Benzothiazol-2-ylidene)-cyano-methyl]-pyrimidin-2-yloxymethyl}-benzyl)-piperazin-1-yl]-acetic acid methyl ester,
(3H-Benzothiazol-2-ylidene)-(2-{4-[4-(2-methoxy-ethyl)-piperazin-1-ylmethyl]-benzyloxy}-pyrimidin-4-yl)-acetonitrile,
4-(4-{4-[(3H-Benzothiazol-2-ylidene)-cyano-methyl]-pyrimidin-2-yloxymethyl}-benzyl)-piperazine-1-carboxylic acid dimethylamide,
(3H-Benzothiazol-2-ylidene)-{2-[4-(4-ethyl-piperazin-1-ylmethyl)-benzyloxy]-pyrimidin-4-yl}-acetonitrile,
(3H-Benzothiazol-2-ylidene)-(2-{4-[4-(2-hydroxy-ethyl)-piperazin-1-ylmethyl]-benzyloxy}-pyrimidin-4-yl)-acetonitrile; and
pharmaceutically acceptable salts thereof.

12. A method of treating endometriosis in an individual in need thereof consisting essentially of sequentially or simultaneously administering a therapeutically effective amount of a JNK inhibitor in combination with a hormonal suppressor or fertility drugs, wherein the JNK inhibitor is a compound selected from the group consisting of:
1,3-benzothiazol-2-yl(2,6-dimethoxy-4-pyrimidinyl)acetonitrile,
1,3-benzothiazol-2-yl[2-(benzyloxy)pyrimidin-4-yl]acetonitrile,
1,3-benzothiazol-2-yl {2-[(4-pyridin-3-ylbenzyl)oxy]pyrimidin-4-yl}acetonitrile,
1,3-benzothiazol-2-yl[2-(pyridin-4-ylmethoxy)pyrimidin-4-yl]acetonitrile,
1,3-benzothiazol-2-yl[2-(pyridin-2-ylmethoxy)pyrimidin-4-yl]acetonitrile,
1,3-benzothiazol-2-yl[2-(3-pyridin-2-ylpropoxy)pyrimidin-4-yl]acetonitrile,
1,3-benzothiazol-2-yl{2-[(4-methoxybenzyl)oxy]pyrimidin-4-yl}acetonitrile,
1,3-benzothiazol-2-yl[2-(pyridin-3-ylmethoxy)pyrimidin-4-yl]acetonitrile,
1,3-benzothiazol-2-yl{2-[2-(4-methoxyphenyl)ethoxy]pyrimidin-4-yl}acetonitrile,
1,3-benzothiazol-2-yl[2-([1,1'-biphenyl]-3-ylmethoxy)pyrimidin-4-yl]acetonitrile,
1,3-benzothiazol-2-yl{2-[(3,4,5-trimethoxybenzyl)oxy]pyrimidin-4-yl}acetonitrile,
1,3-benzothiazol-2-yl {2-[(3,4-dichlorobenzyl)oxy]pyrimidin-4-yl}acetonitrile,
1,3-benzothiazol-2-yl[2-({3-[(dimethylamino)methyl]benzyl}oxy)pyrimidin-4-yl]acetonitrile,
1,3-benzothiazol-2-yl{2-[(1-oxidopyridin-3-yl)methoxy]pyrimidin-4-yl}acetonitrile,
1,3-benzothiazol-2-yl(2-{[4-(morpholin-4-ylmethyl)benzyl]oxy}pyrimidin-4-yl)acetonitrile,
1,3-benzothiazol-2-yl{2-[(4-pyridin-2-ylbenzyl)oxy]pyrimidin-4-yl}acetonitrile,
1,3-benzothiazol-2-yl(2-{[4-(piperidin-1-ylmethyl)benzyl]oxy}pyrimidin-4-yl)acetonitrile,
1,3-benzothiazol-2-yl[2-(4-methoxyphenoxy)pyrimidin-4-yl]acetonitrile,
1,3-benzothiazol-2-yl[2-(4-butoxyphenoxy)pyrimidin-4-yl]acetonitrile,
{2-[4-(4-acetylpiperazin-1-yl)phenoxy]pyrimidin-4-yl}(1,3-benzothiazol-2-yl)acetonitrile,
[2-(4-methoxyphenoxy)pyrimidin-4-yl][5-(trifluoromethyl)-1,3-benzothiazol-2-yl]acetonitrile,
1,3-benzothiazol-2-yl(2-methoxy-4-pyrimidinyl)acetonitrile,
1,3-benzothiazol-2-yl[2-({4-[(4-methylpiperazin-1-yl)methyl]benzyl}oxy)pyrimidin-4-yl]acetonitrile,
1,3-benzothiazol-2-yl[2-({4-[(4-benzyl-piperazin-1-yl)methyl]-benzyl}oxy)pyrimidin-4-yl]acetonitrile,
1,3-benzothiazol-2-yl(2-{[4-(piperazin-1-ylmethyl)benzyl]oxy}pyrimidin-4-yl)acetonitrile,
1,3-benzothiazol-2-yl[2-({4-[(4-formylpiperazin-1-yl)methyl]benzyl}oxy)pyrimidin-4-yl]acetonitrile,
[2-({4-[(4-acetylpiperazin-1-yl)methyl]benzyl}oxy)pyrimidin-4-yl](1,3-benzothiazol-2-yl)acetonitrile,
(3H-Benzothiazol-2-ylidene)-{2-[4-(4-[1,2,4]oxadiazol-3-ylmethyl-piperazin-1-ylmethyl)-benzyloxy]-pyrimidin-4-yl}-acetonitrile,
4-(4-{4-[(3H-Benzothiazol-2-ylidene)-cyano-methyl]-pyrimidin-2-yloxymethyl}-benzyl)-piperazine-1-carboxylic acid methyl ester,
2-[4-(4-{4-[(3H-Benzothiazol-2-ylidene)-cyano-methyl]-pyrimidin-2-yloxymethyl}-benzyl)-piperazin-1-yl]-acetamide,
(2-{4-[4-(2-Amino-acetyl)-piperazin-1-ylmethyl]-benzyloxy}-pyrimidin-4-yl)-(3H-benzothiazol-2-ylidene)-acetonitrile,
[4-(4-{4-[(3H-Benzothiazol-2-ylidene)-cyano-methyl]-pyrimidin-2-yloxymethyl}-benzyl)-piperazin-1-yl]-acetic acid methyl ester,
(3H-Benzothiazol-2-ylidene)-(2-{4-[4-(2-methoxy-ethyl)-piperazin-1-ylmethyl]-benzyloxy}-pyrimidin-4-yl)-acetonitrile,
4-(4-{4-[(3H-Benzothiazol-2-ylidene)-cyano-methyl]-pyrimidin-2-yloxymethyl}-benzyl)-piperazine-1-carboxylic acid dimethylamide, (3H-Benzothiazol-2-ylidene)-{2-[4-(4-ethyl-piperazin-1-ylmethyl)-benzyloxy]-pyrimidin-4-yl}-acetonitrile, (3H-Benzothiazol-2-ylidene)-(2-{4-[4-(2-hydroxy-ethyl)-piperazin-1-ylmethyl]-benzyloxy}-pyrimidin-4-yl)-acetonitrile; and pharmaceutically acceptable salts thereof.

13. The method according to claim 12, wherein said hormonal suppressor is selected from the group consisting of a GnRH antagonist, GnRH agonist, aromatase inhibitor, progesterone receptor modulator and an estrogen receptor modulator.

14. A pharmaceutical composition consisting essentially of a JNK inhibitor, a hormonal suppressor and a pharmaceutically acceptable carrier, wherein said JNK inhibitor is a compound selected from the group consisting of:

1,3-benzothiazol-2-yl(2,6-dimethoxy-4-pyrimidinyl)acetonitrile, 1,3-benzothiazol-2-yl[2-(benzyloxy)pyrimidin-4-yl]acetonitrile, 1,3-benzothiazol-2-yl{2-[(4-pyridin-3-ylbenzyl)oxy]pyrimidin-4-yl}acetonitrile, 1,3-benzothiazol-2-yl[2-(pyridin-4-ylmethoxy)pyrimidin-4-yl]acetonitrile, 1,3-benzothiazol-2-yl[2-(pyridin-2-ylmethoxy)pyrimidin-4-yl]acetonitrile, 1,3-benzothiazol-2-yl[2-(3-pyridin-2-ylpropoxy)pyrimidin-4-yl]acetonitrile, 1,3-benzothiazol-2-yl{2-[(4-methoxybenzyl)oxy]pyrimidin-4-yl}acetonitrile, 1,3-benzothiazol-2-yl[2-(pyridin-3-ylmethoxy)pyrimidin-4-yl]acetonitrile, 1,3-benzothiazol-2-yl {2-[2-(4-methoxyphenyl)ethoxy]pyrimidin-4-yl}acetonitrile, 1,3-benzothiazol-2-yl[2-([1,1'-biphenyl]-3-ylmethoxy)pyrimidin-4-yl]acetonitrile, 1,3-benzothiazol-2-yl{2-[(3,4,5-trimethoxybenzyl)oxy]pyrimidin-4-yl}acetonitrile, 1,3-benzothiazol-2-yl{2-[(3,4-dichlorobenzyl)oxy]pyrimidin-4-yl}acetonitrile, 1,3-benzothiazol-2-yl[2-({3-[(dimethylamino)methyl]benzyl}oxy)pyrimidin-4-yl]acetonitrile, 1,3-benzothiazol-2-yl{2-[(1-oxidopyridin-3-yl)methoxy]pyrimidin-4-yl}acetonitrile, 1,3-benzothiazol-2-yl(2-{[4-(morpholin-4-ylmethyl)benzyl]oxy}pyrimidin-4-yl)acetonitrile, 1,3-benzothiazol-2-yl{2-[(4-pyridin-2-ylbenzyl)oxy]pyrimidin-4-yl}acetonitrile, 1,3-benzothiazol-2-yl(2-{[4-(piperidin-1-ylmethyl)benzyl]oxy}pyrimidin-4-yl)acetonitrile, 1,3-benzothiazol-2-yl[2-(4-methoxyphenoxy)pyrimidin-4-yl]acetonitrile, 1,3-benzothiazol-2-yl[2-(4-butoxyphenoxy)pyrimidin-4-yl]acetonitrile, {2-[4-(4-acetylpiperazin-1-yl)phenoxy]pyrimidin-4-yl}(1,3-benzothiazol-2-yl)acetonitrile,

[2-(4-methoxyphenoxy)pyrimidin-4-yl][5-(trifluoromethyl)-1,3-benzothiazol-2-yl]acetonitrile, 1,3-benzothiazol-2-yl(2-methoxy-4-pyrimidinyl)acetonitrile, 1,3-benzothiazol-2-yl[2-({4-[(4-methylpiperazin-1-yl)methyl]benzyl}oxy)pyrimidin-4-yl]acetonitrile, 1,3-benzothiazol-2-yl[2-({4-[(4-benzyl-piperazin-1-yl)methyl]-benzyl}oxy)pyrimidin-4-yl]acetonitrile, 1,3-benzothiazol-2-yl(2-{[4-(piperazin-1-ylmethyl)benzyl]oxy}pyrimidin-4-yl)acetonitrile, 1,3-benzothiazol-2-yl[2-({4-[(4-formylpiperazin-1-yl)methyl]benzyl}oxy)pyrimidin-4-yl]acetonitrile,

[2-({4-[(4-acetylpiperazin-1-yl)methyl]benzyl}oxy)pyrimidin-4-yl](1,3-benzothiazol-2-yl)acetonitrile, (3H-Benzothiazol-2-ylidene)-{2-[4-(4-[1,2,4]oxadiazol-3-ylmethyl-piperazin-1-ylmethyl)-benzyloxy]-pyrimidin-4-yl}-acetonitrile, 4-(4-{4-[(3H-Benzothiazol-2-ylidene)-cyano-methyl]-pyrimidin-2-yloxymethyl}-benzyl)-piperazine-1-carboxylic acid methyl ester, 2-[4-(4-{4-[(3H-Benzothiazol-2-ylidene)-cyano-methyl]-pyrimidin-2-yloxymethyl}-benzyl)-piperazin-1-yl]-acetamide, (2-{4-[4-(2-Amino-acetyl)-piperazin-1-ylmethyl]-benzyloxy}-pyrimidin-4-yl)-(3H-benzothiazol-2-ylidene)-acetonitrile,

[4-(4-{4-[(3H-Benzothiazol-2-ylidene)-cyano-methyl]-pyrimidin-2-yloxymethyl}-benzyl)-piperazin-1-yl]-acetic acid methyl ester, (3H-Benzothiazol-2-ylidene)-(2-{4-[4-(2-methoxy-ethyl)-piperazin-1-ylmethyl]-benzyloxy}-pyrimidin-4-yl)-acetonitrile, 4-(4-{4-[(3H-Benzothiazol-2-ylidene)-cyano-methyl]-pyrimidin-2-yloxymethyl}-benzyl)-piperazine-1-carboxylic acid dimethylamide, (3H-Benzothiazol-2-ylidene)-{2-[4-(4-ethyl-piperazin-1-ylmethyl)-benzyloxy]-pyrimidin-4-yl}-acetonitrile, (3H-Benzothiazol-2-ylidene)-(2-{4-[4-(2-hydroxy-ethyl)-piperazin-1-ylmethyl]-benzyloxy}-pyrimidin-4-yl)-acetonitrile; and pharmaceutically acceptable salts thereof.

15. The pharmaceutical composition according to claim 14, wherein said hormonal suppressor is selected from the group consisting of a GnRH antagonist, GnRH agonist, aromatase inhibitor, progesterone receptor modulator and an estrogen receptor modulator.

* * * * *

UNITED STATES PATENT AND TRADEMARK OFFICE
CERTIFICATE OF CORRECTION

PATENT NO.       : 8,592,414 B2                                                 Page 1 of 1
APPLICATION NO.  : 11/988572
DATED            : November 26, 2013
INVENTOR(S)      : Palmer et al.

It is certified that error appears in the above-identified patent and that said Letters Patent is hereby corrected as shown below:

In the Claims:

In column 48, Claim 4, line 3 after "1,2,3-oxadiazolyl," insert --1,2,4-oxadia-zolyl,--

Signed and Sealed this
Eleventh Day of March, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,592,414 B2                                                Page 1 of 1
APPLICATION NO.  : 11/988572
DATED            : November 26, 2013
INVENTOR(S)      : Palmer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 475 days.

Signed and Sealed this
Twenty-second Day of September, 2015

Michelle K. Lee
*Director of the United States Patent and Trademark Office*